(12) United States Patent
Li et al.

(10) Patent No.: US 11,559,585 B2
(45) Date of Patent: Jan. 24, 2023

(54) CONJUGATES OF ACTIVE PHARMACEUTICAL INGREDIENTS

(71) Applicant: THE REGENTS OF THE UNIVERSITY OF CALIFORNIA, Oakland, CA (US)

(72) Inventors: Yuanpei Li, Davis, CA (US); Xiangdong Xue, Davis, CA (US); Yee Huang, Davis, CA (US); Zhao Ma, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/622,722

(22) PCT Filed: Jun. 15, 2018

(86) PCT No.: PCT/US2018/037895
§ 371 (c)(1),
(2) Date: Dec. 13, 2019

(87) PCT Pub. No.: WO2018/232334
PCT Pub. Date: Dec. 20, 2018

(65) Prior Publication Data
US 2021/0138084 A1    May 13, 2021

Related U.S. Application Data

(60) Provisional application No. 62/521,181, filed on Jun. 16, 2017.

(51) Int. Cl.
*A61K 9/00* (2006.01)
*A61K 47/69* (2017.01)
(Continued)

(52) U.S. Cl.
CPC ........ *A61K 47/6929* (2017.08); *A61K 31/337* (2013.01); *A61K 31/417* (2013.01);
(Continued)

(58) Field of Classification Search
CPC .................................................. A61K 31/365
See application file for complete search history.

(56) References Cited

U.S. PATENT DOCUMENTS 5,169,944 A * 12/1992 Nelson .................. A61K 49/06
424/9.36
5,948,750 A    9/1999  Garsky et al.
(Continued)

FOREIGN PATENT DOCUMENTS

| CN | 105535991 | 5/2016 |
| CN | 105617379 | 6/2016 |

(Continued)

OTHER PUBLICATIONS

Zhao, Novel porphyrin—daunomycin hybrids: Synthesis and preferential binding to G-quadruplexes over i-motif, Spectrochimica Acta Part A. Molecular and Blomolecular Spectroscopy, 2015, 137, 227-235 (2015).*

(Continued)

*Primary Examiner* — Paul W Dickinson
(74) *Attorney, Agent, or Firm* — Mintz, Levin, Cohn, Ferris, Glovsky and Popeo, P.C.

(57) ABSTRACT

The present inventions provides drug-drug conjugates, drug-porphyrin conjugates, nanoparticles of the conjugates, as well as modified nanoparticles having PEGylated exteriors or encapsulated by red blood cell vesicles. The conjugates, nanoparticles and nanocarriers are useful for treating cancers and other diseases, as well as for imaging diseased tissue or organs.

24 Claims, 17 Drawing Sheets

(51) Int. Cl.

| | |
|---|---|
| *A61K 31/337* | (2006.01) |
| *A61K 31/417* | (2006.01) |
| *A61K 31/475* | (2006.01) |
| *A61K 31/4965* | (2006.01) |
| *A61K 31/704* | (2006.01) |
| *A61K 41/00* | (2020.01) |
| *G01N 23/02* | (2006.01) |

(52) U.S. Cl.
CPC ........ *A61K 31/475* (2013.01); *A61K 31/4965* (2013.01); *A61K 31/704* (2013.01); *A61K 41/0033* (2013.01); *G01N 23/02* (2013.01)

(56) References Cited

U.S. PATENT DOCUMENTS

| | | | |
|---|---|---|---|
| 8,354,455 | B2 | 1/2013 | Satyam |
| 9,901,644 | B2 | 2/2018 | Kratz et al. |
| 11,219,692 | B2 | 1/2022 | Lam et al. |
| 2004/0192665 | A1 | 9/2004 | Frydman et al. |
| 2010/0144647 | A1 | 6/2010 | Kratz et al. |
| 2013/0210756 | A1 | 8/2013 | Kim et al. |
| 2017/0105998 | A1 | 4/2017 | Goldman et al. |

FOREIGN PATENT DOCUMENTS

| | | |
|---|---|---|
| WO | 2006007261 A1 | 1/2006 |
| WO | 2006027711 A2 | 3/2006 |
| WO | 2013051778 A1 | 4/2013 |
| WO | 2013132485 A1 | 9/2013 |

OTHER PUBLICATIONS

Zhao, Novel porphyrin-daunomycin hybrids: Synthesis and preferential binding to G-quadruplexes over i-motif, Spectrochimica Acta Part A: Molecular and Biomolecular Spectroscopy,2015, 137, 227-235 (Year: 2015).*
International Search Report and Written Opinion received for PCT Application No. PCT/US2018/037895, dated Sep. 6, 2018, 9 pages.
Partial Supplementary European Search Report received for EP Application No. 18818520.1, dated Feb. 24, 2021, 23 pages.
Ajaj et al. (Feb. 2009) "Development of Protein-Binding Bifunctional Linkers for a New Generation of Dual-Acting Prodrugs", Bioconjugate Chemistry, 20(2):390-396.
Loconte et al. (Dec. 2008) "A Phase I Pharmacodynamic Trial of Bortezomib in Combination with Doxorubicin in Patients with Advanced Cancer", Cancer Chemotherapy and Pharmacology, 63(1):109-115.
Shelly et al. (Sep. 15, 2015) "Polymer Therapeutics Rationally-Designed for a Combination Therapy of Paclitaxel and Doxorubicin", Cancer Microenvironment, 8(P92):S131.
Wang et al. (Apr. 10, 2017) "Multifunctional Telodendrimer Nanocarriers Restore Synergy of Bortezomib and Doxorubicin in Ovarian Cancer Treatment", Cancer Research, 77(12):3293-3305.
Wang et al. (Feb. 24, 2016) "Precise Polymerization of a Highly Tumor Microenvironment-Responsive Nanoplatform for Strongly Enhanced Intracellular Drug Release", ACS Applied Materials & Interfaces, 8(9):5833-5846.
Xu et al. (Jan. 28, 2016) "Nanomicelles Based on a Boronate Ester-linked Diblock Copolymer as the Carrier of Doxorubicin With Enhanced Cellular Uptake", Colloids and Surfaces B: Biointerfaces, 141:318-326.
You et al., "Synthesis of pheophorbide-a conjugates with anticancer drugs as potential cancer diagnostic and therapeutic agents", Bioorg. Med. Chem., 2011, 19, 5383-5391.

* cited by examiner

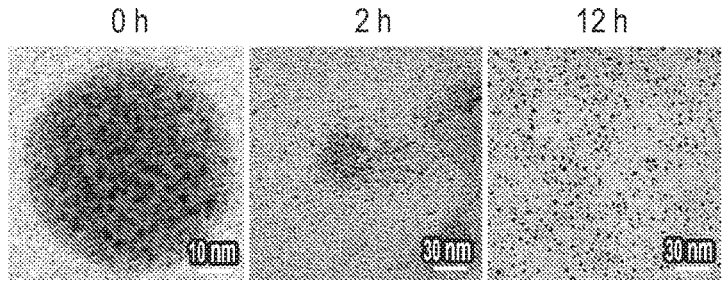
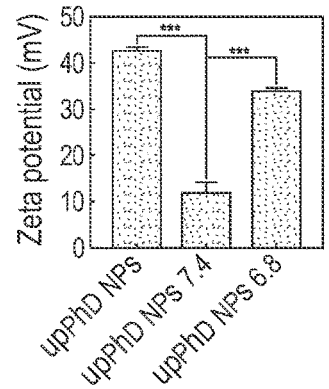
FIG. 11A
FIG. 11B
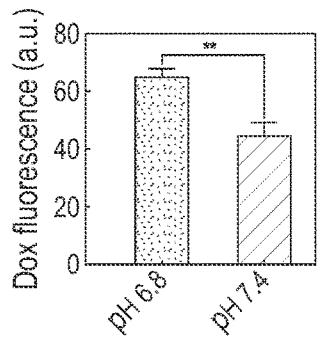
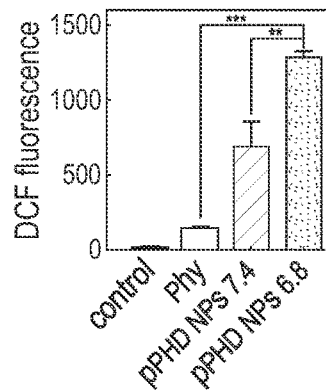
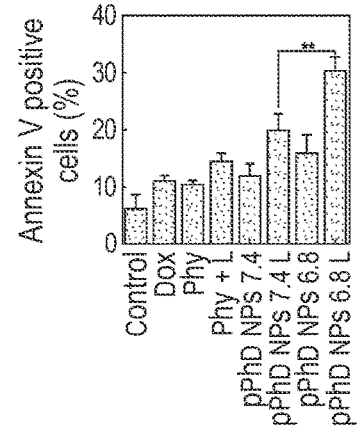
FIG. 11C
FIG. 11D
FIG. 11E
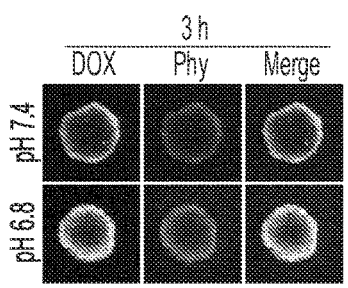
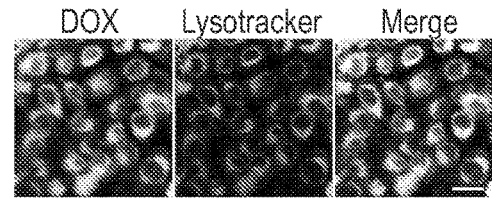
FIG. 11F
FIG. 11G
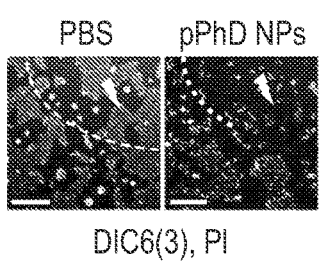
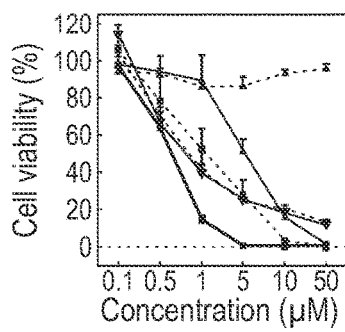
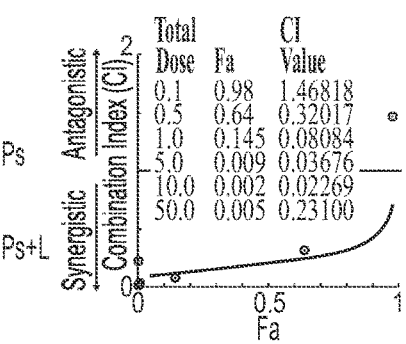
FIG. 11H
FIG. 11I
FIG. 11J

CONJUGATES OF ACTIVE PHARMACEUTICAL INGREDIENTS

CROSS-REFERENCE TO RELATED APPLICATIONS

This application claims priority to U.S. Provisional Application No. 62/521,181, filed Jun. 16, 2017, incorporated herein in its entirety for all purposes.

STATEMENT AS TO RIGHTS TO INVENTIONS MADE UNDER FEDERALLY SPONSORED RESEARCH AND DEVELOPMENT

This invention was made with government support under Grant Nos. CA199668 and HD086195, awarded by the National Institutes of Health. The government has certain rights in the invention.

BACKGROUND OF THE INVENTION

Nanoscaled drug delivery system (NDDS) is engineered by nanotechnologies for targetedly delivering and controllably releasing the active pharmaceutical ingredients (API) to specific focus. The application of NDDS is widely expected to bring new hope to create novel therapeutics for cancer therapy, as the NDDS enable to improve the solubility of APIs, protect them from degradation, enhance the blood circulation time and bring them specifically to the tumour tissue without inducing side effects along the healthy organs. The clinic trended applications of inorganic NDDSs were restrained, due to their potentially accumulated long-term toxicities. Therefore, scientists put great efforts on developing of organic NDDSs, which mainly include liposomes, micelles, polymeric nanoparticles, protein-based nanoparticles, etc. Thanks to the excellent biocompatibility and biodegradation of organic materials, a few nanodrugs are already commercial available, such as paclitaxel loaded albumin (Abraxane), liposomal doxorubicin (Doxil) and paclitaxel loaded polymeric micelle (Genexol-PM), etc. Nevertheless, these organic NDDSs still suffer from the drawback of low drug loading capacity (% DL, confined as [entrapped drug/nanoparticles weight]*100). So far, most organic NDDSs have been reported are with % DL below 20 wt %, which means that a majority part of non-pharmaceutical ingredients are employed just for delivering a minority of APIs; and this step consumes huge resources. Most carriers are claimed to be nontoxic, this claim is, however, limited within a safety threshold. When we need to elevate the API amounts to achieve better efficacy, the quantities of non-pharmaceutical ingredients will be increased correspondingly, and may surpass the safety threshold, thus exhibit toxicities. For instance, the most acceptable polymer, polyethylene glycol (PEG), shows some extents of toxicity when they were administrated in high concentrations.

To address this issue, one-component nanomedicine (OCN) was developed for improving the % DL and correspondingly decreasing the carriers amounts. The OCN directly integrates hydrophobic antineoplastic drugs into the building blocks, acting as hydrophobic core of the nanoparticles, thus providing driven force for molecules self assembly in aqueous environment. As each building block intrinsically harbors one share of API, the drug loading efficiency enables to reach a higher level, comparing to the conventional NDDSs. As such, the non pharmaceutical parts of OCN are mostly introduced for carrying the payloads, like "on trick pony", their sole role is to deliver the pharmaceutical ingredients. When they fulfill the drug delivery mission and come to post-delivery period, they become useless, and may yield toxicities for our health. Not only that, their dispositions remain mysterious both in vitro and in vivo, as most OCNs are not traceable. To impart the traceable features, exotic imaging agents are usually introduced to the NDDS. However, the introduced imaging agents only indicate their own dispositions, but not the real biological behaviours of NDDSs once the imaging agents leak out. Therefore, it is desirable to develop self-indicating NDDSs with innate imaging features to unveil the real biological dispositions. In our mind, the ideal NDDS should meet the following features: i) Drug delivery. First and formost, they can be self-assembled into a nanostructure to carry the drugs to the specific focus or providing the driven force to guide the drugs assemblying into nano-formulations; ii) High % DL. The % DL is requisite to be as high as possible, leading to less non-pharmaceutical ingredients introduction, and therefore decreasing the unnecessary toxicities; iii) Self-indicating. The NDDSs, themselves, are engineered with imaging features, so that their real biological dispositions can be visualized; iv) Therapeutic effect or synergistic effect. The carrier parts of NDDS are better to exhibit therapeutical effect, which can make the whole NDDS become more efficacious. Or at least, they can achieve some extent of synergistic effect with encapsulated API, and thus improve entire efficacy of NDDS.

Nowadays, chemotherapy is widely used in clinic for cancer treatment. However, sole modal chemotherapy is not efficient enough to control the tumour progression, as cancer is extremely aggressive, and constantly with high risk of recurrence even they seem to be cured. Combination therapy is a promising means to address these problems. The non-invasive phototherapies, including photothermal therapy (PTT) and photodynamic therapy (PDT), are conceived as two alternative tumour ablation methods. PTT is realized by transforming photo energy to heat, and PDT refers to produce the reactive oxygen species (ROS) in the circumstance. The phototherapeutic agents are intrinsically non-toxic in dark, but with high photo-induced toxicity that only occurs in a confined area where the laser points, phototherapies thus enable to accurately ablate the specific regions of tumour in spatiotemporal manner. Hence, the combinations of highly controllable PTT and PDT with conventional chemotherapy may achieve precise and more efficient tumour ablation, and lower the risk of recurrence.

Here, we inaugurated a self-indicating full active pharmaceutical ingredients nanoparticle (FAPIN), which was not only composed with 100% API, but also seamlessly orchestrated a broad range of smart and clinically relevant functionalities in one simple nanoparticle, including self-indicating features, like energy transfer dominated dual-fluorogenic and near infrared fluorescence (NIRF) imaging; and controllable trimodality therapy (photothermal-, photodynamic- and chemo-therapies). To realize 100% API loading capacity, we only introduced two commercially available APIs into the FAPIN. The first API was a porphyrin derivative, pheophorbide A (Pa), acting as the hydrophobic building blocks. Porphyrin derivatives were extensively employed to build theranostic nanoplatform, which possesses excellent PTT and PDT effects, and NIRF imaging features. A FDA-proved chemo-drug, irinotecan (Ir, Camptosar®), was introduced as the second API. Ir is a relatively hydrophilic anti-neoplastic drug, which prevents DNA from unwinding by inhibition of topoisomerase II, and thus terminate the proliferations of tumour cells. As illustrated in FIG. 1, Pa and Ir were covalently conjugated through cleavable ester bond, and forming amphiphilic chemical structures (Pa—Ir conjugates, PI). PI molecules can be rearranged and forming nano-formulations (Pa—Ir nanoparticle, PIN) in aqueous solution through self-assembly. In this particular construct, 100% API loading capacity was achieved, as the PIN were directlssy fabricated through pure APIs self-assembly. In PIN, the fluorescence of Ir was quenched because of the energy transfer from Ir to Pa, and the fluorescence of Pa was further inactivated, due to the π-π stacking among the planar chemical structures of Pa in the nanostructure of PIN. Hence, even the building blocks of PIN were composed with two fluorescently molecules (Pa with excellent NIRF and Ir with blue fluorescence), PIN exhibited no fluorescence, as an energy transfer relay dominated and inactivated both fluorescence of Pa and Ir. The dual fluorescence inactivation was supposed to give a dual-fluorogenic process when specific stimuli were applied and caused the energy transfer relay invalid. The conventional NDDSs usually need extra step to introduce imaging agents to indicate their biological dispositions. The PIN was intrinsically self-indicating, Pa bestowed the nanoparticles with excellent NIRF imaging feature, which enable to indicate the behaviours of PIN in vivo. The energy transfer dominated dual-fluorogenic process contributed to indicate the drug releasing behaviours of PIN in real time manner. PIN was then administrated into patient derived xenograft (PDX) tumour bearing mice through tail vein injection, because of the excellent enhanced permeability and retention (EPR) effect of solid tumour, PIN preferentially accumulated in tumour region, and specifically exerted the anti-cancer role. PIN that accumulated in tumours were triggered with laser beam, and realized laser triggered trimodality therapy, including direct phototherapies (PPT and PDT), and indirect chemotherapy (laser-triggered drug release).

BRIEF SUMMARY OF THE INVENTION

In one embodiment, the present invention provides a compound of Formula I:

wherein X is a hydrophilic therapeutic agent, L is absent or is a linker, and Y is a photo-active compound comprising a porphyrin or analog thereof, or a hydrophobic therapeutic agent, where the compound is other than doxorubicin-10-hydroxycamptothecin and irinotecan-chlorambucil.

BRIEF DESCRIPTION OF THE DRAWINGS

FIG. 2a) Chemical synthesis of PI conjugate; FIG. 2b) DLS results showed the size distributions and polydispersity index (PDI) of PIN; FIG. 2c) The morphology of PIN observed by TEM, the scale bar is 100 nm; FIG. 2d) UV-Vis absorbance of Pa, Ir and PI; FIG. 2e) Fluorescence behaviours of Pa, Ir, PI and PIN. Excitation was set as 370 nm (the optimal excitation of Ir); FIG. 2f) the fluorescence spectra Pa, Ir, PI and PIN with excitations of 412 nm (the maximum excitation of Pa); FIG. 2g) Near-infrared fluorescence imaging of PI and PIN with an excitation bandpass filter at 625/20 nm and an emission filter at 700/35 nm. PI was obtained by dissolved PI molecules in good solvent (DMSO); FIG. 2h) Thermal images and FIG. 2i) Quantitative temperature variation curves of PIN and PI. The temperatures were monitored by a thermal camera after irradiation with NIR laser (680 nm) at 0.3 w/cm$^2$ for 3 min. FIG. 2j) Single oxygen generations of PIN and PI upon light irradiation (680 nm at 0.3 w/cm$^2$ for 3 min) measured by using SOSG as an indicator. The results were expressed as the mean±s.d.

FIG. 3a) Drug releasing curves of PIN in different pH environments (pH 7.4 and pH 5.0 corresponded to neutral and acidic pH, respectively), with or without laser treatments. The samples were exposed under intermittent laser, each timepoint denoted a 3 min laser treatment, followed with a 12 min interval (to allow the sample temperature dropping to room temperature). The last timepoint (13$^{rd}$) was set by putting the 12$^{nd}$ laser treated samples in room temperature overnight, and the Ir fluorescence was directly tested without the 13$^{rd}$ laser treatment (to mimic the time dependent, one time laser treatment drug release). FIG. 3b) Blue fluorescence recovery of Ir revealed drug release of PIN. The samples were illuminated under 365 nm UV lamp. "Pre" denoted the control samples before laser treatments (fresh made). "0" denoted non-laser treated samples, and "L" and "H" corresponded to low and high laser powers respectively. FIG. 3c) cell viabilities of Pa, Ir, Pa/Ir mixture and PIN towards U87-MG tumour cells with or, without laser treatments. The molar concentrations of Pa or Ir in all treatments were ranging from 0.1 µM to 50 µM. FIG. 3d) CLSM observation of time dependent drug release and subcellular distributions of PIN with or without laser treatments. 10 µM PIN was incubated with U87-MG cells for 2 h, then washed off and replaced with fresh medium. The PIN contained U87-MG cells were treated with laser for 3 min, and incubated for another 22 h. The scale bar is 50 µm. FIG. 3e) Lysosomes colocalization of PIN in U87-MG cells. Cells were treated with the identical procedures of d), and stained with LysoTracker™ Green DND-26 for 30 min, then observed by CLSM. The scale bar is 50 µm. FIG. 3f) FACS quantitatively exhibited the ROS production of PIN in U87-MG tumour cells. Left, cells treated with laser; Middle, PIN incubated cells without laser treatment; Right, PIN treated cells with laser treatment. The ROS production indicated by DCF-DA (x-axis), Pa denoted the fluorescence of PIN (y-axis). FIG. 3g) Light triggered controllable and precise cancer therapy in cellular level. The laser treated areas were marked with 'L'. The scale bar is 200 µm.

FIG. 4a) Work flow of animal experiments. PDX glioma tissues were subcutaneously inoculated into the flank of nude mice. When the tumours were fully developed, PIN and other materials were i.v. administrated through tail vein, Pa+Ir and PIN treated mice (tumours) were exposed under laser after 24 h and 48 h administration. Mice were monitored in the following weeks for survival and tumour profiling. FIG. 4b) Laser triggered NIRF imaging of PIN treated mice. The mice bore two tumours, the left tumour (pointed out by white circle) was not treated with laser, and the right one (red circle) was treated with laser (0.8 w/cm$^2$) for 3 min. FIG. 4c) Ex vivo imaging of PIN treated mice, the upper tumour was treated with laser. Sk, skin; M, muscle; K, kidney; SI, small intestine; S, spleen; Li, liver; Lu, lung, H, heart; T, tumour. FIG. 4d) Photothermal effect of PBS, PIN L, PIN H and Pa+Ir H groups. Laser treatments were introduced 24 h after the materials administration. FIG. 4e) NIRF imaging of ROS production of the PBS, PIN L, PIN H and Pa—Ir H treated mice. FIG. 4f) Statistics data of the PDT effects performed on PBS, PIN L, PIN H and Pa+Ir H treated mice. FIG. 4g) Tumour volumes variations of the PDX glioma bore mice (n=6). The mice were treated with free Ir, Pa+Ir and PIN respectively, PBS treated group was set as control. FIG. 4h) Kaplan—Meier curves for mice treated with PBS, free Ir, Pa—Ir and PIN. Survival cut-off criteria included tumour ulceration or compassionate euthanasia, when the tumour size was more than 1000 mm$^3$ in volume, or if the tumour impeded eating, urination, defecation or ambulation. FIG. 4i) Tumours profiles of each groups after 2 doses treatments. FIG. 4j) The completely cured mice (2 of PIN L group and 3 of PIN H group), the mice were treated with PIN under high and low dose laser treatments, the red circles denote the treated tumour region that after the laser burned scars were naturally fell off. FIG. 4k) Histopathological evaluation of PBS or PIN treated tumours (24 h after irradiation), the light dose was 0.8 w/cm$^2$. The scale bar in 10× images were 200 µm, and in 40× were 60 µm. The materials doses: Ir dose, 20 mg/kg, PIN dose, 40 mg/kg, and Pa—Ir dose, 20 mg/kg Pa mixed with 20 mg/kg Ir. High laser power was 0.8 w/cm$^2$, and low laser dose was 0.4 w/cm$^2$. All laser treatments lasted for 3 min. All results were expressed as the mean±s.d. *P<0.05, **P<0.01, one-way ANOVA.

FIG. 5a) Chemical structure of Mn$^{2+}$ chelated PI molecules. FIG. 5b) The fluorescence behaviours of the PI molecules, before and after the metal chelation. Excitation is 412 nm. FIG. 5c) Concentration dependent relaxation of Mn$^{2+}$ chelated PIN. By calculation, the r$^1$ is 4.38 mM$^{-1}$/S. FIG. 5d) T$_1$ signal intensity variations of PIN in U87 cells, the MRI signal variations were at different Mn$^{2+}$ concentrations of 10, 20, 40, 60, 80, 160 µg/mL.

(FIG. 10a) TEM micrograph of pPhD NPs (50 µM). (FIG. 10b) Size distributions of pPhD NPs (50 µM) measured by dynamic light scattering (DLS). (FIG. 10c) UV-vis absorbance of 50 µM Phy, DOX and PhD monomer. Fluorescent spectra of 50 µM Phy, DOX, PhD and pPhD NPs, (FIG. 10d) excitated at 488 nm (optimal excitation of DOX) and (FIG. 10e) excitated at 412 nm (optimal excitation of Pa). (FIG. 10f) Near infra-red imaging of 50 µM PhD monomer and its nanoformulation (pPhD NPs). (FIG. 10g) Photothermal effect (temperature increase) and (FIG. 10h) photodynamic effect (ROS production) of 50 µM pPhD NPs measured by a thermal imaging camera and singlet oxygen sensor green (SOSG) as an ROS indicator, respectively. The inset image in g) was captured by a thermal imaging camera. (FIG. 10i) Drug releasing patterns of pPhD NPs (100 µM) at pH 7.4 and pH 5.0 with and without laser irradiation. All laser power was set to 0.4 w/cm$^2$ and the irradiation time was 3 min.

FIG. 11a-i shows in vitro evaluation of pPhD NPs. (FIG. 11a) TEM micrographs illustrated the "Trojan Horse" behaviors of pPhD NPs (50 µM) at pH 6.8. (FIG. 11b) Surface charge changes of the pPhD NPs (50 µM) before/ after PEGylation and de-PEGylation. De-PEGylation was realized by incubated pPhD NPs (10 µM) at pH 6.8. (FIG. 11c) Cell uptake of the pPhD NPs (10 µM) before and after being transformed at pH 6.8. (FIG. 11d) ROS production of the nanoparticles in OSC-3 cancer cells (n=3). The cells were treated with varied materials for 3 h, then applied for light irradiation for 1 min, and stained with DCF-DA for ROS indication. The ROS production was evaluated by flow cytometry. (FIG. 11e) Apoptosis of OSC-3 cells (n=3). The OSC-3 cells were treated with varied materials for 3 h, then applied for light irradiation for 1 min, and stained with Annexin V-FITC and Propidium Iodide (PI) for flow cytometry analysis. In ROS and apoptosis analysis, the concentrations of materials, including photosensitizer, free DOX and nanoparticles, were all set as 10 µM. (FIG. 11f) Cell penetration evaluated on cell spheroids. 20 µM pPhD NPs were incubated with OSC-3 cell spheroids, and observed by CLSM. The scale bar is 100 µm. (FIG. 11g) Lysosomes co-localization illustrated that drug was released in lysosomes. The OSC-3 cells were treated with pPhD NPs (20 µM) for 3 h, then co-stained with Lysotracker Deep Red for CLSM observation. For DOX observation, FITC tunnel was used. For Lysotracker, the Cy5 tunnel was used. The scale bar is 20 µm. (FIG. 11h) Laser-directed phototherapeutic effect on cells, the yellow lighting symbol indicates laser treated area. The live cells were indicated by DIC6(3), the dead cells stained with PI. (i) Cell viabilities of OSC-3 cells by treated with different concentrations of Phy, DOX and pPhD NPs, with or without light irradiation. (FIG. 11j) Combination index (CI) of chemotherapy and phototherapy in pPhD NPs towards OSC-3 cells. The antagonistic effect showed in low concentration was ascribed to the neglectable efficacy of the materials. The concentrations of pPhD NPs were calculated based on PhD monomers, the amounts of PEG were excluded. *p<0.05; , p<0.01; *, p<0.001.

(FIG. 14a) NIRFI images and (FIG. 14b) quantitative fluorescence with statistical analysis of the ex vivo distributions (n=3) of the nanoparticles. (FIG. 14c) Chemical structures illustrated the chelation of the manganese(II) ions (Mn2+) to PhD molecules. (FIG. 14d) Concentration-dependent relaxation of Mn2+ chelated pPhD NPs. The Mn2+ chelated in pPhD NPs were 0.008, 0.016, 0.08, 0.16 and 0.8 mM, respectively. "L" denotes the low concentrations started at 0.008 mM, "H" denotes the high concentrations ended at 0.8 mM. (FIG. 14e) T1-weighted MRI images of time-dependent tumor accumulations (n=3) of the nanoparticles acquired on a 7T MRI scanner and (FIG. 14f) the quantitative MR signal intensity changes (I/I0) on orthotopic oral cancer model. "I" is MR signal at a specific timepoint. "I0" is the MR signal of the mice at "Pre" timepoint. "Pre" denotes the mice before Mn2+ chelated pPhD NPs treatment. (FIG. 14g) Photothermal effects of the nanoparticles on orthotopic oral cancer model (n=6). The laser (680 nm) dose was 0.4 w/cm2 for 3 min. (FIG. 14h) Fluorescence imaging of ROS productions within tumor tissues and (FIG. 14i) quantitative comparisons with statistical analysis of different treatments on orthotopic oral cancer model (n=3). The laser (680 nm) dose was 0.4 w/cm2 for 3 min. The ROS productions were indicated by NIRF ROS probe, CellROX. "Pre" denotes the NIRFI before CellROX treatment; "Post" means the NIRFI after CellROX indication. (j) Phototherapeutic effect monitored by MRI. The laser (680 nm) dose was 0.8 w/cm2 for 3 min. For all animal experiments above, the injection doses of upPhD and pPhD NPs were 10 mg/kg. Phy was 5.3 mg/kg. The concentrations of pPhD NPs were calculated based on PhD monomers, the amounts of PEG were excluded. *, p<0.05; , p<0.01; *, p<0.001.

(FIG. 15c) The tumor volume changes on subcutaneous tumors (n=6) after administration of various treatment groups. The black arrows denote the nanoparticles administration, red ones point out the tumor treated by laser treatments. (FIG. 15d) The complete cure rate (CCR %) of the subcutaneous tumors. (FIG. 15e) The tumor volume changes on orthotopic tumors (n=6). (FIG. 15f) The CCR (%) of the orthotopic tumors treated with different groups. The images showed the tumor profiles of (FIG. 15g) the subcutaneous and (FIG. 15h) the orthotopic models, before ("Pre") and after ("Post") the "pPhD NPs|L" treatments. (FIG. 15i) H&E showed the histological changes induced by the in vivo phototherapeutic effect of photosensitizer-harbored materials. PBS group treated with laser was employed as control. (FIG. 15j) Body weights changes of tumor-bearing mice after treatment. *, p<0.05; , p<0.01; *, p<0.001. Note: the mice were immunodeficient, the light treatments on right tumor were not able to induce immuno-responses to affect the left tumor.

FIG. 16c) Cryo-electron microscopy images of PI NPs and RBC-PI (1:1); and FIG. 16d) various RBC vesicles-to-PI ratios (2:1, 4:1) and RBC vesicles. Arrows indicated RBC bi-layered cell membrane. Scale bar=50 nm; FIG. 16e) SDS-PAGE protein analysis of RBCs, RBC vesicles, RBC-PI (1:1) and PI NPs.

FIG. 17d) ROS generation of RBC-PI with various RBC vesicles-to-PI with different ratios upon irradiation (680 nm at 0.8 W/cm$^2$ for 3 min); FIG. 17e) Quantitative temperature increases of RBC-PI with various RBC vesicles-to-PI ratios, PI NPs and RBC upon illumination (680, 0.8 W/cm$^2$, 3 min); FIG. 17f) Stability test of RBC-PI (RBC vesicles-to-PI ratio: 1:1) in the presence of 10% FBS/PBS under 37° C. for 30 days. Size and PDI were measured by DLS.

FIG. 19a) cell uptake and FIG. 19b) intracellular ROS production of PI and RBC-PI with and without light treatment assessed with flow cytometry with 2',7'-dichlorofluorescin diacetate (DCF-DA) as a ROS indicator (**P<0.01); FIG. 19c) Light triggered drug release under pH 7.4 and 5.4 (mimicking lysosome pH). L: (0.8 W/cm$^2$ for 3 min); H: (1.6 W/cm$^2$ for 3 min); FIG. 19d) Self-indication of cellular behaviors and time-dependent drug release of RBC-PI (25 μM). Red: free Pa molecules or dissociated PI, Blue: cleaved Ir. Bar=50 μm.

FIG. 20b) Intracellular uptake of RBC-PI and PI NPs by U937 human macrophage cells after 2, 4 and 8 h of incubation. (***P<0.0001).

FIG. 21e) Tumor surface temperatures at each different time point and group were monitored using NIR thermal camera; FIG. 21f) Biodistribution of PI and RBC-PI at 48 h after the injection. (*P<0.05, P<0.01, *P<0.001); FIG. 21g) Histopathological evaluations of A549 tumors upon PBS, Pa—Ir, PI NPs and RBC-PI mediated photochemotherapy, bar=60 μm.

DETAILED DESCRIPTION OF THE INVENTION

I. General

Figure 1:
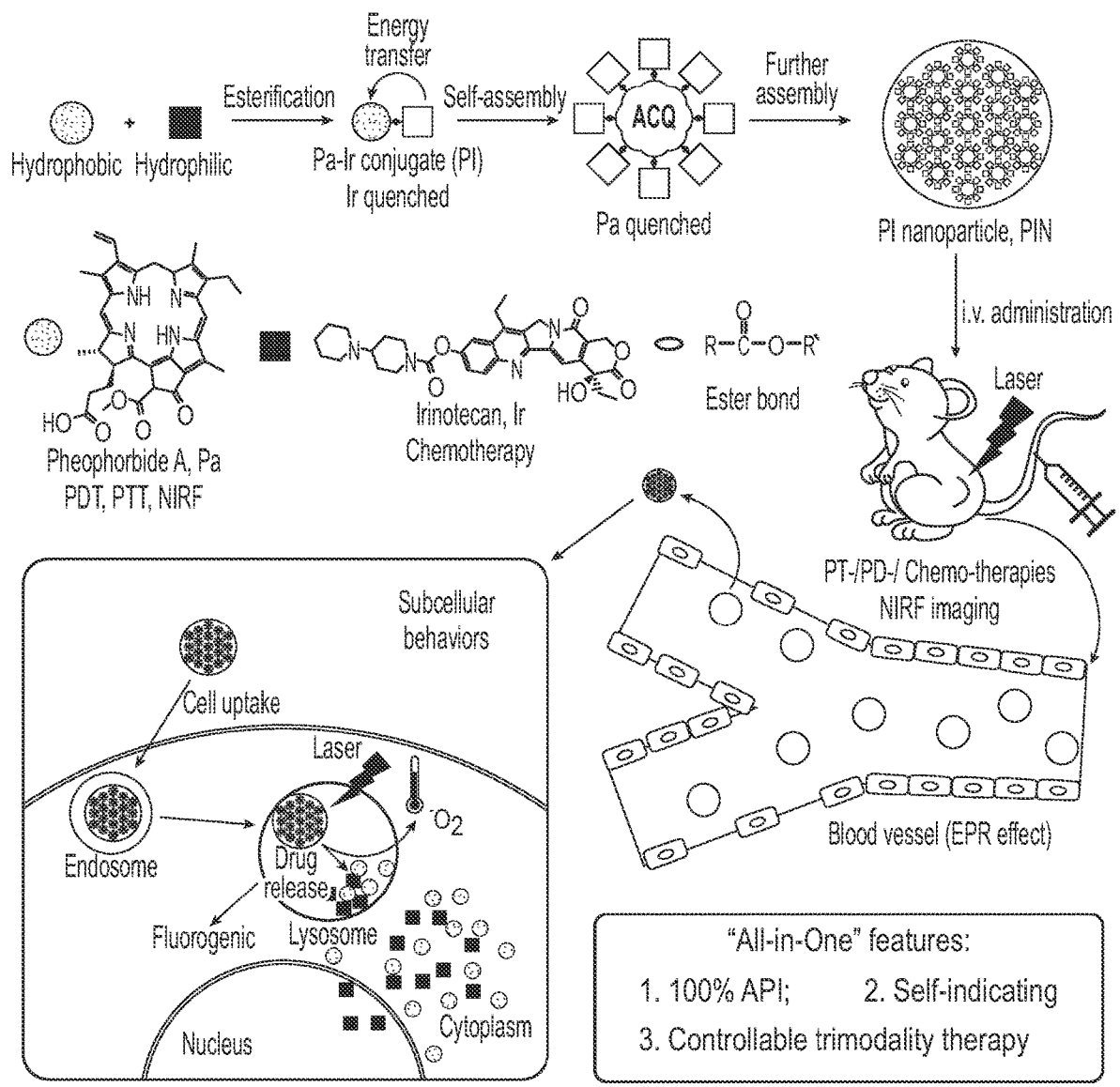
FIG. 1 shows two fluorescent APIs (pheophorbide A, Pa and irinotecan, Ir) were conjugated through an ester bond, and forming an amphiphilic molecule, Pa—Ir conjugate (PI). In PI, the fluorescence of Ir was quenched because of the energy transfer from Ir to Pa. The PI molecules were then self-assembled into PI nanoparticles (PIN), the fluorescence of Pa was quenched along with the nanostructure formation, due to the aggregation caused quenching (ACQ) behaviours. The dual-fluorescence inactivation of Pa and Ir can give rise to a dual-fluorogenic process if specific stimuli broke the energy transfer in PIN. The dual-fluorogenic of PIN achieved to spatiotemporally indicate the subcellular distributions and drug releasing process in real time. PIN was then i.v. administrated into tumour bearing mice, and preferentially accumulated in tumour regions through enhanced permeability and retention (EPR) effect; after accumulation in tumour regions, PIN was ingested by cells and transported to lysosomes. Under the assistances of acidic pH and laser power, PIN released Pa and Ir, consequently broke the energy transfer and ACQ relationships, thus realized a dual-fluorogenic process. Meanwhile, controllable trimodality therapy (photodynamic-, photothermal- and chemo-therapies) and NIRF imaging can be activated when laser beam pointed to the nanoparticles, at both in vitro and in vivo levels. Abbreviations: PDT, photodynamic therapy; PTT, photothermal therapy; NIRF, near infrared fluorescence; 1O2, reactive oxygen species.

The present invention provides a series of amphiphilic conjugates of a first active pharmaceutical ingredient, and either a second active pharmaceutical ingredient or a photoactive compound, such as a porphyrin or derivative thereof. The amphiphilic conjugates self-assemble to form nanoparticles, which aggregate to form nanocarriers. The nanoparticles and nanocarriers are absorbed by the cancer cells, or other cells to be treated, thus simultaneously deliver two active anti-cancer agents to the cancer cells. Administering the conjugates to treat a disease or condition in a subject allows administration at doses that are lower than the FDA approved dosage for administration of either therapeutic agent alone.

II. Definitions

"Partition coefficient" or "logP" refers to the relative ratio of the concentrations of a compound or substance in two immiscible liquids, such as an aqueous solvent (water) and a non-polar solvent (often octanol). When the immiscible liquids are water and octanol, the larger the logP value indicates a more hydrophobic compound. logP is calculated according to the following equation:

$$\log P \; oct/water = \log\left(\frac{[solute]octanol}{[solute]water}\right)$$

Hydrophilic compounds useful in the present invention typically have a logP value of less than about 2, and hydrophobic compounds useful in the present invention typically have a logP value of at least 2.

"Hydrophilic therapeutic agent" refers to compounds useful to treat a disease or condition that are generally considered to be hydrophilic, and have a logP value of less than about 2. Representative hydrophilic therapeutic agents include doxorubicin hydrochloride, daunorubicin hydrochloride, idarubicin hydrochloride, irinotecan hydrochloride, topotecan hydrochloride, camptothecin, analogs thereof, etc.

"Hydrophobic compound" refers to compounds that are generally considered to be hydrophobic, and have a logP value of at least 2. Representative hydrophobic compounds include hydrophobic therapeutic compounds that are useful for treating a disease or condition, such as porphyrins, paclitaxel, docetaxel, cabazitaxel, vincristine, vinblastine, and others.

"Amphiphilic" refers to a compound having both hydrophilic and hydrophobic properties. The conjugates of the present invention, having both a hydrophilic component and a hydrophobic component are amphiphilic in nature.

"Linker" refers to a divalent compound covalently connecting two separate compounds together. The linker can be cleavable under certain environmental conditions, such as temperature or pH, or be cleavable enzymatically or under other reaction conditions. Alternatively, the linker can be non-cleavable.

"Photo-active compound" refers to compounds capable of responding to electromagnetic radiation by emitting electromagnetic radiation, transferring the energy to another molecule, or generating a new species such as an oxygen radical, singlet oxygen, other reactive oxygen species, or other species. Representative photo-active compounds for use in the present invention include porphyrins, corrins, chlorins, bacteriochlorophyll, corphins, corroles, porphycenes, etc.

"Anti-cancer agent" refers to any agent capable of treating or ameliorating a cancer. Representative anti-cancer agents useful in the present invention include, but are not limited to, paclitaxel, docetaxel, cabazitaxel, vincristine, vinblastine, and others "Cis-diol" refers to a compound containing two hydroxy groups on adjacent carbons that are oriented in the same direction. Representative cis-diols for use in the present invention include, but are not limited to, sugars, adenosine, azacitidine, capecitabine, doxifluridine, sialic acid, dopamine, and others.

"Metal" refers to elements of the periodic table that are metallic and that can be neutral, or negatively or positively charged as a result of having more or fewer electrons in the valence shell than is present for the neutral metallic element. Metals useful in the present invention include the alkali metals, alkali earth metals, transition metals and post-transition metals. Alkali metals include Li, Na, K, Rb and Cs. Alkaline earth metals include Be, Mg, Ca, Sr and Ba. Transition metals include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. Post-transition metals include Al, Ga, In, Tl, Ge, Sn, Pb, Sb, Bi, and Po. Rare earth metals include Sc, Y, La, Ce, Pr, Nd, Sm, Eu, Gd, Tb, Dy, Ho, Er, Tm, Yb and Lu. One of skill in the art will appreciate that the metals described above can each adopt several different oxidation states, all of which are useful in the present invention. In some instances, the most stable oxidation state is formed, but other oxidation states are useful in the present invention.

"Nanoparticle" refers to a micelle resulting from aggregation of the amphiphilic conjugates of the invention. The nanoparticle has an interior and an exterior. The nanoparticles further aggregate to form nanocarriers.

"Stabilizing polymer" refers to a hydrophilic polymer capable of stabilizing the nanoparticles and resulting nanocarriers. Representative stabilizing polymer can be polyethylene glycol.

"Cell membrane" refers to a lipid bilayer that protects the cell from its environment. Some cell membranes, such as those from a red blood cell, can form independent vesicles for use as delivery vehicles (red blood cell vesicle).

"Targeting ligand" refers to antibodies, peptides, and other biological agents capable of targeting a specific cell, tissue, organ, or location within a body.

"Forming a reaction mixture" refers to the process of bringing into contact at least two distinct species such that they mix together and can react, either modifying one of the initial reactants or forming a third, distinct, species, a product. It should be appreciated, however, the resulting reaction product can be produced directly from a reaction between the added reagents or from an intermediate from one or more of the added reagents which can be produced in the reaction mixture.

"Treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

"Subject" refers to animals such as mammals, including, but not limited to, primates (e.g., humans), cows, sheep, goats, horses, dogs, cats, rabbits, rats, mice and the like. In certain embodiments, the subject is a human.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of*

*Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

"Photodynamic therapy" refers to use of nontoxic, light-sensitive compounds that become toxic to malignant or disease cells upon exposure to light. Photodynamic therapy involves a photosensitizer, a light source, and oxygen. Upon exposure to the light, the photosensitizer generates reactive oxygen species (singlet oxygen, an oxygen free radical) that react with and destroy the malignant tissue. A variety of photosensitizers can be used, including porphyrins, chlorophylls and dyes.

"Photothermal therapy" refers to use of nontoxic, light-sensitive compounds that generate heat upon exposure to light. Like photodynamic therapy, photothermal therapy involves a photosensitizer and a source of light, typically infrared. But photothermal therapy does not require oxygen. A variety of photosensitizers can be used, including porphyrins, chlorophylls and dyes.

"An effective amount of electromagnetic radiation" refers to an amount of electromagnetic radiation (i.e., visible, ultraviolet, or infrared) light that is effective to treat a disease or condition. The effective amount can be an amount effective to interact with a photo-active compound and cause heating, singlet oxygen generation, peroxide or hydroxyl radical generation, or direct energy or electron transfer from the photosensitizer to cellular and/or extracellular components and thereby induce treatment (e.g., cell death).

III. Conjugates

The present invention provides a series of amphiphilic conjugates of a first active pharmaceutical ingredient, and either a second active pharmaceutical ingredient or a photo-active compound. The amphiphilic conjugates self-assemble to form nanoparticles, which aggregate to form nanocarriers. The nanoparticles and nanocarriers are absorbed by the cancer cells, or other cells to be treated, thus simultaneously deliver two active anti-cancer agents to the cancer cells. Conjugates not encompassed by the present invention include (1) doxorubicin directly linked to 10-hydroxycamptothecin, and (2) irinotecan directly linked to chlorambucil.

In some embodiments, the present invention provides a compound of Formula I:

X-(L)-Y wherein X is a hydrophilic therapeutic agent, L is absent or is a linker, and Y is a photo-active compound comprising a porphyrin or analog thereof, or a hydrophobic therapeutic agent, where the compound is other than doxorubicin-10-hydroxycamptothecin and irinotecan-chlorambucil.

The compounds of the present invention are amphiphilic compounds. For example, the hydrophilic therapeutic agent X can have a log P value of less than 2.0, or less than 1.9, 1.8, 1.7, 1.6, 1.5, 1.4, 1.3, 1.2, 1.1, 1.0, 0.5, or less than 0.0. The group Y can have a log P value of at least 2.0, or at least 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or at least 4.5, or greater. Moreover, the difference of the log P values for X and Y is at least 1.0, or at least 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or at least 3.0, or greater.

In some embodiments, the compound of Formula I is amphiphilic. In some embodiments, X has a logP value of less than 2.0, and Y has a logP value of at least 2.0, wherein the difference of the logP values for X and Y is at least 1.0. In some embodiments, X has a log P value of less than 1.7, and Y has a log P value of greater than 2.5, wherein the difference of the logP values for X and Y is at least 1.0. In some embodiments, X has a log P value of less than 1.7, and Y has a log P value of greater than 3.0. In some embodiments, X has a log P value of less than 1.7, and Y has a log P value of greater than 3.0, wherein the difference of the logP values for X and Y is at least 1.5. In some embodiments, X has a log P value of less than 1.7, and Y has a log P value of greater than 3.5. In some embodiments, the difference of the logP values for X and Y is at least 2.0. In some embodiments, X has a log P value of less than 1.7, and Y has a log P value of greater than 3.5, wherein the difference of the logP values for X and Y is at least 2.0

The conjugates of the present invention include a hydrophilic therapeutic agent having a log P value of less than about 2. Hydrophilic therapeutic agents include any agent capable of treating or ameliorating a disease or condition, where the hydrophilic therapeutic agent has a log P value of less than about 2.

Representative diseases or conditions that can be treated by the hydrophilic therapeutic agent include hyperproliferative disorders including cancer. Other diseases that can be treated by the hydrophilic therapeutic agent of the present invention include: (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome). In addition, the hydrophilic therapeutic agent of the present invention can be useful for the treatment of infection by pathogens such as viruses, bacteria, fungi, and parasites. Other hydrophilic therapeutic agents are useful in the present invention.

Representative hydrophilic therapeutic agents include anti-cancer agents. In some embodiments, the hydrophilic therapeutic agent is an anti-cancer agent. Anti-cancer agents useful in the present invention include, but are not limited to, doxorubicin, daunorubicin, idarubicin, epirubicin, bleomycin, topotecan, irinotecan, camptothecin, and salts thereof. In some embodiments, the hydrophilic therapeutic agent is doxorubicin, daunorubicin, idarubicin, epirubicin, bleomycin, topotecan, irinotecan, or camptothecin, or salts thereof. In some embodiments, the hydrophilic therapeutic agent is doxorubicin, daunorubicin, idarubicin, topotecan, irinotecan, or camptothecin, or salts thereof. In some embodiments, the hydrophilic therapeutic agent is doxorubicin hydrochloride, daunorubicin hydrochloride, idarubicin hydrochloride, epirubicin hydrochloride, bleomycin hydrochloride, topotecan hydrochloride, irinotecan hydrochloride, or camptothecin. In some embodiments, the hydrophilic therapeutic agent is doxorubicin hydrochloride.

Other hydrophilic therapeutic agents include compounds having a cis-diol functional group. Representative cis-diols include sugars, sugar-containing compounds such as nucleosides and nucleotides, as well as other compounds having a 1,2-diol or a 1,3-diol. In some embodiments, the hydrophilic therapeutic agent is a cis-diol. In some embodiments, the hydrophilic therapeutic agent is curcumin, mannitol, fructose, glucose, adenosine, azacitidine, capecitabine, doxifluridine, sialic acid, or dopamine. In some embodiments, the hydrophilic therapeutic agent is curcumin, mannitol, fructose, glucose, adenosine, azacitidine, sialic acid, or dopamine.

The hydrophilic therapeutic agent X and the group Y can be linked directly to one another or via a linker L. The linker linker L can be a cleavable linker or a non-cleavable linker. In some embodiments, linker L is absent. In some embodiments, L comprises the linker. When the linker is a cleavable linker, the linker can be responsive to pH, enzymatic cleavage, redox conditions, temperature, and other conditions. In some embodiments, the linker L comprises a pH-responsive linker, an enzyme-cleavable peptide, a redox responsive linker (disulfide bond) or cis-diol/pH responsive. In some embodiments, the linker L is hydrazone, ester, orthoester, imine, cis-aconityl, acetal, ketal, MMP-2, MMP-9, Caspase-3, Caspase-9, Cathepsin B, a disulfide, or a boronic ester. In some embodiments, the linker L is hydrazone. In some embodiments, the linker L is a boronic ester.

A. Drug-Drug Conjugates

In some embodiments, group Y can be a hydrophobic therapeutic agent. Representative hydrophobic therapeutic agents useful in the present invention include therapeutic agents having a log P of at least 2.0, or at least 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or at least 4.5, or greater. In some embodiments, the hydrophobic therapeutic agent can have a log P value of at least 2.5. In some embodiments, the hydrophobic therapeutic agent can have a log P value of at least 3.0. In some embodiments, the hydrophobic therapeutic agent can have a log P value of at least 3.5. In some embodiments, the hydrophobic therapeutic agent can have a log P value of at least 4.0.

Representative diseases or conditions that can be treated by the hydrophobic therapeutic agent include hyperproliferative disorders including cancer. Other diseases that can be treated by the hydrophobic therapeutic agent of the present invention include: (I) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome). In addition, the hydrophobic therapeutic agent of the present invention can be useful for the treatment of infection by pathogens such as viruses, bacteria, fungi, and parasites. Other hydrophobic therapeutic agents are useful in the present invention.

The hydrophobic therapeutic agent and the hydrophilic therapeutic agent can be selected to treat the same or different diseases. For example, the hydrophobic therapeutic agent can be selected to treat a cancer, and the hydrophilic therapeutic agent can be selected to treat a different disease. Moreover, the hydrophilic therapeutic agent can be selected to treat a cancer, and the hydrophobic therapeutic agent can be selected to treat a different disease. Alternatively, the hydrophobic therapeutic agent and the hydrophilic therapeutic agent can be selected to treat the same disease, such as cancer.

In some embodiments, the hydrophobic therapeutic agent is bortezomib, paclitaxel, docetaxel, cabazitaxel, vincristine, vinblastine, camptothecin, capecitabine, crizotinib, or ribociclib. In some embodiments, X is curcumin and Y is bortexomib, or X is doxorubicin and Y is cabazitaxel, or X is doxorubicin and Y is docetaxel, or X is doxorubicin and Y is paclitaxel, or X is doxorubicin and Y is vinblastine, or X is doxorubicin and Y is vincristine. In some embodiments. X is curcumin and Y is bortexomib, or X is doxorubicin hydrochloride and Y is cabazitaxel, or X is doxorubicin hydrochloride and Y is docetaxel, or X is doxorubicin hydrochloride and Y is paclitaxel, or X is doxorubicin hydrochloride and Y is vinblastine, or X is doxorubicin hydrochloride and Y is vincristine. In some embodiments, the compound of Formula I has the structure of:

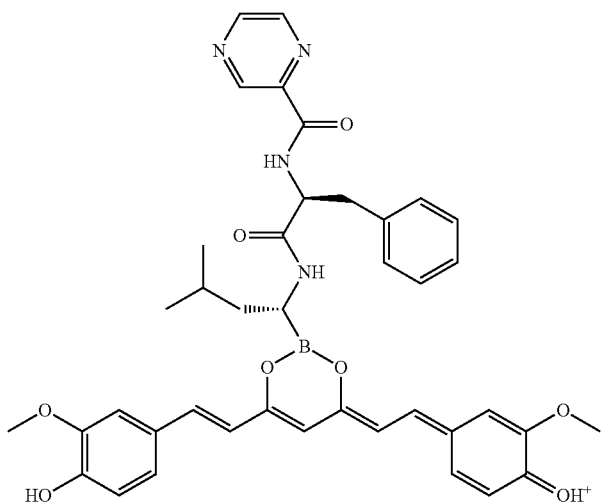
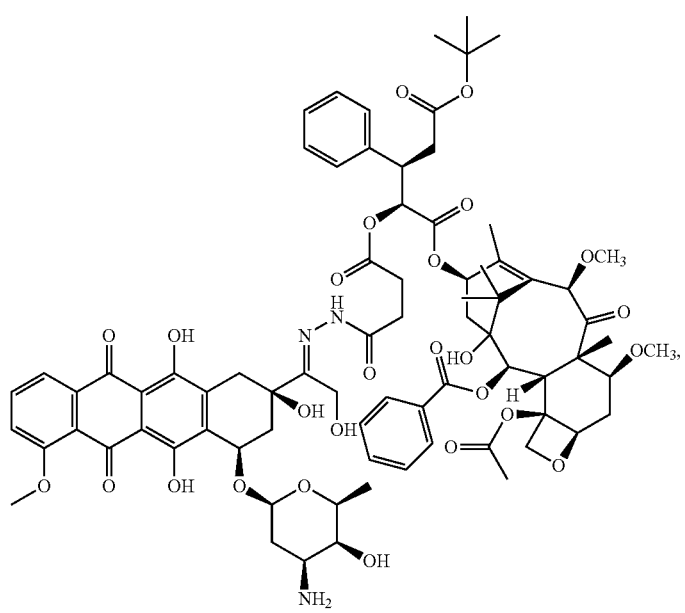
Doxorubicin-Cabazitaxel Amphiphilic Conjugate

-continued
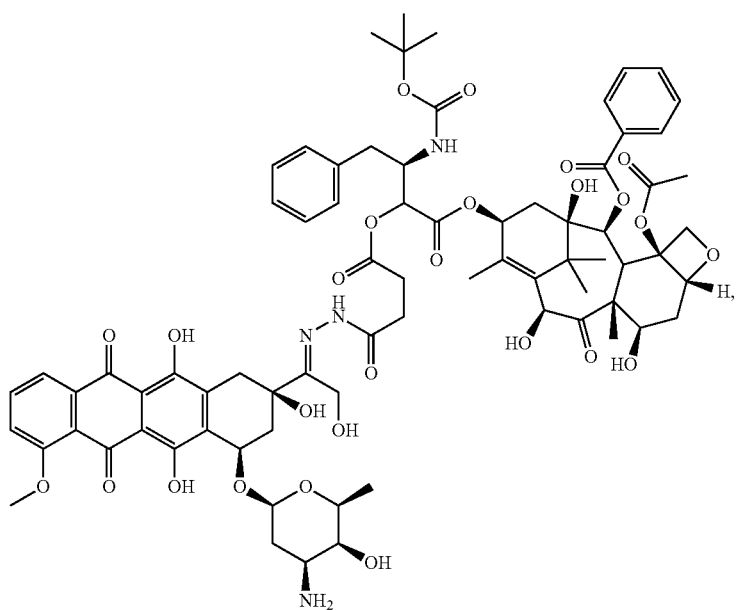
Doxorubicin-Docetaxel Amphiphilic Conjugate
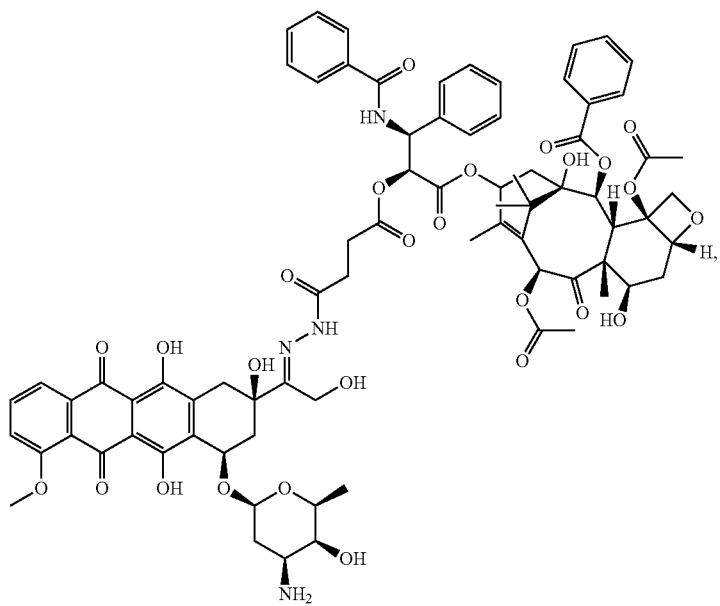
Doxorubicin-Paclitaxel Amphiphilic Conjugate

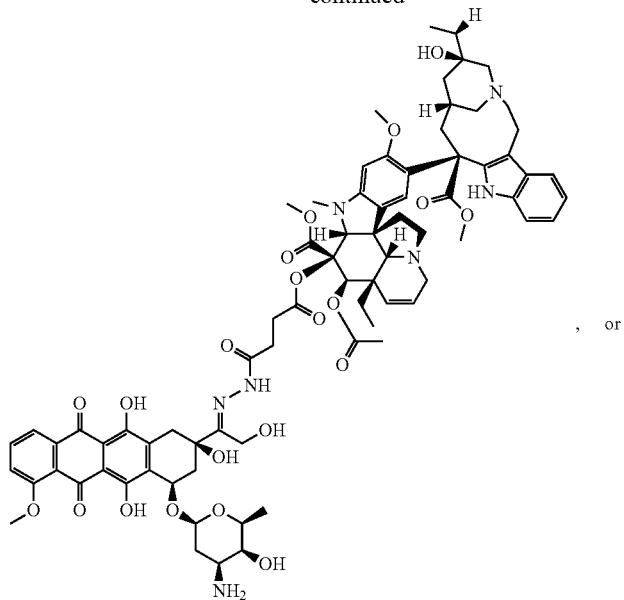

Doxorubicin-Vinblastine Amphiphilic Conjugate

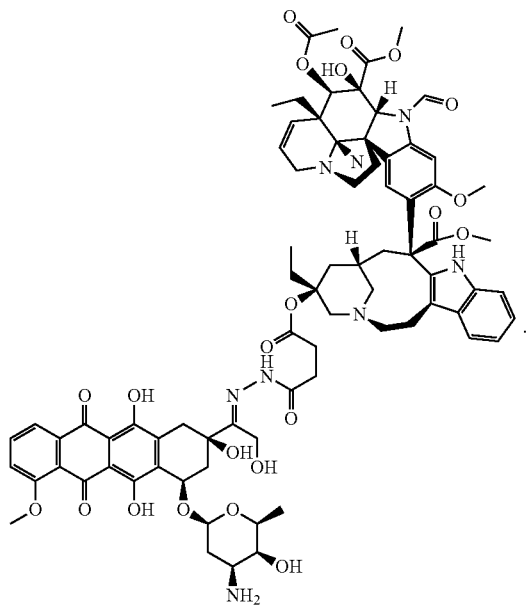

Doxorubicin-Vincristine Amphiphilic Conjugate

B. Porphyrin-Drug Conjugates

In some embodiments, the Y group is the photo-active compound. Photo-active compounds useful in the present invention include, but are not limited to, a porphyrin, a benzoporphyrin, a corrin, a chlorin, a bacteriochlorophyll, a corphin, or derivatives thereof.

In some embodiments, the photo-active compound is a porphyrin, a benzoporphyrin, a corrin, a chlorin, a bacteriochlorophyll, a corphin, or derivatives thereof. Any suitable porphyrin can be used in the compounds of the present invention. Representative porphyrins suitable in the present invention include, but are not limited to, pyropheophorbide-a, pheophorbide, chlorin e6, purpurin or purpurinimide. In some embodiments, the porphyrin can be pheophorbide-a. In some embodiments, the porphyrin can be pyropheophorbide-a. Representative photo-active compounds are shown below:

| PHOTO-ACTIVE COMPOUND | STRUCTURE |
| --- | --- |
| Porphyrin | 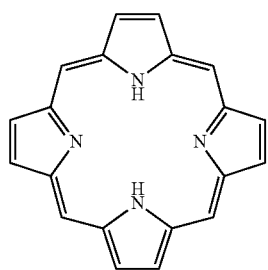 [SMILES: C1=Cc2cc3ccc(cc4nc(cc5ccc(cc1n2)[nH]5)C=C4)[nH]3] |
| Pyropheophorbide-a | 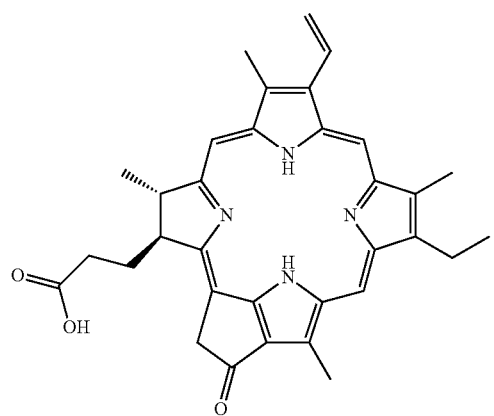 [SMILES: C=Cc1c(C)c2cc3nc(c4c5[nH]c(cc6nc(cc1[nH]2)C(C)=C6CC)c(C)c5C(=O)C4)[C@@H](CCC(=O)O)[C@@H]3C] |
| Pheophorbide | 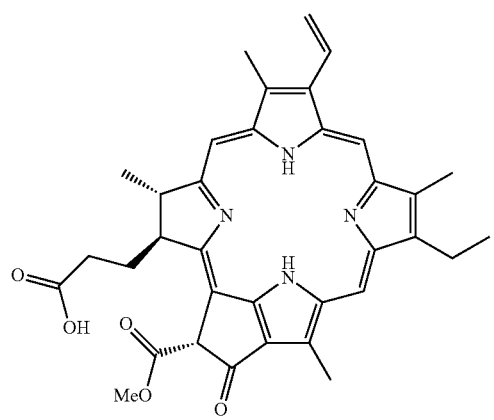 [SMILES: C=Cc1c(C)c2cc3nc(c4c5[nH]c(cc6nc(cc1[nH]2)C(C)=C6CC)c(C)c5C(=O)[C@@H]4C(=O)OC)[C@@H](CCC(=O)O)[C@@H]3C] |
| Chlorin e6 | 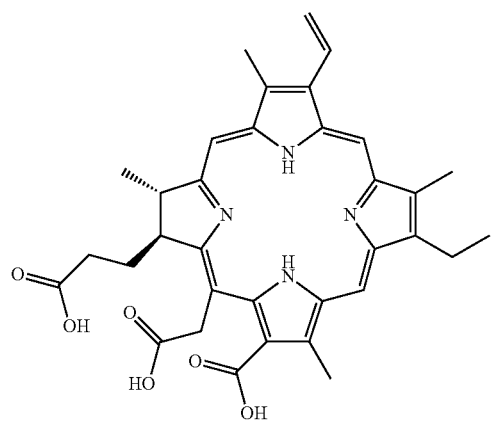 [SMILES: C=Cc1c(C)c2cc3nc(c(CC(=O)O)c4[nH]c(cc5nc(cc1[nH]2)C(C)=C5CC)c(C)c4C(=O)O)[C@@H](CCC(=O)O)[C@@H]3C] |

-continued

| PHOTO-ACTIVE COMPOUND | STRUCTURE |
| --- | --- |
| Purpurin | 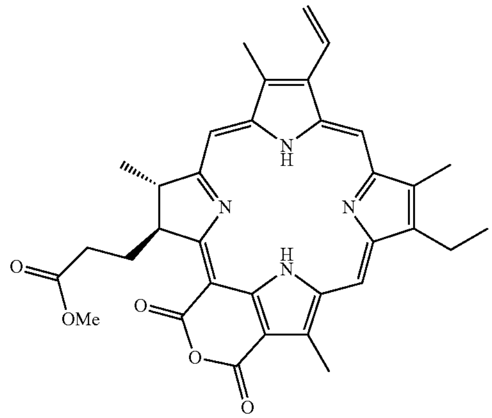 |
| Purpurinimide | 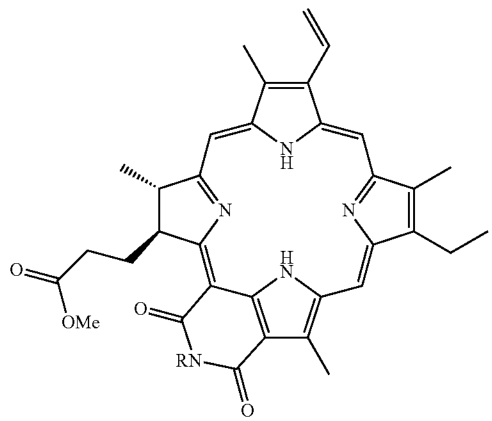 [SMILES: C=Cc1c(C)c2cc3nc(c4c5[nH]c(cc6nc(cc1[nH]2)C(C)=C6CC)c(C)c5C(=O)OC4=O)[C@@H](CCC(=O)OC)[C@@H]3C] |
| Corrin | 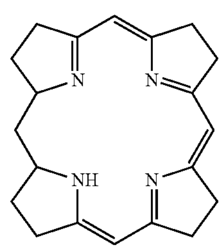 [SMILES: C1=C2/CCC(=N2)/C=C2/CCC(CC3CCC(=N3)/C=C3/CCC/1=N3)N2] |
| Chlorin | 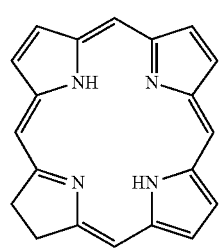 [SMILES: C1=Cc2cc3ccc(cc4nc(cc5ccc(cc1n2)[nH]5)CC4)[nH]3] |
| Corphin | 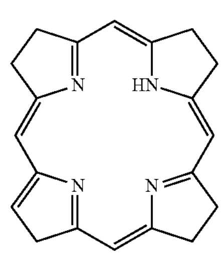 [SMILES: C1=C2/C=C3/CCC(=N3)/C=C3/CC/C(=C/C4=NC(=C\C(=N2)C1)/CC4)N3] |

In some embodiments, the photo-active compound is porphyrin, pyropheophorbide-a, pheophorbide, chlorin e6, purpurin, purpurinimide, verteporfin, photofrin porfimer, rostaporfin, talporfin, or temoporfin. In some embodiments, the photo-active compound is pyropheophorbide-a. In some embodiments, the photo-active compound is pheophorbide-a. In some embodiments, the photo-active compound is porphyrin.

In some embodiments, the compound can be X is irinotecan and Y is pyropheophorbide A, or X is doxorubicin and Y is pyropheophorbide A, or X is daunorubicin and Y is pyropheophorbide A, or X is idarubicin and Y is pyropheophorbide A, or X is topotecan and Y is pyropheophorbide A. In some embodiments, the compound X is doxorubicin and Y is pyropheophorbide A.

In some embodiments, the compound can be X is irinotecan and Y is pheophorbide A, or X is doxorubicin and Y is pheophorbide A, or X is daunorubicin and Y is pheophorbide A, or X is idarubicin and Y is pheophorbide A, or X is topotecan and Y is pheophorbide A. In some embodiments, the compound X is doxorubicin and Y is pheophorbide A.

In some embodiments, the compound has the structure:

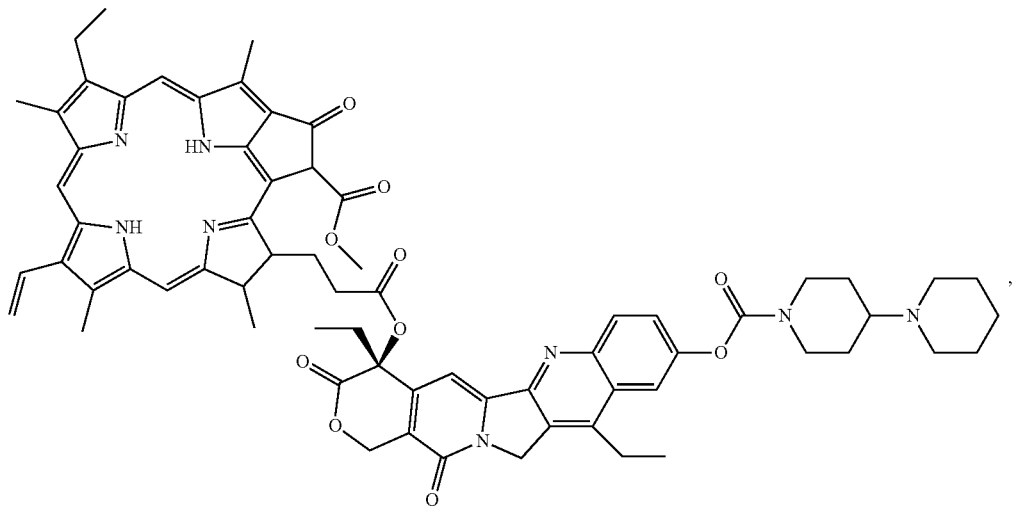

Pa-Ir Conjugate, P1

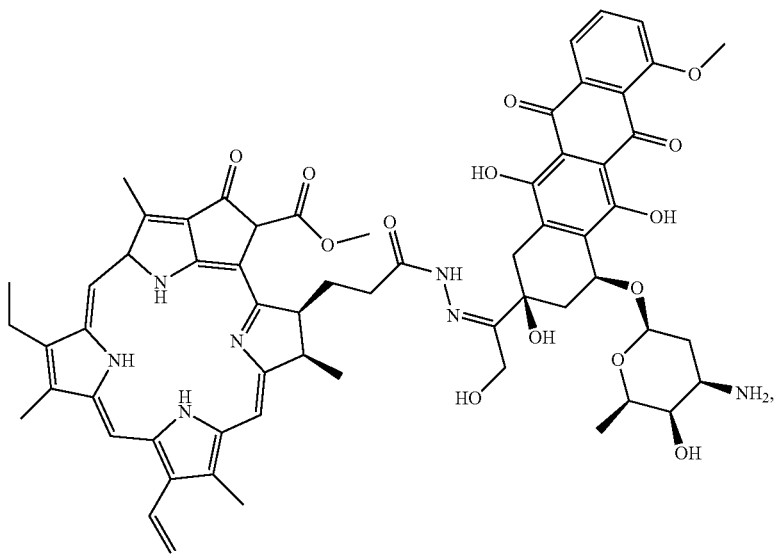

Porphyrin-Doxorubicin Amphiphilic Conjugate

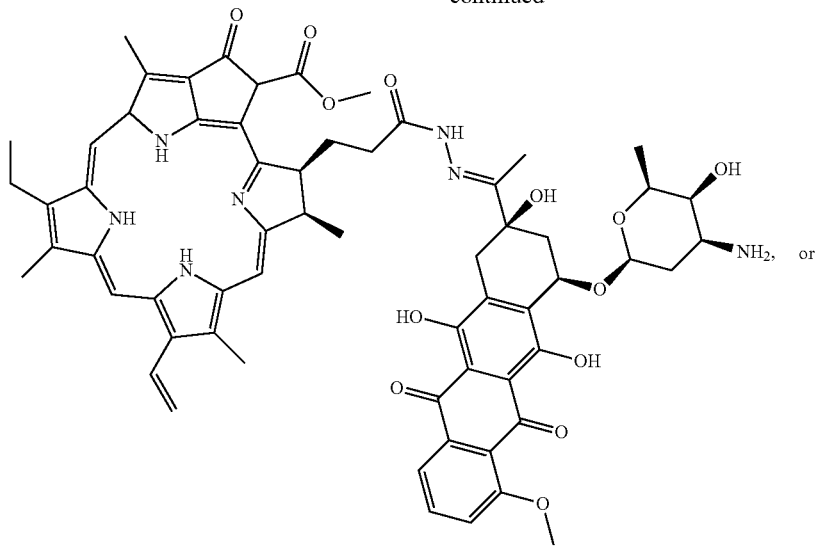

Porphyrin-Daunorubicin Amphiphilic Conjugate

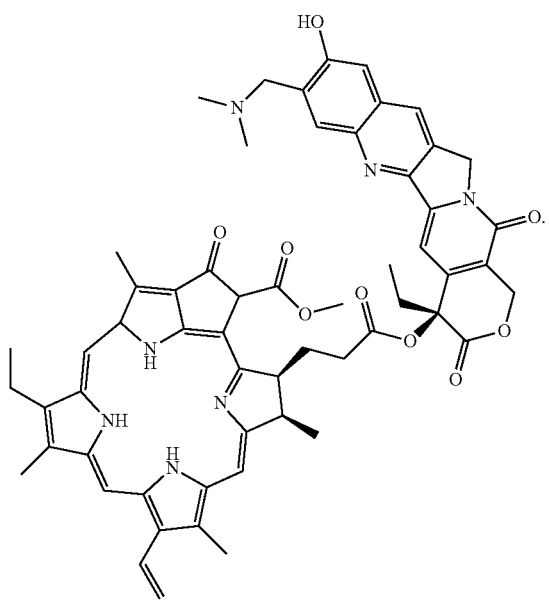

Porphyrin-Topotecan Amphiphilic Conjugate

The photo-active compounds of the present invention can also be chelated to a metal ion. Representative metals useful in the present invention include transition metals, post-transition metals and rare earth metals. In some embodiments, the conjugate of Formula I includes a metal chatted by the photo-active compound. In some embodiments, the metal can be Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg or Ac. In some embodiments, the metal can be Sc, Ti, V, Cr, Mn, Fe, Co, Ni, Cu, Zn, Mo, Ru, W, Re, or Os. In some embodiments, the metal can be Mn.

One of skill in the art will appreciate that the metals described above can each adopt one or more different oxidation states. For example, the metal can have the oxidation state of +1, +2, +3, +4, +5, +6, +7, or +8. In some embodiments, the metal can have the oxidation state +2. In some embodiments, the metal can be $Mn^{2+}$.

In some embodiments, the compound has the structure of:

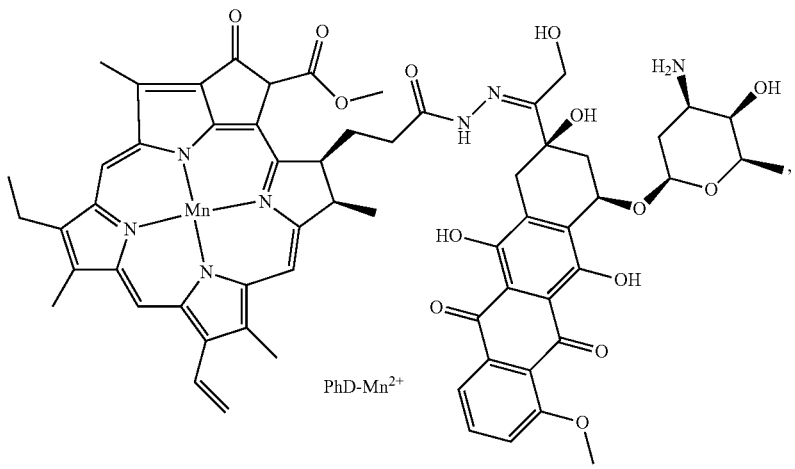

PhD-Mn²⁺

IV. Nanoparticles

The amphiphilic conjugates of the present invention self-assemble to form nanoparticles having an interior and an exterior where the hydrophobic portion of the conjugate is in the interior and the hydrophilic portion of the conjugate is on the exterior of the nanoparticle. In some embodiments, the present invention provides a nanoparticle having a plurality of conjugates of the present invention, wherein the nanoparticle comprises an interior and an exterior.

The exterior of the nanoparticles can be modified with a variety of groups, such as targeting ligands, stabilizing polymers, cell membranes, drugs, etc. In some embodiments, the exterior of the nanoparticle includes at least one of a stabilizing polymer, a cell membrane or a targeting ligand.

The stabilizing polymer can be any polymer that stabilizes the nanoparticle. Representative stabilizing polymers include hydrophilic polymers having polar groups or charged groups that make the polymers substantially soluble in water. The stabilizing polymers can be the same or different, and can include polyethylene glycol, poly(N-isopropylacrylamide), polyacrylamide, poly(2-oxazoline), polyethylenimine, poly(acrylic acid), polymethacrylate and other acrylate-based polymers, poly(vinyl alcohol), poly(vinylpyrrolidone), hyaluronic acid and derivatives and copolymers thereof. In some embodiments, the stabilizing polymer can be polyethyleneglycol. In some embodiments, the stabilizing polymer can be hyaluroinc acid.

The stabilizing polymers can be of any suitable molecular weight. Molecular weight of a polymer can be measured as the number average ($M_n$) molecular weight, the weight average ($M_w$) molecular weight, or Z-average molecular weight ($M_z$). For example, the stabilizing polymer can have a molecular weight from 500 Da to 10,000 Da, or from 1000 Da to 5000 Da. Representative molecular weights of the stabilizing polymer can be about 500 Da, or about 1000, 1500, 2000, 2500, 3000, 3500, 4000, 4500, 5000, 6000, 7000, 8000, 9000, or about 10,000 Da. In some embodiments, the molecular weight of the stabilizing polymer can be from 1000 Da to 5000 Da. In some embodiments, the molecular weight of the stabilizing polymer can be about 2000 Da. In some embodiments, the stabilizing polymer can be polyethyleneglycol with a molecular weight of about 2000 Da.

The nanoparticles can also include a cell membrane encompassing the nanoparticle. Representative cell membranes include red blood cells (RBCS), white blood cells, platelets, cancer cells, stem cells and other cell types from specific organs. In some embodiments, the cell membrane is a red blood cell membrane.

Any suitable ratio of the cell membrane to the nanoparticle or conjugate can be used. For example, the ratio of the cell membrane to the nanoparticle or conjugate can be from 0.1:1 (w/w) to 10:1 (w; w), from 0.5:1 (w/w) to 10:1 (w/w), from 1:1 (w/w) to 10:1 (w/w), from 1:1 (w/w) to 5:1 (w/w), or from 1:1 (w/w) to 4:1 (w/w). The ratio of the cell membrane to the nanoparticle or conjugate can be about 1:1 (w/w), about 1.5:1 (w/w), about 2:1 (w/w), about 2.5:1 (w/w), about 3:1 (w/w), about 3.5:1 (w/w), about 4:1 (w/w), about 4.5:1 (w/w), or about 5:1 (w/w). In some embodiments, the ratio of the cell membrane to the conjugate can be from 1:1 (w/w) to 10:1 (w/w). In some embodiments, the ratio of the cell membrane to the conjugate can be from 1:1 (w/w) to 5:1 (w/w). In some embodiments, the ratio of the cell membrane to the conjugate can be about 1:1 (w/w). In some embodiments, the ratio of the cell membrane to the conjugate can be about 2:1 (w/w). In some embodiments, the ratio of the cell membrane to the conjugate can be about 4:1 (w/w).

Targeting ligands useful in the present invention include, but are not limited to aptamers, avimer scaffolds based on human A domain scaffolds, diabodies, camelids, shark IgNAR antibodies, fibronectin type III scaffolds with modified specificities, antibodies, antibody fragments, vitamins and cofactors, polysaccharides, carbohydrates, steroids, proteins, peptides, polypeptides, nucleotides, oligonucleotides, polynucleotides, and nucleic acids (e.g., mRNA, tRNA, snRNA, RNAi, microRNA, DNA, cDNA, antisense constructs, ribozymes, etc, and combinations thereof). In some embodiments, the targeting ligand can include an antibody. In some embodiments, the bioactive agent can be a peptide sequence that binds non-specifically or specifically.

The exterior of the nanoparticle can also be modified with a variety of other groups that can be recognized or targeted by biological systems or mechanisms in the subject, or improve stability of the nanoparticle. In some embodiments, the exterior of the nanoparticle comprises at least one of polyethylene glycol, hyaluronic acid, a cell membrane, RGD, CRGDK, folic acid, or galactose. In some embodiments, the exterior includes polyethylene glycol. In some embodiments, the exterior includes a red blood cell vesicle.

The nanoparticles of the present invention can self-assemble to form a hydrophobic interior and a hydrophilic exterior. In some embodiments, the nanoparticles include a plurality of nanoparticles self-assemble to form a nanocarrier.

The stability of the nanoparticles can be further improved by cross-linking the nanoparticles. The cross-linking of the nanoparticles can be via covalent or ionic bond formation. The cross-linking can be permanent or reversible. Representative bonds formed upon cross-linking include, but are not limited to, disulfide, ester, amide, boronate ester, uread, carbamate, etc.

The nanoparticles can be prepared by a variety of methods, including self-assembly. For example, the conjugates of the present invention can be dissolved in a suitable solvent at a suitable concentration and sonicated for a suitable period of time to form the nanoparticles. In some embodiments, the present invention provides a method of preparing a nanoparticle of the present invention, comprising forming a reaction mixture including a plurality of conjugates of the present invention, under conditions suitable for the plurality of conjugates to self-assemble and form nanoparticles.

V. Methods of Treating

The present invention also provides a method of treating a disease or condition using the compounds of Formula I and nanoparticles and nanocarriers of the present invention. In some embodiments, the present invention provides a method of treating a disease or condition, including administering to a subject in need thereof, a therapeutically effective amount of a conjugate of Formula I or a nanoparticle of the present invention, thereby treating the disease or condition.

Representative diseases or conditions include hyperproliferative disorders including cancer. In some embodiments, the disease or condition can be cancer. In some embodiments, the disease or condition can be carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, multiple myelomas, Hodgkin's lymphoma, or non-Hodgkin's lymphoma. Additional cancers are known to one of skill in the art and can be found in CANCER: PRINCIPLES AND PRACTICE (DeVita, V. T. et al. eds 2008.

Other diseases that can be treated by the compounds, nanoparticles and nanocarriers of the present invention include: (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome). In some embodiments, the disease can be cancer. In other embodiments, the disease can be bladder cancer or ovarian cancer.

In addition, the compounds, nanoparticles and nanocarriers of the present invention are useful for the treatment of infection by pathogens such as viruses, bacteria, fungi, and parasites. Other diseases can be treated using the nanocarriers of the present invention.

Conjugation of the hydrophilic therapeutic agent and the hydrophobic therapeutic agent enables administration of the therapeutic agents at a level that is typically less than the dose necessary for administration of the therapeutic agent by itself. In some embodiments, the therapeutically effective dose is a dose less than the therapeutically effective dose for the unconjugated therapeutic agent.

When the compound of Formula I includes a photo-active compound, the method of treating can also include the step of exposing the subject to radiation to excite the photo-active compound. Radiation at any suitable wavelength can be used to excite the photo-active compound. The radiation can be at a single wavelength or several wavelengths. The radiation can be administered via any suitable source, such as a laser. In some embodiments, the method also includes exposing the subject to radiation of a sufficient energy and wavelength to excite the photo-active compound of the conjugate. In some embodiments, the electromagnetic radiation is provided by a laser.

The compounds, nanoparticles and nanocarriers of the present invention can also be used for treating a disease or condition via sonodynamic therapy. In some embodiments, the present invention provides a method of treating a disease or condition via sonodynamic therapy, including administering to a subject in need thereof, a therapeutically effective amount of a conjugate of Formula I or a nanoparticle of the present invention, and exposing the subject to a sonic wave, thereby treating the disease via sonodynamic therapy. The sonic wave can be generated using any suitable device.

VI. Methods of Imaging and Detecting

The present invention also provides methods of imaging a tissue or organ using the compounds, nanoparticles or nanocarriers of the present invention. In some embodiments, the present invention provides a method of imaging a tissue or organ, including administering to a subject to be imaged, an effective amount of a conjugate of Formula I, or a nanoparticle of the present invention, such that the conjugate or nanoparticle concentrates in the tissue or organ, and imaging the tissue or organ using a suitable device.

The present invention also provides methods of detecting a tumor in a subject using the compounds, nanoparticles or nanocarriers of the present invention. In some embodiments, the present invention provides a method of detecting a tumor in a subject, including administering to the subject an effective amount of a conjugate of Formula I, or a nanoparticle of the present invention, exposing the subject to radiation at a first wavelength, and detecting any emitted radiation from the conjugate or nanoparticle, thereby detecting the tumor.

VII. Systems

The present invention also provides a system of a conjugate, nanoparticle or nanocarrier of the present invention, and a laser. In some embodiments, the present invention provides a system of a compound of Formula I, or nanoparticle of the present invention, and a laser. In some embodiments, the system includes a compound of Formula I, and a laser.

VIII. Examples

Example 1. Preparation of Pheophorbide A and Irinotecan Conjugates

Materials and Characterization.

Irinotecan was purchased from BIOTANG Inc. (MA, USA). Pheophorbide A was bought from Santa Cruz Biotechnology. N,N'-Dicyclohexylcarbodiimide (DCC), 4-(Dimethylamino)pyridine (DMAP), DCF-DA, $MnCl_2$ and all solvents were purchased from Sigma-Aldrich (MO, USA). Singlet oxygen sensor green and Lyso-Tracker Green, Singlets Oxygen Sensor Green and CellROX were purchased from Thermo Fisher Scientific Inc. Cell cultures medium, fetal bovine serum, cell cultures dishes and plates were purchased from Corning Inc., USA. PDX glioma tumours tissues were courtesies from Dr. David James's lab in Neurological Surgery at the University of California, San Francisco. The synthetic compounds were analyzed by Bruker UltraFlextreme MALDI-TOF-MS and 600 MHz Avance III NMR Spectrometer (Bruker, German). Transmission electron microscopy (TEM) was performed on a Philips CM-120 TEM with 80 kV acceleration voltage. The cell level laser treatments were conducted under laser source that with broader covering area (Omnilux new-U). In vitro fluorescence pictures were captured by confocal laser scanning microscopy (CLSM, LSM810, Carl Zeiss). The in vitro magnetic resonance imaging (MRI) were conducted on a Biospec 7T MRI instrument (Bruker, German)

Synthesis of pheophorbide A and irinotecan conjugate (PI). Pheophorbide a (300 mg, 0.48 mmol) and DCC (120 mg, 0.58 mmol) were dissolved in anhydrous Dichloromethane (5 mL), and the mixture was stirred at 0° C. After 30 min, the reaction system was added to a solution of Irinotecan (359 mg, 0.58 mmol), DMAP (14.2 mg, 0.116 mmol) and anhydrous Dichloromethane (3 mL), and the resulting solution was stirred for 48 h at room temperature in the dark. Then the reaction mixture was filtered and concentrated under vacuum. The crude product was purified by column chromatography using dichloromethane and dichloromethane/methanol (10:1 v/v) as the eluent. The product was collected and the solvent was removed by rotary evaporation to give a black solid. The purified products were characterized by MALDI-TOF-MS and $^1$H-NMR.

Preparations and characterizations of Pa—Ir nanoparticles (PIN). The PIN were self-assembled by nano reprecipitation method. 1 µL PI stock solution (100 mM in DMSO) was dropped into 999 µL Milli-Q water under sonication. After 5 s vortex, 100 µM PIN were fabricated. The size distributions and polydispersity index (PDI) of nanoparticles were evaluated by a dynamic light scattering instruments (Zetasizer, Nano ZS, Malvern, UK). The morphology of NPs was observed through Philips CM-120 TEM. To make TEM samples, the aqueous nanoparticle solution (50 µM) was dropped on copper grids and naturally dried under room temperature.

Preparations of $Mn^{2+}$ chelated PIN. $Mn^{2+}$ chelation was followed the published method. Briefly, 23.2 mg PI (20 µmol) and 12.6 mg $MnCl_2$ (100 µmol) were dissolved in 1 mL methanol (contailed 100 µL pyridine), and refluxed for 2 h. The reaction system was then cooled under room temperature, the un-chelated $Mn^{2+}$ was removed by extracted with Milli Q water and $CH_2Cl_2$ for 5 times. The $Mn^{2+}$ chelated PIN stayed in organic layer, and was dried with a rotavapor.

Critical aggregation concentrations (CAC) assessment. Pyrene ratiometric method was employed to determine the CAC value of PIN. Briefly, 999 µL of different concentrations of PIN were prepared, and 1 µL of 0.1 mM pyrene solution (in acetone) was introduced into PIN solution and yielded 0.1 µM pyrene solution. The PIN and pyrene contained solutions were then transferred into a 96-well plate and incubated at 37° C. for 2 h. After the incubation, the fluorescence of each well was evaluated by a microplate reader (excitation is 335 nm). The $I_3/I_1$ values were recorded for CAC assessment.

In vitro near infrared fluorescence (NIRF), reactive oxygen species (ROS) and photothermal evaluation. PIN or PI were dropped on a transparent film, and the near-infrared fluorescence of was scanned using a Kodak multimodal imaging system IS2000MM with an excitation at 625±20 nm and an emission at 700±35 nm. The photothermal effects of PIN and PI were evaluated by using a FLIR thermal camera. Different concentrations of PIN or PI were placed in 96-well plate, and exposed under 680 nm laser for 3 min, the thermo generations were recorded by FLIR thermal camera. The ROS productions were evaluated by using singlet oxygen sensor green (SOSG) as an indicator. Briefly, different concentrations of PIN or PI were incubated with SOSG the working solution was then exposed under 680 nm laser for 3 min. The green fluorescence of SOSG was monitored by micro-plate reader (SpectraMax M2, Molecular Devices). In these experiments, PI dispersed solution was prepared by dissolved PI molecules powder into good solvent (DMSO).

Stabilities of NPs in serum. PIN was diluted in water and 10% fetal bovine serum water solution respectively. The final concentrations of PIN were set to 50 µM. Then, each solution were kept in cell cultures incubator (5% carbon dioxide and 10% humidity). Temperatures were in constantly 37° C.). The size distributions at each time point were tested by dynamic light scattering to check the stabilities of PIN.

Laser triggered drug release of PIN. Two parallel groups of 300µL, 50 µM PIN were placed in a 96-well plate, one group was set to a neutral pH value (7.4), and another group was set to acidic pH value (5.0). Each group was assigned into three laser treatments, i.e. no laser treatment, low laser power (680 nm, 0.4 w/cm$^2$) and high laser power (680 nm, 0.8 w/cm$^2$) treatments. Each laser treatment lasted for 3 min, the next laser treatment was applied after a 12 min interval (to make the solvent completely descending to room temperature). Then 1 µL solutions from each treatment were diluted into 199 µL DMSO and applied for Ir fluorescence intensity test, the accumulation drug release of PIN was calculated by fluorescence of released Ir divided fluorescence of Ir in the same concentrations of Pa and Ir mixture to avoid the potential FRET caused Ir fluorescence quench. To avoid the volume loss, 1 µL fresh PIN will be complemented back into the treated group immediately after we drew 1 µL samples from laser treated systems.

Cell viabilities evaluation. U87-MG cells were purchased from the American Type Culture Collection (ATCC, Manassas, Va., USA). Cells were cultured in RPMI 1640 Medium supplemented with 10% fetal bovine serum, 100 U/mL penicillin G, and 100 mg/mL streptomycin in a humidified 37° C. with 5% $CO_2$. Cell viabilities were determined by MTS method. U87-MG cells were seeded in 96-well plates with a density of 5000 cells per well. The cells were incubated overnight until fully attached. The cells were treated with different concentrations of Pa, Ir, Pa and Ir mixture and PIN. 12 h later, the extracellular materials were washed off with PBS and replaced with fresh culture media. Laser treated group were exposed under a laser source of Omnilux New-U device (630 nm) for 3 min, and further incubated with non-laser treated cells for another 24 h. MTS was added to each well and further incubated for 2 h. The UV-vis absorbance at 495 nm with a reference wavelength of 630 nm was detected using a micro-plate reader using an SpectraMax M3 Multi-Mode Microplate Readers (Molecular Devices, LLC., CA, USA). Untreated cells in medium were used as controls. Untreated cells served as a control. Results were shown as the average cell viability [($OD_{treat}$−$OD_{blank}$)/($OD_{control}$−$OD_{blank}$)*100%] of triplicate wells.

Intracellular laser triggered drug releasing behaviours of PIN. Two 96-well plates of U87-MG cells were treated with 10 µM PIN for 2 h respectively. Then the PIN contained medium was washed off with PBS for three times, and replaced with fresh medium. The laser treated groups were exposed under 680 nm laser (0.2 w/$cm^2$) for 1 min, and the intracellular behaviours of Pa and Ir were recorded with confocal laser scanning microscopy (CLSM) in different time points. The control group were not treated with laser, but observed under CLSM at the same timepoints of their laser treated counterparts. For Pa fluorescence capture, Cy5 tunnel was applied, and Ir was using DAPI tunnel.

Lysosomes co-localizations. 10 µM PIN were incubated with U87-MG tumour cells for 2 h, and replaced with fresh medium. The cells were then treated with 680 nm laser (0.2 w/$cm^2$) for 1 min, and further cultured for another 21.5 h. After that, LysoTracker™ Green DND-26 was introduced and incubated with cells for 0.5 h. The subcellular distributions of Pa, Ir, and lysotracker were recorded by CLSM. For lysotracker, FITC tunnel was used.

Flow cytometry evaluation of ROS production in U87-MG cells. Two groups of U87-MG cells were incubated with 10 µM PIN for 2 h respectively, then the PIN contained medium was washed with PBS for three times, then replaced with fresh medium. The DCF-DA was introduced for ROS indication. The non-laser treated cells were keeping in dark, and the laser related cells will be exposed under 630 nm laser for 1 min (Omnilux New-U device). The cells were and collected for flow cytometry analysis. For Pa fluorescence detection, Cy5 tunnel was used, and for DCD-DA, FITC tunnel was applied.

CLSM observations of laser guided cell apoptosis. U87-MG tumour cells were incubated with 10 µM PIN for 2 h in glass-bottom dishes, then stained with 40 nM of DiOC6(3) (Green) for 20 min at the end of incubation to evaluate mitochondrial membrane potential, and followed by exposed under laser to elicit photo related therapies. Propidium iodide was employed to stain the dead cells.

Patients derived xenograft (PDX) glioma bearing mice models establishment. Male athymic nude mice (j:nu strain), with 6~8 weeks of age, were purchased from Harlan (Livermore, Calif., USA). All animal experiments were strictly in compliance with the guidelines of Animal Use and Care Administrative Advisory Committee at the University of California, Davis. The glioma bearing mice models were established by inoculated PDX glioma tissues subcutaneously into the right flank of the nude mice. The PDX glioma bearing mice were used for in vivo experiments when tumours were completely developed.

In vivo photothermal therapy. PIN was intravenous injected (i.v.) into tumour bearing mice (n=6). 24 h or 48 h later after the i.v. injection, the tumour regions were exposed under 680 nm laser with low (0.4 w/$cm^2$) and high (0.8 w/$cm^2$) power for 3 min. Pa/Ir mixture and PBS group were treated with high dose laser (3 min) as control group. After the laser treatment, the laser caused temperature elevation was immediately recorded by a thermal imaging camera.

In vivo ROS production. PBS, Pa/Ir and PIN were i.v. injected into tumour bearing mice, the tumour regions were then exposed under 680 nm laser. Tumours of PIN treated mice were exposed under 0.4 w/$cm^2$ and 0.8 w/$cm^2$ laser, PBS and Pa/Ir mixture groups were treated under 0.8 w/$cm^2$ laser as control. Then the tumours were harvested and dipped into ROS probe (CellROX® Deep Red), and applied to NIRF imaging immediately. The red fluorescence was captured with Kodak multimodal imaging system IS2000MM with an excitation at 625±20 nm and an emission at 700±35 nm.

In vivo laser triggered NIRF imaging. Pa/Ir and PIN were i.v. injected into PDX tumour bearing mice, tumour regions were exposed under 0.4 w/$cm^2$ 680 nm laser for 3 min, then applied for NIRF imaging at different time point. The fluorescence of Pa was collected by a Kodak multimodal imaging system IS2000MM with an excitation at 625±20 nm and an emission at 700±35 nm.

Pharmacokinetics evaluation. The jugular vein of male Sprague-Dawley rats was cannulated and a catheter was implanted for intravenous injection and blood collection (Harland, Indianapolis, Ind., USA). 10 mg/kg PIN and Pa/Ir mixture (Pa/Ir ratio is 1:1, mol/mol) were i.v. administrated into rat (n=3 for each group). Whole blood samples (~100 µL) were collected via jugular vein catheter before dosing and at predetermined time points post injection. The kinetics of Pa were measured through testing the fluorescence of 680 nm (excitation is 412 nm), and Ir were collected by measuring the fluorescence of Ir (Ex/Em, 320/460 nm). The values were plotted versus time after the subtraction of blood background.

In vivo therapeutic efficacy evaluation. PDX glioma bearing nude mice were employed for in vivo therapeutic efficacy evaluation. The mice were randomly divided into 6 groups (n=6) for efficacy evaluation of different materials: i) PBS control group; ii) free Ir treatments group; iii) Pa/Ir mixture (High laser dose); iv) PIN without laser; v) PIN (Low laser dose): vi) PIN (high laser dose). All materials were i.v. administrated twice through the tail vein, the tumours were exposed under 680 nm laser for three minutes to trigger the chemo, photodynamic and photothermal therapies. Each dose corresponds to two laser exposures, laser treatments were applied at 24 h and 48 h after the i.v. injection. The tumours sizes and body weights of all mice were recorded during the treatment.

In vitro MRI imaging on U87-MG cells by $Mn^{2+}$ chelated PIN. Different concentrations of $Mn^{2+}$ chelated PIN were incubated with U87-MG cells for 2 h. The cells were then collected and fixed in agarose gel. The fixed cells were then applied for $T^1$ MRI visualization.

Results

Figure 2A:
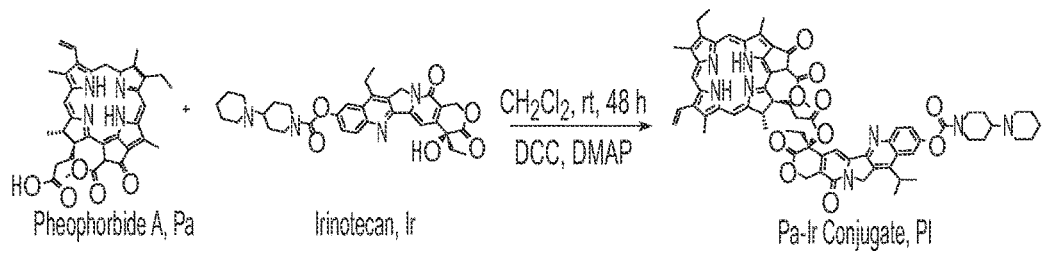
FIG. 2a-j shows Synthesis and characterizations of PI and PIN.
Figure 2B:
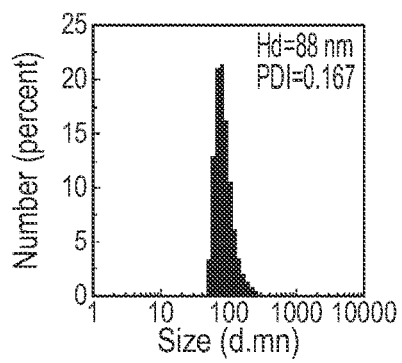
Figure 2C:
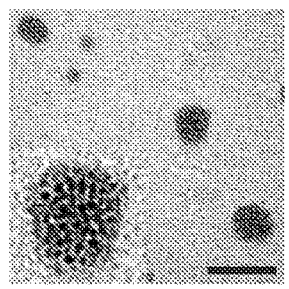
Figure 2D:
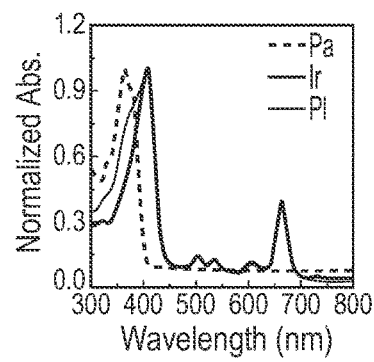

Fabrication and characterizations of PIN. PI molecules were synthesized by covalently conjugating two commercial available APIs (Pa with carboxyl group, and Ir with hydroxyl group) through a simple esterification (FIG. 2a). The molecular weight of synthesized PI (theoretically 1160 Da) was confirmed by mass spectrometry (MS). The MS spectrum showed a [M+H]$^+$ peak (1161 Da) and followed with a [M+Na]$^+$ peak (1183 Da), which supported that PI was purely synthesized, as only peaks of PI were observed. Nuclear magnetic resonance (NMR) was employed to verify the synthesis NMR spectrum of PI exhibited both characteristic peaks of Pa and Ir, indicating the compositions were correct. Then, PI molecules were assembled into their nano-formulations (PIN) through typical reprecipitation method. As shown in FIG. 2b, the size distributions of PIN were around 88 nm, and the polydispersity index (PDI) was 0.167, suggesting the nanoparticles were uniform in size and well-dispersed in aqueous solution. TEM (FIG. 2c) image showed that the PIN was with spherical morphology, and composed with plenty of small dark dots. The small dots aggregation suggested that PI molecules were possibly assembled into micelle-like architecture, the small micelles were further assembled through secondary aggregations, and formed relatively larger nanoaggregates. To verify the self-assembly of PIN, the critical aggregation concentrations (CAC) were investigated. The CAC of PIN was calculated as 1 μM (equals to 1.161 μg/mL). As PI was composed with two molecules with large aromatic structures, the UV-vis absorbance of Pa, Ir and PI were evaluated. As shown in FIG. 2d, free Pa exhibited two main characteristic peaks at 412 and 570 nm, and three small peaks distributed in the range of 450 to 690 nm. Pure Ir showed a single absorbance at 370 nm. In comparison, PI molecules performed all characteristic peaks of Pa, plus a distinguishable shoulder on the left of Pa's 412 nm peak, the shoulder overlapped with 370 nm peak of Ir, suggesting that PI molecules were composed with both Pa and Ir. The UV-Vis results further supported that our PI synthesis was succeed.

Figure 2E:
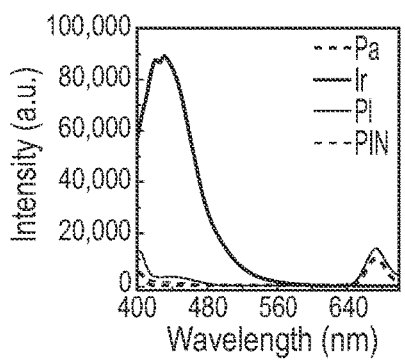
Figure 2F:
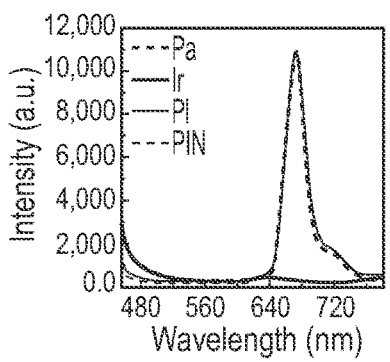
Figure 2G:

Fluorescent energy transfer relay and NIRF imaging of PIN. In FIG. 1, we envisioned that PIN were self-indicating nanoparticles with innate fluorescence. Hence, the fluorescence behaviours of Pa, Ir, PI molecules and PIN were investigated. As shown in FIG. 2e, Pa and Ir showed their fluorescence peaks at 690 and 430 nm respectively after being excited at 370 nm (the maximum absorbance of Ir). PI molecules were composed with Pa and Ir, they were supposed to exhibit both fluorescence peaks of Pa and Ir. Interestingly, the fluorescence intensity at 430 nm was, however, extensively decreased in comparison to equal amount of free Ir, but showed a slightly enhanced fluorescence intensity at 690 nm than that of same concentrations of Pa. We hypothesized the fluorescence descent of Ir was caused by energy transfer between Ir and Pa, the Ir transferred its emissive energy to Pa, and Pa showed enhanced fluorescence due to the extra energy received from Ir. To prove our hypothesis, the spectra overlap between Ir and Pa was investigated. A spectra overlap was observed between the emission of Ir and absorption of Pa, suggesting that the spectra factor met the requirement of energy transfer occurrence, and Ir acted as donor, Pa was the acceptor. The fluorescence of Pa was augmented when it was excited by the excitations of Ir, but showed almost same intensities under the excitations of Pa while comparing with free Pa under same concentrations. Therefore, the fluorescence decreasing of Ir was ascribed to energy transfer from Ir to Pa. The fluorescence behaviours of PIN were then evaluated, neither the fluorescence of Ir nor Pa (FIG. 2e and FIG. 2f), was detectable. Ir quenching was ascribed to energy transfer, and Pa quenching was hypothetically conceived as aggregation caused quenching (ACQ) between the "π-π" stacking of each Pa molecule, as the planar molecular structures of Pa were supposed to be tightly piled up in nanostructure. To prove this hypothesis, we mixed water (poor solvent) and dimethyl sulfoxide (DMSO, good solvent) under various volume ratios to prepare the solvents with different solubilities towards PI. PI molecules were supposed to experience different extent of aggregation states in the solvent mixtures. The fluorescence of PI stayed in high intensity when they were dissolved in pure DMSO, and gradually decreased along with the elevation of the water fractions ($f_w$). As the $f_w$ were more than 20%, fluorescence of Pa was extensively decreased, and till the $f_w$ reached to 80% or more (100%), the fluorescence was extensively quenched, and more than 80 times less than that was dissolved in good solvent. Hence, the fluorescence inactivation of Pa was ascribed to π-π stacking induced ACQ between the Pa molecules in PIN. As such, PIN was composed with two fluorescent molecules, but both fluorescence were inactivated by an energy transfer relay, i.e. Ir transfers its emissive energy to Pa, and Pa quenched both fluorescence of Ir and itself by ACQ. In other words, the fluorescence of Pa can be recovered once the nano-structures of PIN was broken down (ACQ becomes invalid), and the emission of Ir was able to be rebounded as the Ir was released from PIN (energy transfer loss). Based on this, PIN enable to achieve a dual-colour fluorogenic process, and each fluorescence recovery indicated different in vitro or in vivo details. For instance, Ir fluorescence recovery was competent for indicating the drug release, Pa fluorogenic was able to indicate the existence of the nano-status of the PIN, and both fluorescence can unveil the real biological dispositions of PIN. Since Pa was with excellent NIRF indicating feature, we further investigated its NIRF imaging ability. Different concentrations of PIN and PI solution (dissolved PI molecules in DMSO) were prepared, and applied to NIRF animal imaging system, as shown in FIG. 2g, the fluorescence of PIN seemed completely turned off, even the concentrations were increased. On the contrary, the fluorescence of dispersed PI solution was literally enhanced with an elevation of PI concentrations. The fluorescence imaging results were in agreement with the fluorescence spectra (FIG. 2f), suggesting that the PIN were excellent NIRF contrast agents, and the NIRF imaging ability was tunable. The NIRF imaging results supported that the "ON" and "OFF" of the Pa fluorescence enabled to indicate the existence of PIN.

Figure 2H:
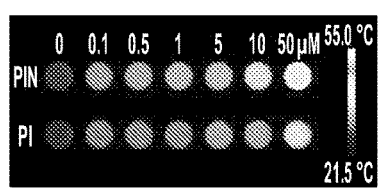
Figure 2I:
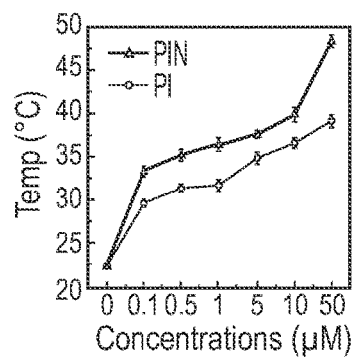
Figure 2J:
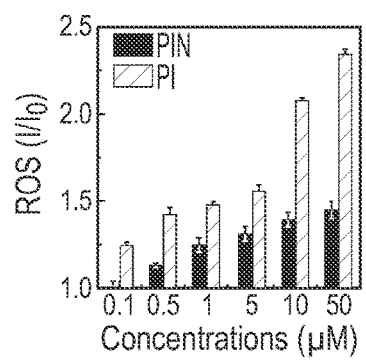

Photothermal and photodynamic effects evaluation. We then investigated the photo induced thermo and ROS generations of PI and PIN. FIG. 2h showed thermal effect of PIN and PI. PIN was comparatively generated more heat than their dispersed counterparts, the higher temperature enhancement of PIN can be ascribed to restrictions of molecules movements in nanostructures, the most photo energy was transformed to thermo, rather than contributed to intramolecular motions or molecules movements. FIG. 2i was quantitative data collected from FIG. 2h, showing that the photothermal effect was correspondingly increased with the concentrations, and temperatures of PIN (50 μM) can reach to nearly 50° C. The PDT effect of PI and PIN was indicated by a singlet oxygen probes (singlet oxygen sensor green, SOSG), as shown in FIG. 2j, dispersed PI showed more effective PDT effect than their nano-formulation (PIN), both of PI and PIN performed excellent PDT effect, and were qualified for PDT.

Stability evaluations of PIN. The stability of PIN was tested prior to the biological studies. PIN were incubated with or without 10% fetal bovine serum (FBS) at 37° C., then the hydrodynamic diameters (Hd) were evaluated by DLS at different timepoint. The fresh PIN without FBS were with a Hd around 80 nm, and didn't further form agglomerates with time elapse, the Hd of PIN steadily kept in small size, and eventually stayed around 60 nm in a week. The Hd of PIN became bigger when FBS was presented (PIN in this experiments were from the same PIN stock), the presence of FBS made the PIN increased from ~80 nm to nearly ~115 nm, the size increments were hypothetically ascribed to the formation of protein corona, which generally happened on the most nanoparticles when they were administrated into a biological system. However, the PIN kept stable even it was incubated with FBS for one week under 37° C., indicating that PIN were capable of keeping in high stability when they met proteins and formed corona under the situations like incubating with cells, or in blood vessel.

Figure 3A:
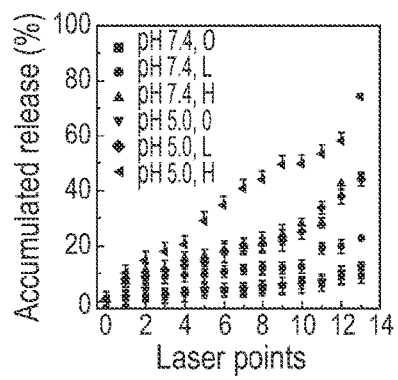
FIG. 3a-g shows In vitro evaluation of laser triggered drug release and controllable combination therapy of FAPIN.
Figure 3B:
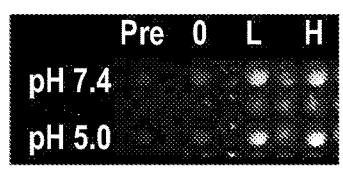

Laser/acid pH triggered accumulated drug release. PIN was constructed with a photosensitizer and a chemotherapeutic drug through an ester bond. In this particular design, the laser may irridate the photosensitizer, and acid pH enabled to hydrolyze the ester bond. PIN, therefore, was supposed to perform laser/acid pH triggered drug release pattern. Before applying laser to trigger the nanoparticles, the laser doses were optimized by evaluating the photothermal effects under different laser power. The photothermal effect of PIN was literally escalated with the laser power increased. The temperature enhancements ($\Delta T$) were varied from 14° C. (0.2 w/cm$^2$) to 49° C. (1.0 w/cm$^2$), indicating more laser power applied, more photothermal induction. Based on the photothermal outcomes, we chose two moderate laser doses for the following phototherapies evaluation, 0.4 w/cm$^2$ and 0.8 w/cm$^2$ corresponded to low and high laser doses respectively. Then, PIN was dispersed in different pH circumstance (pH 7.4 and pH 5.0) and exposed under laser. As shown in FIG. 3a, in neutral pH solution, PIN released less Ir when no laser treatment applied, and exhibited more drug release with continuous laser exposure. Higher laser power applied, more Ir got released. In the results, acidic pH environment obviously expedited the drug release, the fluorescence of Ir was higher than their corresponding groups that solely treated with laser. The drug releasing of PIN reached to the highest level (almost 80%) when laser and acidic pH concurrently took part in, and much higher than sole pH or laser stimulation. FIG. 3b was the optical image of the Ir fluorescence before and after laser and pH triggered drug release, under the co-stimulations of laser and acidic pH, blue fluorescence of Ir was markedly higher than their untreated counterparts. The drug releasing patterns suggested that PIN would also experience a laser triggered chemotherapy in vivo.

Figure 3D:
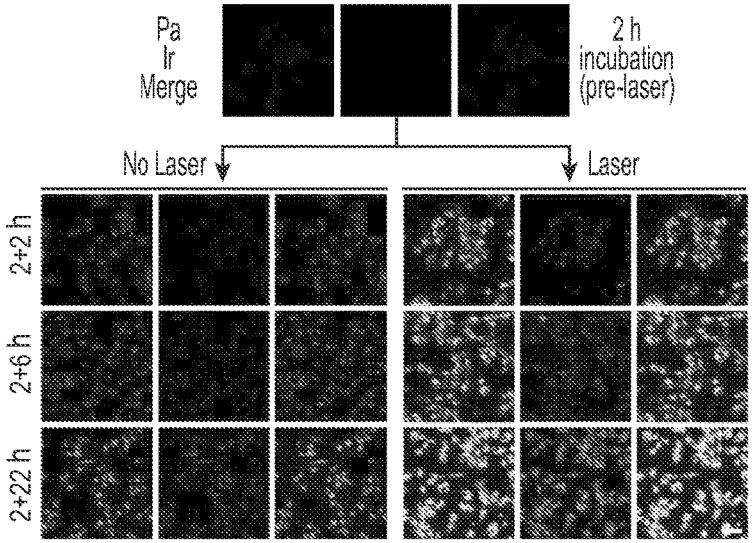
Figure 3C:
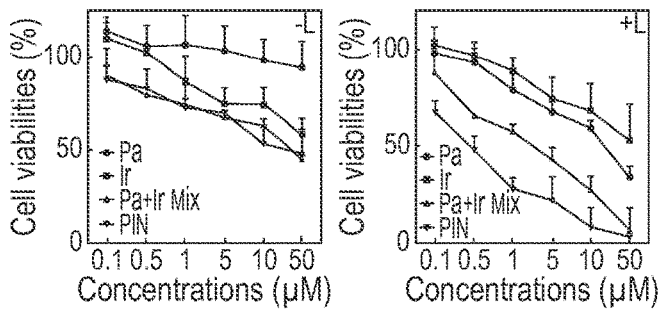

Cell viabilities of PIN, Pa+Ir mix, Pa and Ir. PIN was then incubated with tumour cells for investigation of the therapeutic efficacy. Different concentrations of PIN and its components (Pa and Ir) were incubated with U87-MG tumour cells for cell viabilities evaluation. Pa/Ir physical mixture was also introduced to mimic a formulation with both of free Pa and Ir. As shown in FIG. 3c, photosensitizer groups (Pa) alone exhibited no obvious cytotoxicity if they were not exposed under laser. Under the same situation, the other three groups performed some extent, but not very striking efficacy, as they all contained chemotherapeutic drug. Then, laser treatments were introduced to activate the photosensitizer. Ir showed similar drug efficacy as comparing with its non-laser treated counterparts. Pa exhibited distinguishable cell killing effect under laser exposure, and Pa/Ir mixture gave more efficient therapeutic effect comparing to single Pa or Ir, the improved efficacy may be ascribed to combination therapies of phototherapies and chemotherapy. PIN exerted the most efficient therapeutic effect than the other three groups, and the IC$_{50}$ reached a very low concentration (~0.5 μM), in comparison with Pa/Ir mixture (almost 5 μM) and Pa (nearly 50 μM). The highest efficacy of PIN was not only supposed to be given by synergistic therapies of PDT, PTT and chemotherapy, but also caused by bulk drug delivery feature of nanoparticles, which generally leads more therapeutic agents ingesting into cells. The overwhelming therapeutic effects between the groups with or without laser treatments suggested that laser not only triggered the phototherapies of PIN, but also escalate the drug release of the Ir, thus activated the chemotherapeutic effect.

Figure 3E:
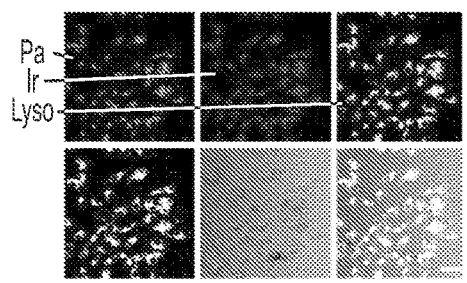

Dual-fluorogenic process indicated the spatiotemporal drug release and subcellular distributions of PIN. PIN were self-indicating nanoparticles, the fluorescence recovery of Pa reflected the collapse of the nanostructures of PIN, and the fluorogenic of Ir directly indicated the drug release from PIN. We incubated PIN with U87-MG cells, and observed the dual-fluorogenic processes of Pa and Ir in a spatiotemporal manner (FIG. 3d). Two parallel treatments (with or without laser exposure) were set by incubating PIN with cells for 2 h. Then, PIN of each group was washed off and replaced with fresh medium. Before being exposed under laser, neither the fluorescent signal of Pa nor Ir, can be distinguishably recorded by confocal laser scanning microscopy (CLSM). As control experiment, non-laser treatment group performed slightly fluorogenic phenomenon of Pa, and very weak Ir fluorescence recovery after 24 h incubation. In contrast, the laser treated group exhibited obvious Pa fluorescence recovery in 2 h of post-laser treatment, but less Ir recovery, indicating that laser exposure may firstly trigger the collapse of PIN. In 6 h of post-laser treatment, Pa tunnel became brighter, and blue fluorescence of Ir can be obviously observed. After another 22 h incubation, the fluorogenic subsequences of both Pa and Ir become markedly. CLSM results supported that PIN experienced a laser triggered drug releasing process, the laser can markedly expedite the drug releasing of PIN. In the CLSM results, Pa and Ir were mostly distributed in cytoplasm within 24 h incubations. We also observed the subcellular distributions of free Pa and Ir, and free reagents exhibited almost same subcellular distributions with the ones in nanoformulations (PIN). The subcellular distributions of Pa and Ir were co-localized in a certain region and exhibited brighter fluorescence, indicating PIN may release Ir in particular site. As nanoparticles generally experienced an endocytosis pathway and be transported to endosome/lysosome of cells, we envisioned that the brighter regions may denote where the lysosomes are. To prove this, we co-stained the PIN treated cells with LysoTracker™ Green DND-26, and applied for CLSM observation to check the lysosomes co-localization. As shown in FIG. 3e, the fluorescence of Pa, Ir and lysosomes were perfectly colocalized, indicating that the microenvironment of lysosomes may assist the drug releasing of PIN, such as low pH value (~5.0). The subcellular drug releasing behaviours were consistent with the laser-/pH-co-stimulated drug releasing results (FIG. 3a and FIG. 3b), and supported that PIN responded to both external (laser) and internal (acidic pH) stimuli, and thus enabled to achieve highly controllable cancer treatments.

Figure 3F:
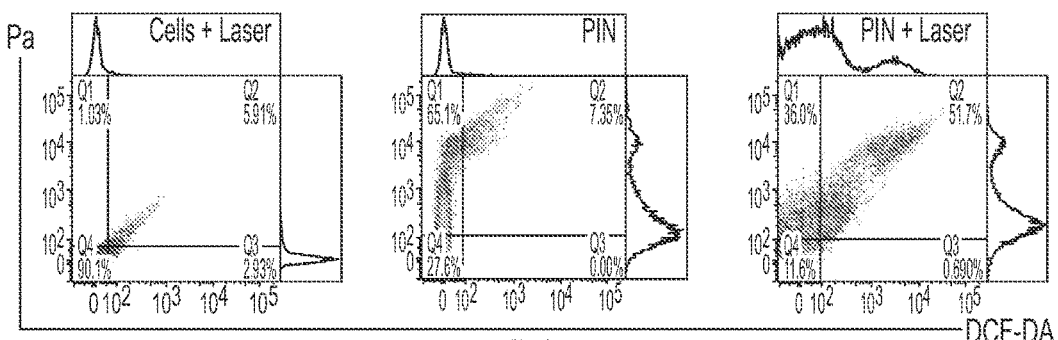
Figure 3G:
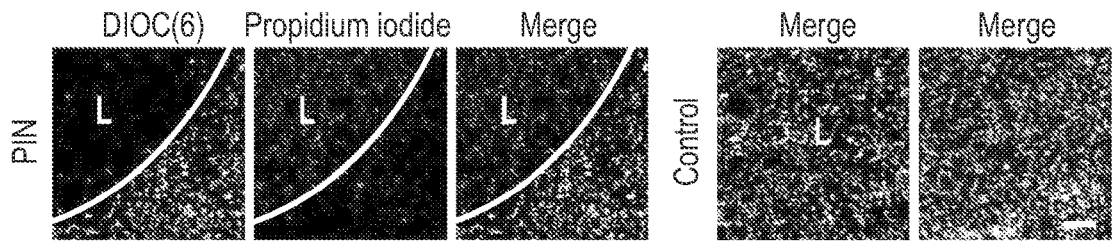

In vitro phototherapies evaluations of PIN. In vitro PDT effect of PIN was indicated by an ROS indicator (2',7'-dichlorofluorescin diacetate, DCF-DA) and evaluated by fluorescence activated cell sorting (FACS). The fluorescence of DCF-DA and Pa was collected by FACS and respectively giving a quantitative analysis of ROS production and PIN ingestion. As shown in FIG. 3f, U87-MG cells produced less ROS under laser exposure, most cells were sorted in Q4 (90.1%), indicating laser took less effort on producing ROS. For PIN treated cells, the cells in Q2 sorting area didn't increase obviously, indicating PIN did not generate ROS if no laser treatments applied. Q1 sortation increasing was ascribe to the ingestion of PIN into cells. PIN with laser treated group exhibited very striking ROS production, cells in Q2 sorting area were extensively increased from 5.91% to 51.7%. FACS results supported that PIN enabled to yield excellent PDT under laser treatments. Since PIN was highly responsive to laser treatment, we hypothesized that PIN was competent for controllable and precise cancer abrogation. Hence, PIN was incubated with U87-MG cells, and a certain region of PIN incubated U87-MG cells were exposed under laser beam, the cell death profiles were comparatively assessed between the laser exposed region and non-laser treated cells (FIG. 3g). Cells with laser treatments were mostly dead, as their mitochondria membrane potential lost, and most cells were stained with propidium iodide. In comparison, cells only group (control) didn't exhibit obvious cell death, most cells were stained with DIOC(6), and performed less red propidium iodide staining. These results supported that PIN enables to achieve highly controllable and accurate therapeutic effect, i.e., only cured the regions where the laser pointed.

Figure 4A:
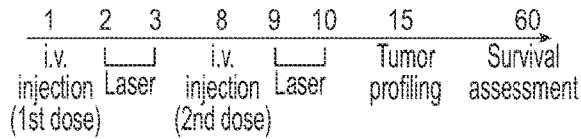
FIG. 4a-k shows In vivo laser triggered NIRF imaging and trimodality therapy of FAPIN.

Glioma is a type of tumor that occurs in the brain and spinal cord, and causing ~30% of brain and central nervous system tumors, and 80% of malignant brain tumors. Hence, we applied PIN on patient derived xenograft (PDX) model of glioma tumors and tried to prove the trimodality therapy. As shown in FIG. 4a, Patient derived glioma tissues were subcutaneously inoculated a small tissue chuck into the flank of nude mice. The PDX glioma tumours are extremely progressive and malignant, which reached 100-150 mm$^3$ in a short time. The mice were then randomly assigned into 6 groups (n=6), including PBS control, Ir, PIN without laser, Pa+Ir with high dose laser (Pa+Ir H), PIN with high dose laser (PIN H) and PIN with low dose laser (PIN L) groups. The PIN L group was specifically set for demonstration of other therapeutic effects except for PTT, in case the photodynamic and chemotherapeutic effects were in deluge of extremely high PTT effect caused by high dose laser treatment. Two doses of our materials were i.v administrated through tail vein in two continuous weeks. Pa+Ir H, PIN H and PIN L groups were treated with laser after 24 and 48 h of materials administrations, the photothermal effect was recorded by a thermal imaging camera. Tumour volumes and body weights were measured throughout the experiments.

Pharmacokinetics studies of PIN and Pa+Ir mixture. The pharmacokinetic study of PIN was evaluated in jugular vein cauterized rats, and an equal dose Pa+Ir mixture was served as the control. Blood was collected at different time point after i.v. injection, and drug concentrations were based on the measurement of Pa fluorescence. Nano-formulation (PIN) exhibited longer blood circulation time compared to free drugs, suggesting a longer drug interaction window with cancers.

Figure 4C:
Figure 4B:
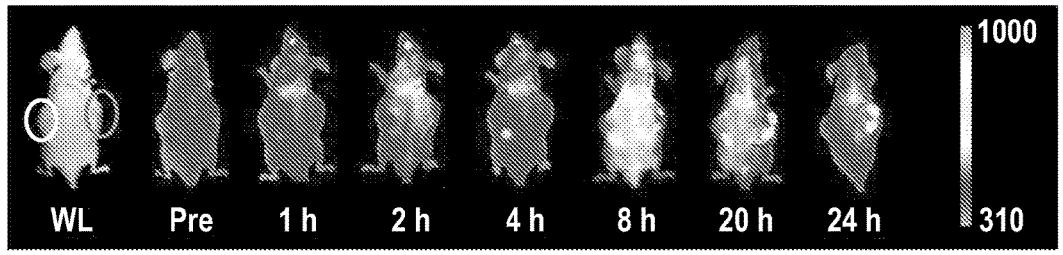

In vivo NIRF imaging of PDX tumour bearing mice. The in vivo laser-triggered drug releasing pattern of PIN was evaluated. Mice were assigned into two groups, and i.v. administrated with PIN and Pa+Ir mixture respectively. For PIN treated group, mice were bearing two xenograft tumours, the right tumour (highlighted by red circle) was exposed under 680 nm laser (0.8 w/cm$^2$) for 3 min (the laser treatment was applied right after 24 h of PIN administration). The NIRF of Pa was monitor in different time intervals (FIG. 4b). Before the light treatment, there was no NIRF signals at both tumor sites due self-quenching of PIN. Upon laser illumination, there was a lime-dependent increase of NIRF signal at the light treated tumor site with a peak at the 24 hour post light treatment. NIRF of Pa can be slightly observed 8 h after laser treatment, and further augmented at 20 h and 24 h timepoints. In contrast, the non-laser triggered tumour (denoted by white circle) showed no detectable NIRF signal. Interestingly, the fluorescence just escalated at the region that was triggered by laser, the non-triggered region (even at the same tumour) exhibited no distinguishable NIRF signal. The mice were then sacrificed, the tumors and major organs were collected for ex vivo NIRF imaging (FIG. 4c). Consistent with our whole mouse imaging finding, only the laser treated tumour exhibited obvious NIRF signal, and the signals of non-laser treated tumours remained low. The increased NIRF at the light treated tumor sites implied the disassociation of the PIN and presumably enhanced the drug release. Although the fluorescence signals from released Ir were too weak due to short wavelength to be acquired with our imaging station. Nevertheless, the changes of Pa NIRF would serve as a real-time self-indicator for drug release. On the contrary, the Pa+Ir treated mice has no Pa accumulation at the tumor site while kidney has a strong fluorescence, indicating that the small molecules of Pa was possibly excreted from kidney.

Figure 4D:
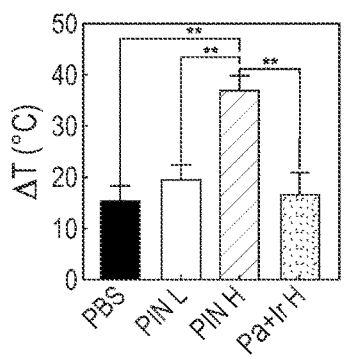

In vivo evaluations of the photothermal and photodynamic effects. The PTT effect of Pa+Ir H, PIN H and PIN L groups were evaluated, PBS groups were also treated with laser as control. FIG. 4d was the statistical data of the PTT effect, demonstrating that PIN H group performed strongest photothermal effect by comparing with other groups, and hovered at more than 35° C. temperature escalations. The PIN L and Pa+Ir H exhibited slightly thermal generations comparing to the group with no photosensitizer (PBS control). The PTT effect of PIN H group exhibited significant difference versus to other three groups (P<0.00). To exclude the non-specific PTT effect, we also exposed laser on the non-tumour regions (legs) of the mice, the non-tumour region showed slightly temperature enhancements even under high dose laser treatments (0.8 w/cm$^2$), the PTT effect was almost as same as the mice treated with PBS, indicating that the laser only burnt the region that harbored the photosensitizer.

Figure 4E:
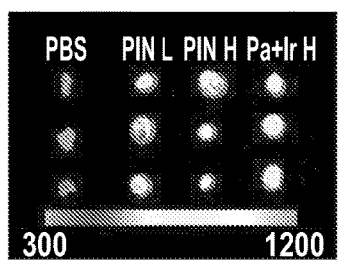
Figure 4F:
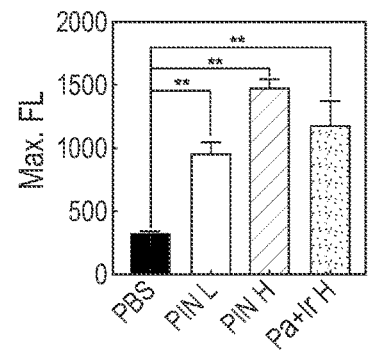

The PDT effect of Pa+Ir H, PIN H and PIN L groups (n=3) were indicated with a fluorogenic NIRF dye, CellROX™ Deep Red Reagent, which stays in non-luminant state, but exhibits strong NIRF in the presence of ROS. As same as PIT evaluation, PBS group was also employed as control. The tumour regions were exposed under laser after 24 h materials administration. Then all mice were sacrificed, the tumours were immediately collected and submerged into CellROX solution for 30 s. The tumours were then applied for NIRF imaging, as shown in FIG. 4e and FIG. 4f, PBS treated groups showed minimum ROS production, the photosensitizer harbored groups all performed excellent PDT effect. PIN H performed most powerful ROS production, then the Pa+Ir and PIN L treated groups, suggesting that the Pa contained groups were all capable of PDT for tumour treatments, and more laser generated more ROS. As the NIRF of CellROX overlapped with the fluorescence of Pa, control groups of pre-CellROX NIRF imaging were also set, all tumours exhibited less fluorescence right after the laser treatment, the results were consistent with the drug releasing animal imaging results (FIG. 4b and FIG. 4c), the fluorogenic of Pa didn't process very soon.

Figure 4G:
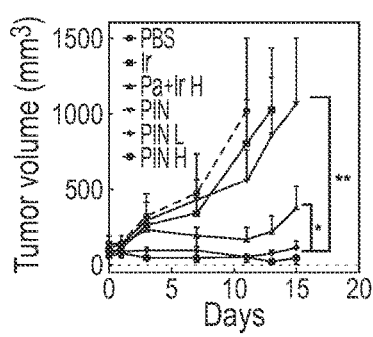

In vivo tumour ablations by trimodality therapy. The tumour ablation effects of each group were profiled (FIG. 4g). The extremely progressive and malignant characteristics of PDX tumours were proven in PBS groups, the tumours grew so fast that all mice cannot survive within short days, if there were no effective treatments. The Ir group performed similar outcomes, the development of PDX glioma tumours cannot be slowed down even by treated with free chemo-drugs. PIN without laser group gave less efficacy as well. As indicated in the in vitro experiments (FIG. 3), PIN without laser treatment exerted less therapeutic effect, as neither the phototherapies, nor the chemotherapy took part in the tumour abrogation. In comparison, the laser treated group performed much better tumour ablation or restrain effects. Pa+Ir H treated group showed better efficacy, the tumour volumes were obviously decreased after two doses treatments. PIN H exhibited the best efficacy comparing to the other groups, the tumours volume was largely decreased after the first dose treatment, and keeping on tumour volume shrinking with time elapse, half mice were completely cured (will discuss later). PIN L group exerted similar therapeutic effect with PIN H treatment. The significant efficacy of PIN L treatment indicated that the combinations of chemo- and photodynamic therapies also took an important role in tumour ablation.

Figure 4H:
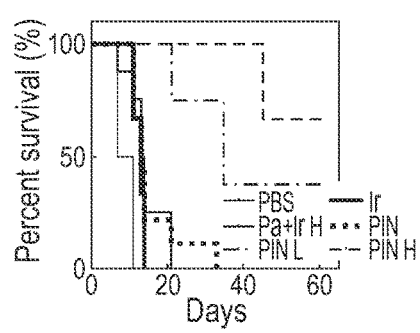
Figure 4I:
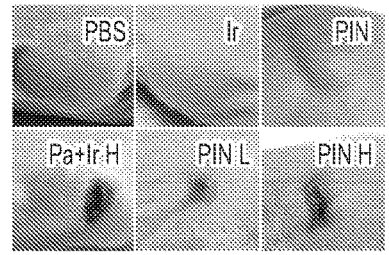
Figure 4J:
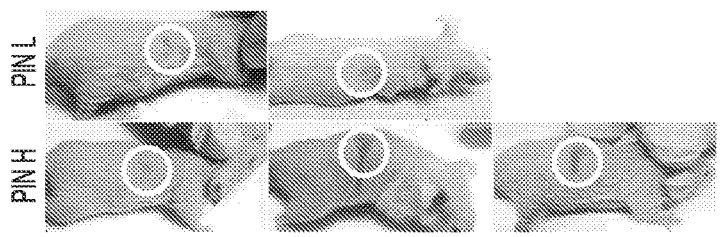

FIG. 4h curved the survival rate of each treatment, PBS, Ir, Pa+Ir and PIN (no laser) groups gave the worst animal survival rate. PIN H and PIN L performed better animal survival rate, and the PIN H completely cured three mice and yielded the best 2 months animal survival qualities. The PIN L also performed excellent efficacy, two mice were completely cured. FIG. 4i was optical images of each group after two doses of treatments. The PBS treated mice bore huge and uncured tumour, so does the Ir treated mice. PIN treated mice showed slightly small tumour size. The laser treated groups performed different levels of tumour ablation effect, Pa+Ir H treated tumours exhibited obvious PTT caused scar on the tumour. Some extent of relapsed tumour can be found by the scar, indicated less effective tumour ablations of Pa+Ir H treatments. PIN L gave slight scar on the tumour site, as the PTT effect was not as effective as its high laser dose counterparts, and notably, no palpable tumour can be detected. As parallel with PIN L, PIN H group gave more obvious scar at tumour region, and no palpable tumour can be found as well. The low frequency relapse of PIN L and H groups may be ascribed to the complementary chemotherapy from the released Ir, as the phototherapies enable to instantaneously provide overwhelming therapeutic effect, but cannot played a sustainable efficacy once the laser was absent. The released Ir may continuously play a chemotherapeutic effect during the post-phototherapy period, and constrain the tumour relapse. We kept the PIN L and PIN H treated mice for two months, and found 2 mice in PIN L and 3 mice in PIN H groups were completely cured (FIG. 4j). The cured rate for PIN H reached to 50% (3 of 6), and PIN L was 33.3% (2 of 6). All cured mice lived in good quality after the scar fell off naturally (the cured regions were highlighted by red circle), no tumour relapse was observed in two months.

Figure 4K:
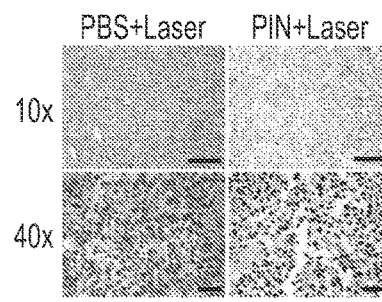

To evaluate the laser oriented specific therapies, we investigated the PIN treated tumor tissue by hematoxylin and eosin (H&E) stain (FIG. 4k). Microscopically, the PIN mediated light therapy caused massive tissue pathological changes, including edema, cellular disassociation and shrinking, pyknosis and karyolysis. Comparatively, the tumour tissue of PBS control groups showed no damage, even under laser exposure, suggesting that sole laser didn't hurt the tissues. H&E stain results supported that our PIN exhibited excellent phototherapeutic effects which enabled to specifically demolish a particular tumour tissues.

Systemic toxicity evaluations. The pathology of the main organs of PIN treated mice was investigated by H&E assay, PIN treated mice performed identical tissue patterns with their PBS treated counterparts, and exhibited no damage towards the mice organs, indicating that our PIN was with good biocompatibilities. There was no significant in the body weight changes among all treatment groups indicating minimal systemic toxicity. The hematologic index didn't exhibited any abnormal alterations after all materials treatments, except for the index of blood urea nitrogen (BUN) on three laser-treated groups (Pa+Ir H, PIN L and PIN H), which showed significant differences ($p<0.05$) to the PBS control. However, the corresponding index of BUN, creatinine, exhibiting no significant differences with PBS group, indicating that the significance differences of BUN on laser treated groups were most likely due to the slight dehydration attributed by multiple anesthesia for light treatment. The systemic toxicity analysis supported that our FAPIN intrinsically performed nice biocompatibilities, and was suitable for further pharmaceutical or medical developments.

Example 2. $Mn^{2+}$ Pheophorbide a—Irinotecan Conjugate

Figure 5A:
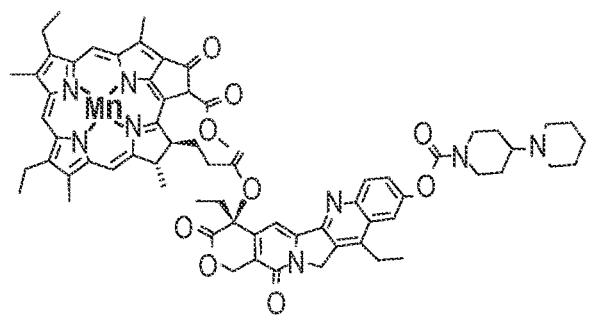
FIG. 5a-d shows In vitro MRI imaging of Mn$^{2+}$ chelated PIN.
Figure 5C:
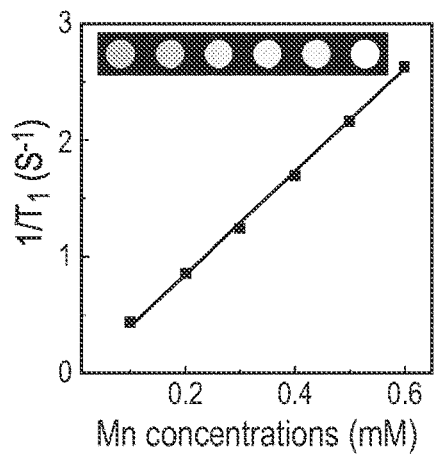
Figure 5B:
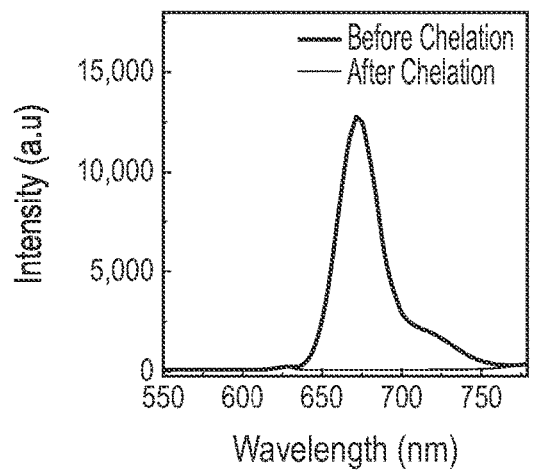
Figure 5D:
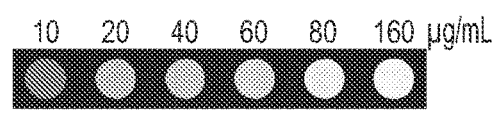

Porphyrin derivatives enable to chelate metal ions to achieve multi-modal in vivo imaging, such as $Mn^{2+}$ chelated Pa realized $T^1$-MRI imaging, and copper (64) makes Pa become PET visible. Here, to extent the multi-modal imaging ability, we chelated $Mn^{2+}$ to PIN, and evaluate the MRI imaging function in vitro. As shown in FIG. 5a and FIG. 5b, the fluorescence of Pa (in PI molecules) was completely quenched by comparing to the non-chelated counterpart, due to the chelation of metal ions. FIG. 5c showed the concentration dependent MRI signal enhancement of PIN, indicating that PIN were capable of MRI imaging. We further incubated PIN with U87-MG cells, and fixed the cells in agarose gel for MRI imaging. As shown in FIG. 5d, the PIN with $Mn^{2+}$ chelation clearly visualized U87-MG cells and performed excellent relaxation ratio. Based on this, our porphyrin based F/HAPIN enables to realize multi-modal imaging abilities as well.

Based on the self-assembly mechanism illustrated in PIN (FIG. 2a), we designed different kinds of porphyrin and hydrophilic drug conjugates. Since porphyrin derivatives are hydrophobic, any hydrophilic drugs can be introduced as hydrophilic parts, and self-assembled into the same type of nanoparticles like PIN. Theoretically, all porphyrin derivatives and hydrophilic drugs conjugate enable to assembled into F/HAPIN, and realize chemotherapy, photothermal therapy and photodynamic trimodality therapy. In porphyrin derivatives and hydrophilic drugs conjugates, the linker was designed as stimuli-responsive, like pH-responsive (Hydrazone, ester bond, Orthoester, Imine, Cis-aconityl, Acetal/Ketal). Enzyme-cleavable peptides (MMP-2/9, Caspase-3/9, Cathepsin B), Redox responsive (disulfide bond) and cis-diol/pH responsive (Boronic ester). The stimuli-responsive linkers are benefit for controllable releasing the API in specific focus.

Example 3. Drug-Drug Conjugates

Drug-Drug amphiphilic conjugates based F/HAPIN. The pure chemotherapeutic drug-drug amphiphilic conjugates also follow our self-assembly rule. We hypothetically designed various kinds of Drug-Drug amphiphilic conjugates, in which the specific stimuli responsive linkers are also embedded. The drug-drug amphiphilic conjugates can form small micelle like nanoparticles, and further assemble into larger nanoparticles. The drug-drug based F/HAPIN is made by different kinds of pure drug, and thus show synergistic therapeutic effect. The followings are doxorubicin based drug-drug amphiphilic conjugates, doxorubicin here acts as hydrophilic part of the amphiphilic conjugate. According to our self-assembly mechanism, the doxorubicin can also be replaced as other hydrophilic drugs, like Irinotecan, Daunorubicin, Idarubicin, Topotecan, etc. For the hydrophobic parts, the hydrophobic chemotherapeutic drugs such as Paclitaxel, Cabazitaxel, Docetaxel, Vinblastine were chosen. The hydrophilic-hydrophobic properties of drugs were determined based on their LogP values, and greater LopP value means more hydrophilic property generally, the linker between two drugs can be set as other stimuli responsive chemical bonds, like pH-responsive (Hydrazone, ester bond, Orthoester, Imine, Cis-aconityl, Acetal/Ketal), Enzyme-cleavable peptides (MMP-2/9, Caspase-3/9, Cathepsin B), Redox responsive (disulfide bond) and cis-diol/pH responsive (Boronic ester). The stimuli-responsive linkers are benefit for controllable releasing the API in specific focus. For the pH-responsive linkers, when the drug-drug assembly nanoparticles entered lysosome in the tumor tissue due to the EPR effect, these linkers will be broken under the acid condition and then let two drugs release simultaneously. For the linker of enzyme-cleavable peptide, when the drug-drug conjugates come around tumor tissues, the linker would be cut because they are substrates of corresponding enzymes overexpressed in tumor cells and then the drugs will be released as well. For other linkers such as disulfide bond, they can be cut based on the redox condition induced by the excessive GSH in tumour.

To increase the stability of nanoparticle and realized the targeted drug delivery, surface modification is very important for F/HAPIN. There are four main methods for us to do this modification. i) PEGylation. Polyethylene glycol is most acceptable polymers for building up the nanoparticles for drug delivery, which exhibits excellent bio-compatibility, and largely prolong the blood circulations. The PEG can be introduced through reversible chemical bond, such as Schiff base, electrostatic interactions. Based on the formation of Schiff base between the amine groups in doxorubicin derivatives and aldehyde-PEG-aldehyde, PEG cross-linking would take important roles in tightening the drug-drug particles and improving their stability. Due to the pH-responsive Schiff base, PEG shielding can be rapidly peeled off by acidic pH as soon as arriving tumors. ii) Cell membrane. The cell membrane will be used for encapsulating the F/HAPIN physically. Cell membrane naturally exists in human body, and thus exhibits good biocompatibility. The physiochemical properties of cell membrane coated F/HAPINs are similar to the cells in human body, which will minimize the opsonization, and prolong the blood circulations of our nanoparticles. iii) Hyaluronic acid modification. The hyaluronic acid is negatively charged, it can be introduced on the surface of F/HAPINs through electrostatic interactions. Hyaluronic acid is derived from human body, and may be metabolized like endogenic hyaluronic acid in our body. Otherwise, the hyaluronic acid preferentially targets to the mesenchymal stem cell, which may help us to realize the bone-related tumor therapy. iv) Tumor targeting ligands, like RGD, CRGDK, folic acid, galactose, etc. The ligands can be reacted with the active chemical groups that exposed outside of the F/HAPINs through stimuli responsive bonds. The ligands can help F/HAPINs specifically accumulate in tumor regions. The tumor targeting ligands are mostly composed of natural compounds, like peptides, vitamin, saccharides, etc. and therefore, they are bio-degradable.

The APIs we applied in this patent were all with excellent biocompatibilities. Porphyrin derivatives are natural products, which broadly exist in biological systems. Human blood cells intrinsically contain porphyrins that work on the oxygenation and de-oxygenation of the red cells, and therefore, the porphyrin products will be metabolized similarly with the blood porphyrin. For the chemo-drug APIs, they are performing excellent anti-tumor functionalities, and can be degraded like the normal organic compounds. The surface modifications we introduced are also bio-degradable.

Example 4. Preparation of BTZ-CCM Conjugate 50 mg Bortezomib (BTZ) was dissolved in 10 mL MeOH, and then 59.7 mg curcumin (CCM) was added. The mixture was stirred for 4 h in the dark. The products were purified by silica gel column chromatography. The molecular weight of BTZ-CCM, determined by mass spectrometry, was 717.4, which was the same as calculation result.

Example 5. Preparation of BTZ-CCM Nanoparticles

Figure 6A:
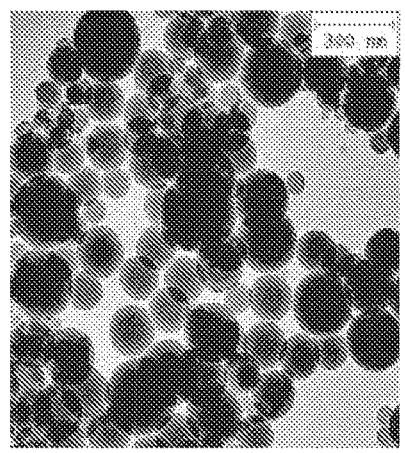
FIG. 6a-b shows TEM image (FIG. 6a) and the size distribution (FIG. 6b) of BTZ-CCM nanoparticles at different pH.
Figure 6B:
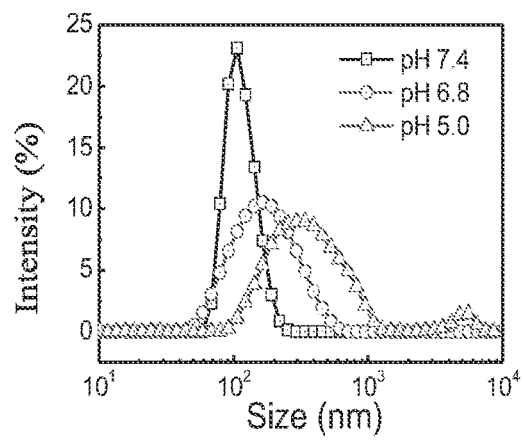

The conjugate from Example 4 (1.18 mg) was dissolved in 1 mL ethanol, and then the solution was added dropwise into 2 mL water under stir. The solution was stirred continuously for 24 h, after the methanol was evaporated, the sample was measured by TEM and DLS (FIG. 6). BTZ-CCM nanoparticles possessed good spherical shape and had favorable dispersibility in water. In addition, the average particle size was about 108 nm (FIG. 6b).

Example 6. Characterization of BTZ-CCM Nanoparticles

Drug Release

Figure 7:
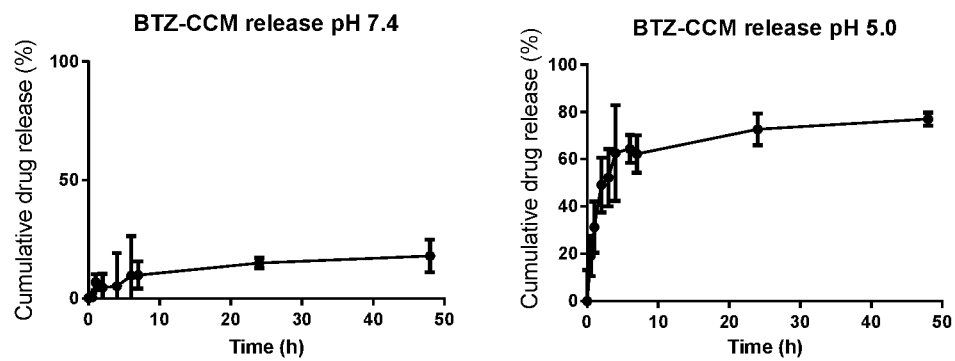
FIG. 7 shows in vitro cumulative release profiles of BTZ from CCM-BTZ nanoparticles at pH 7.4 and 5.0.

The drug release studies of BTZ-CCM nanoparticles were investigated by using dialysis method. The nanoparticle solutions were injected into a dialysis cartridge and dialyzed against PBS at different under room temperature. The BTZ-CCM nanoparticles showed pH sensitive release behavior (FIG. 7), only 15.3% BTZ was released from BTZ-CCM nanoparticles in 48 h when the pH value was 7.4. Meanwhile, up to 88.6% BTZ was released in 48 h when the pH value was 5.0. As is known, boronate ester is responsive to external acid environment by producing boronic acid and diol. Here the BTZ-CCM nanoparticle, containing a boronate ester bond, exhibits a pH-sensitive property, which means the nanoparticle is very stable in physiological neutral condition and could release two parent drugs quickly in acid environment.

In Vitro Cellular Uptake

Figure 8:
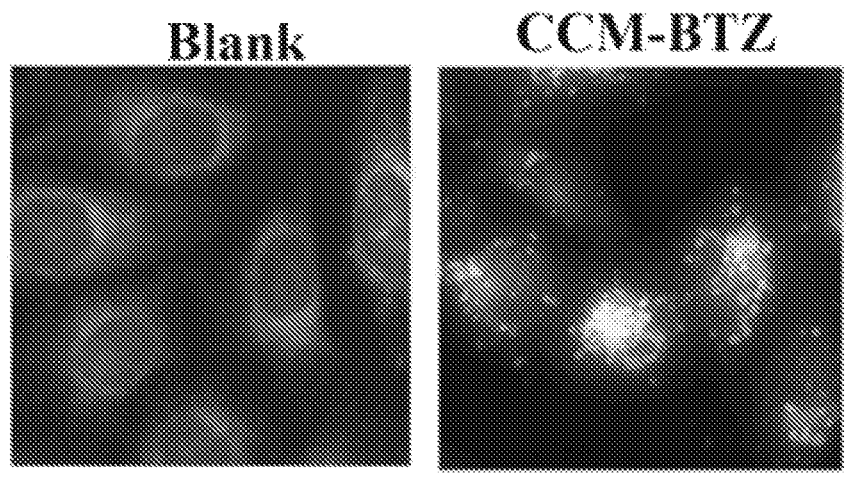
FIG. 8 shows Fluorescence microscope images of RPMI 8226 cells incubated with DID-labeled BTZ-CCM nanoparticles for 4 h.

To verify whether BTZ-CCM nanoparticle can enter cancer cells effectively, cellular uptake study was conducted in RPMI 8226 cell line using the fluorescence imaging method. The tracer DID dye (red) loaded into the BTZ-CCM nanoparticle was used to reveal the location of BTZ-CCM nanoparticles. As shown in FIG. 8, compared with the blank group, the cells incubated by BTZ-CCM for 4 h exhibit strong red fluorescence, which means these nanoparticles can be taken in by RPMI 8226 cells easily.

Cytotoxicity Analysis

Figure 9:
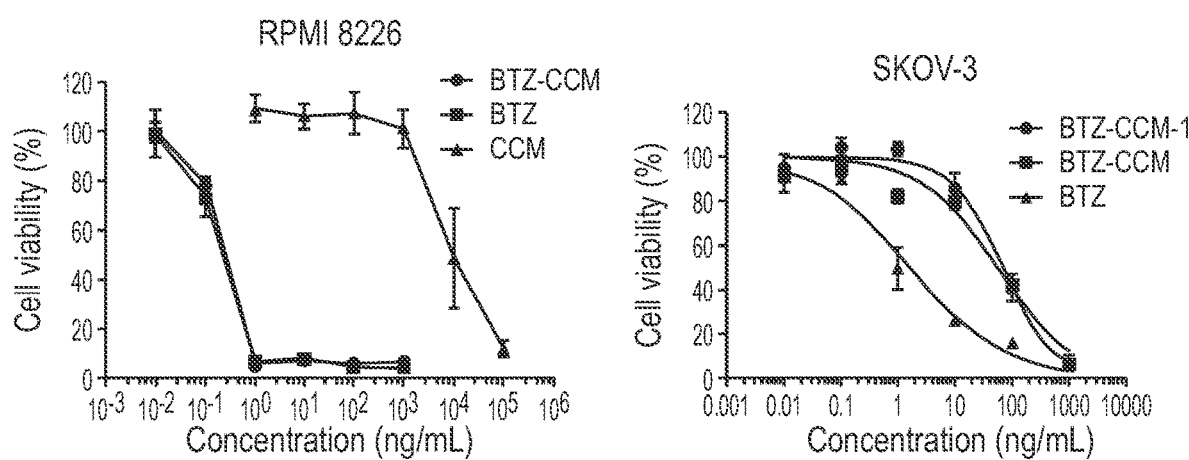
FIG. 9 shows cell viability of RPMI8226 and SKOV-3 cells after a treatment with free BTZ, free BTZ and BTZ-CCM nanoparticles for 48 h.

As a prodrug nanoparticle, BTZ-CCM need to keep an equivalent or similar antitumor activity with the parent drugs, so we investigated cell viability of RPMI 8226 and SKOV-3 cells using the MTS assay after 48 h treatment. As displayed in FIG. 9, the BTZ-CCM nanoparticle could inhibit the proliferation of both cells by a dose-dependent pattern, displaying IC50 values of 0.3 ng/mL and 20 ng/mL for RPMI 8226 cell and SKOV-3 cell, respectively. The curve of BTZ-CCM on RPMI 8226 cell is almost overlapped with BTZ only, though its efficacy decreases a little on SKOV3 cell. Therefore, the final BTZ-CCM nanoparticle shows similar anticancer effect in contrast with the free BTZ.

Example 7. Preparation of Pheophorbide a—Doxorubicin Conjugate

Materials and instruments. Pheophorbide a was bought from Santa Cruz Biotechnology (TX, USA). Doxorubicin was purchased from LC Laboratories (MA, USA). Hydrazine, (1-ethyl-3-(3-dimethyl aminopropyl) carbodiimide hydrochloride) (EDC), N-hydroxysuccinimide (NHS), N, N'-Dicyclohexylcarbodiimide (DCC), 4-Dimethylaminopyridine (DMAP), 2',7'-Dichlorofluorescin diacetate (DCF-DA), $MnCl_2$ and all solvents were purchased from Sigma-Aldrich (MO, USA). Singlet oxygen sensor green (SOSG), Lyso-Tracker Deep Red and CellROX were purchased from Thermo Fisher Scientific Inc. The synthetic compounds were analyzed by Bruker UltraFlextreme matrix-assisted laser desorption/ionization time of flight mass spectrometry (MALDI-TOF-MS), Thermo Electron LTQ-Orbitrap XL Hybrid electrospray ionization mass spectrometry (ESI-MS) and 600 MHz Avance III nuclear magnetic resonance (NMR) spectrometer (Bruker, German). Transmission electron microscopy (TEM) was performed on a Talos L120C TEM (FEI) with 80 kV acceleration voltage. The in vitro laser treatments were conducted under light source that with broader covering area (Omnilux new-U). Cell fluorescence images were captured with a confocal laser scanning microscopy (CLSM, LSM810, Carl Zeiss). The magnetic resonance imaging (MRI) was conducted on a Biospec 7T MRI scanner (Bruker, German). Apoptosis and cell ROS production were evaluated by a BD Fortessa 20 color flow cytometry. Hydroxylated Polyethylene glycol 2000 ($PEG_{2000}$) was purchased from Laysan Bio Inc (AL, USA).

Synthesis of pheophorbide a-hydrazide (Phy). 594 mg pheophorbide a (~1 mmol), 383 mg EDC (2 mmol) and 230 mg NHS (2 mmol) were dissolved in 20 mL dichloromethane (DCM), and vigorously stirred at room temperature for 30 min, then 188 μL anhydrous hydrazine (6 mmol) was added into the reaction system. The reaction was under vigorously stirring at RT for another 4 h. Then, the reaction system was extracted with DCM against water, the pheophorbide a-hydrazide (Phy) were distributed in DCM.

Synthesis of pheophorbide a-hydrazide-doxorubicin (PhD). 121.4 mg Phy (0.2 mmol) and 58 mg doxorubicin hydrochloride (0.1 mmol) with a drop of TFA (20 μL) were dissolved in 10 mL methanol, and stirred overnight under 50° C. The target compound (PhD) was purified by column chromatography.

Example 8. Preparation of Pheophorbide a—Doxorubicin Pegylated Nanoparticles Synthesis and characterization of dual-aldehyde terminated PEG. 570 mg 4-Formylbenonic acid (5 mmol) and 206 mg DCC (7 mmol) were dissolved in anhydrous (DCM), the mixture was stirred at 0° C. for 30 min until plenty of white precipitates were observed. Then, 1000 mg hydroxylated $PEG_{2000}$ (0.5 mmol) and 73 mg DMAP (0.6 mmol) in 10 mL anhydrous DCM was added. The resulting mixture was stirred at ambient temperature for 24 h. The dual-aldehyde terminated PEG was purified by precipitation via cold ether, and further dialyzed with a dialysis tube (MWCO is 1,000 Da). The solution was then lyophilized.

Preparation and characterization of PEGylated PhD NPs (pPhD NPs). The nanoparticles were prepared by the following typical re-precipitation method. Briefly, 50 mmol PhD DMSO solution was firstly made, and 2 μL PhD solution was then dropped into 998 μL Milli Q water under sonication, followed by a 3~5 s vortex, resulting in the unPEGylated PhD NPs. Then, 100 μM dual-aldehyde terminated PEG were added, and stirred under ambient temperature for 48 h, resulting in the pPhD NPs. The size distributions, polydispersity index and surface charge of the nanoparticles were carried on with a dynamic light scattering (DLS, Zetasizer, Nano ZS) from Malvern Instruments Ltd (Worcestershire, UK.). The morphology of NPs was observed by a Talos L120C TEM (FEI) with 80 kV acceleration voltage. The TEM samples were prepared by dropping aqueous nanoparticle solution (50 μM) on copper grids and naturally dried under room temperature.

Example 9. Preparation of $Mn^{2+}$ Chelated Pheophorbide a—Doxorubicin Conjugate Preparations of $Mn^{2+}$ chelated pPhD NPs. $Mn^{2+}$ chelation was performed following the published method. Briefly, 24.3 mg Phy (40 μmol) and 25.2 mg $MnCl_2$ (200 μmol) were dissolved in 2 mL methanol with 200 μL pyridine, and the reaction was refluxed for 2 h. The $Mn^{2+}$ chelated Phy was purified by extraction (DCM against water) for 5 times. The un-chelated $Mn^{2+}$ dissolved in Milli Q water and was removed. The $Mn^{2+}$ chelated Phy stayed in organic layer (DCM), and was dried with a rotavapor. Then, the manganese ion chelated Phy was employed to synthesize PhD monomers and fabricate the pPhD NPs with the procedures mentioned above.

Example 10. Characterization of Pheophorbide a—Doxorubicin Conjugates & Nanoparticles Methods Optical measurements of the materials. The UV-vis spectra were collected with a UV-vis spectrometer (UV-1800, Shimadzu). For all materials and compounds, the absorbance was collected under a range of 200 nm to 800 nm. The fluorescence spectra were obtained by a fluorescence spectrometer (RF-6000, Shimadzu). For Phy, the excitation of 412 nm was used, and for DOX, the excitation was set to 488 nm. To test the fluorescence properties of PhD monomer or nanoformulation, both excitations were employed.

Critical aggregation concentrations (CAC) assessment. Pyrene molecules were employed as an indicator to determine the CAC of nanoparticles by comparing the fluorescence of their third and the first emissive peaks ($I_3/I_1$) Briefly, 999 μL pPhD NPs samples with different concentrations were prepared, and 1 μL of 0.1 mM pyrene solution (in acetone) was introduced into pPhD NPs suspension and yielded 0.1 μM pyrene solution. The pPhD NPs and pyrene contained solutions were incubated under 37° C. for 2 h. The fluorescence of pyrene in different concentrations of pPhD NPs (excitation is 335 nm) was tested, the $I_3/I_1$ values were recorded for CAC assessment.

Near-infrared fluorescence imaging (NIRFI) of pPhD NPs. 10 μL PhD monomers and pPhD NPs with varied concentrations were dropped on a transparent film respectively, and put in the NIRFI chamber, and their NIRFI was collected by using a Kodak multimodal imaging system IS2000MM with an excitation at 625±20 nm and an emission at 700±135 nm. The PhD monomers were obtained by dissolve PhD molecules in good solvent (DMSO).

Photothermal and photodynamic effects of pPhD NPs. For photothermal effect evaluation, different concentrations of pPhD NPs were placed in 96-well plate, and exposed under 0.4 w/cm² laser (λ=680 nm) for 3 min. The heat generations were recorded by FLIR thermal camera. Reactive oxygen species (ROS) production was tested for photodynamic effect evaluation with a commercial probe, singlet oxygen sensor green (SOSG). Briefly, different concentrations of pPhD NPs were incubated with SOSG working solution, and irradiated by an incident laser (680 nm. 0.4 w/cm²) for 3 min. SOSG probe dissolved in water at the same concentration was set as blank control by treated with same dose of laser. The fluorescence readouts of SOSG was monitored by microplate reader (SpectraMax M2, Molecular Devices) to relatively qualified the photodynamic effect.

Accumulated drug release of pPhD NPs triggered by acidic pH and laser. 100 μM pPhD NPs were prepared and loaded into dialysis cartridges (MWCO is 3,500 Da) to determine the accumulated drug release profile. The cartridges were submerged into 1000 mL PBS (pH 7.4) and acidized PBS (pH 5.0) respectively, and stirred with a moderate-speed at ambient temperature. The laser-triggered drug release was conducted by irradiation with laser at 0.4 w/cm² for 3 min before the dialysis. The DOX remained in the dialysis cartridge was drawn with a micro-syringe at various time-points, and quantitatively measured by the UV-vis absorbance of DOX. Each value was reported as the means of the triplicate samples.

Cell uptake assay. Since the fluorescence of Phy and DOX were both quenched in pPhD NPs, the cell uptake of pPhD NPs may not be accurately measured if the measurements were conducted under the aqueous circumstance. To evaluate the cell internalization of pPhD NPs and their post-transformed counterparts (pre-treated with pH 6.8 to achieve size/charge dual-transformability). pPhD NPs and post-transformed pPhD NPs were incubated with OSC-3 cells for 3 h, respectively, and then the cells were detached and collected in a vial. After removing the medium, the OSC-3 cells were dissolved with the same volume of DMSO to dissolve the cells and completely dissolved all materials that related to pPhD NPs. The solutions were then evaluated by fluorescence spectrometer to test the fluorescence of DOX. The DOX solution concentrations represent the cellular uptake of the pPhD NPs. Each value was reported as the means of the triplicate samples.

Reactive oxygen species (ROS) assay in cellular level. OSC-3 cells were seeded in 6-well plates with 5.0×10⁵ cells per well, and cultured for 24 h until fully attached. The cells were treated with Phy, pPhD (pH 7.4) and pPhD (pH 6.8) for 3 h. The cells were then incubated with DCF-DA (10 μM) for another 30-min followed by light treatment for 1 min and analysis by flow cytometry. Cells without any treatment were used as a control. The concentrations of all materials were set as 10 μM.

Apoptosis assay. OSC-3 cells were seeded in 6-well plates with 5.0×10⁵ cells per well, and cultured for 24 h until all cells become fully attached. The cells were treated with DOX, Phy, pPhD (pH 7.4) and pPhD (pH 6.8) for 3 h, then applied for light treatment for 1 min. Cells without any treatment were set as a control. Twenty-four hours later, cells were stained with Annexin V-FITC/PI, and the apoptosis was measured by flow cytometry as described previously. The concentrations of all materials were set as 10 μM.

Lysosomes colocalization assay. OSC-3 cells were incubated with 20 μM pPhD NPs for 4 h, then stained with Lysotracker Deep Red for confocal laser scanning microscopy (CLSM) observation. The fluorescence spectrum of Lysotracker Deep Red overlapped with that of Phy, but the fluorescence readouts were much higher than Phy under Cy5 tunnel. We therefore adjusted the parameters of CLSM until we could not observe the fluorescence of Phy in pPhD NPs treated cells, and used these parameters to observe the fluorescence of Lysotracker Deep Red to avoid the interference of Phy. For DOX distribution, standard FITC channel was used.

Cell spheroids penetration of the nanoparticles. OSC-3 cells were seeded in the round-shape bottom 96-well plate at a density of 10⁴ cell per well. Cell spheroids were treated with 20 μM pPhD (pH 7.4) and 20 μM post-transformed pPhD (pH 6.8). The penetrations of the nanoparticles were monitored by a confocal laser scanning microscopy.

Phototherapeutic effect on cells. OSC-3 cells were seeded in 8-well chamber slide with 5.0×10⁴ cells per well, and cultured for 24 h until all cells were completely attached. The cells were then treated with 10 μM pPhD NPs for 3 h. Cells without any treatment were used as a control. Both treatments were exposed to light for 1 min. After light treatments, cells were stained with propidium iodide (PI) and DiOC₆ (3) as described previously. Confocal laser scanning microscopy was employed to monitor the photo-cytotoxicity to cells.

Pharmacokinetics evaluation. The jugular vein of male Sprague-Dawley rats was cannulated and a catheter was implanted for intravenous injection and blood collection (Harland, Indianapolis, Ind., USA). pPhD NPs (10 mg/kg), upPhD NPs (10 mg/kg) and free DOX (4.7 mg/kg) were i.v. administrated into rat (n=3). Whole blood samples (~100 μL) were collected via jugular vein catheter before dosing and at predetermined time points post injection. The kinetics of all materials were measured through testing the fluorescence of 591 nm (excitation is 488 nm). The values were plotted versus time after the subtraction of blood background.

Establishment of OSC-3 tumor-bearing animal models and treatment schedule. Female athymic nude mice (6 weeks old) were purchased from Harlan (Livermore, Calif., USA). All animal experiments were strictly in compliance with the guidelines of Animal Use and Care Administrative Advisory Committee of University of California, Davis. The subcutaneous tumor models were established by inoculated OSC-3 cells (5×10⁶ cells per tumor) into both flanks of the nude mice. The orthotopic models were established by inoculating OSC-3 (5×10⁶ cells per mouse) to the lips of the mice. After the subcutaneous tumors reached about 100 mm³ and orthotopic tumors reached about 50 mm³, mice were divided into five groups (n=6): control (PBS), free drug (DOX), free photosensitizer (Phy), un-PEGylated PhD NPs (upPhD NPs) and PEGylated PhD NPs (pPhD NPs). The mice received materials via i.v. injection through the tail vein. The dose of DOX was 4.7 mg/kg, Phy was 5.3 mg/kg, upPhD NPs and pPhD NPs were both 10 mg/kg. The concentrations of Phy and DOX were determined by calculating their contents in PhD monomers. Phy takes 53% content in PhD monomers, and DOX is 47%. The concentrations for pPhD NPs were calculated based on the concentrations of PhD monomers, the amounts of PEG were excluded. In subcutaneous models, the right tumors were subjected to laser exposure (0.4 w/cm$^2$, 3 min), and the left-side tumors were not treated with laser (to evaluate the efficacy of chemotherapy). In the orthotopic models, all the tumors that treated with photosensitizer, including Phy, upPhD NPs and pPhD NPs, were treated with laser (0.4 w/cm$^2$, 3 min). The laser treatments were introduced twice, at 24 h and 48 h after the i.v. injection. During the laser treatments, the photothermal effects were monitored and recorded by a FLIR infrared camera (FLIR Systems, Boston, Mass.).

In vivo ROS production. Orthotopic tumor-bearing mice were assigned into 4 groups (n=3): 1) PBS, 2) Phy, 3) upPhD NPs and 4) pPhD NPs. 5.3 mg/kg Phy, 10 mg/kg upPhD NPs and 10 mg/kg pPhD NPs were i.v. administrated into mice respectively. 24 h later, tumors of the mice were irradiated with 0.4 w/cm$^2$ laser for 3 min. The mice were sacrificed and the tumor was collected for NIRFI (Pre-cellROX). After the NIRFI, the tumors were immediately sunk into ROS probe solution (CellROX) for 10 s, and conducted for another NIRFI (Post-cellROX). The in vivo ROS production was presented by fluorescence intensities of "Post-cellROX" deducted the fluorescence in "Pre-cellROX" tumours. The Phy signals were overlapped with cellROX, we deducted the NIRF of Phy (Pre-cellROX) from the final imaging results (Post-cellROX) to determine the ROS production.

Biodistribution of the nanoparticles. 10 mg/kg upPhD NPs and 10 mg/kg pPhD NPs were i.v. administrated to orthotopic mice respectively. The tumors were then exposed to the laser at 24 h after the materials treatments. After the laser trigger, whole body imaging was acquired at indicated time points post-injection. After in vivo imaging, animals were sacrificed, and tumors and the major organs were harvested for ex vivo imaging.

Real-time monitoring the time-dependent tumor accumulation and the phototherapeutic effect pPhD NPs by MRI. For time-dependent tumor accumulation measurement, the orthotopic tumor models were i.v. injected with pPhD NPs (10 mg/kg, Mn$^{2+}$ dose: 0.01 mmol/kg), and the tumor area was monitor by a Bruker Biospec 7T MRI scanner using T1-weighted Multi-Slice Multi Echo (MSME) sequence (echo time (TE)/repetition time (TR) 14/500 ms) using a 512×512 matrix size. For monitoring the phototherapeutic effect, the OSC-3 tumor-bearing mice were treated with pPhD NPs (i.v. injection, 10 mg/kg), then the tumor site was exposed under continuous laser (0.8 w/cm$^2$ for 3 min) at 24 h and 48 h after i.v. injection. The tumor conditions were monitored by MRI in real-time with the same parameters as that in tumor accumulation experiment.

Tumor volume and body weight measurements. The body weights and tumor sizes were monitored three times a week, and the tumor volume was calculated by the following formula: Tumor volume=Length×(Width/2)$^2$.

H&E evaluation. All laser-treated tumors were collected and stained with hematoxylin and eosin (H&E) to evaluate the effect of phototherapy. The main organs of each group, including heart, liver, spleen, lung, kidney, small intestine, were collected for H&E assay to evaluate the toxicity of the materials.

Results

Figure 10A:
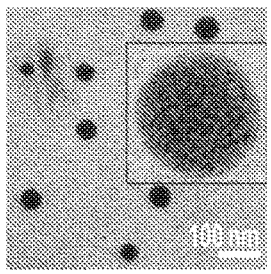
FIG. 10a-i shows characterization of pPhD NPs.
Figure 10B:
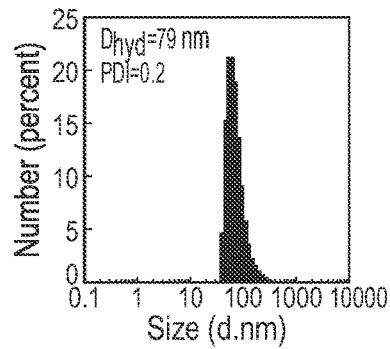
Figure 10C:
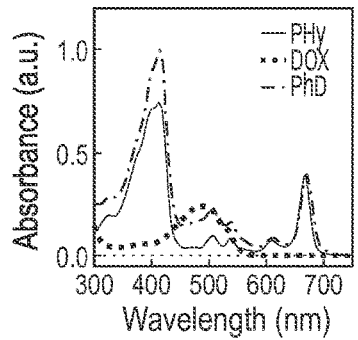
Figure 10D:
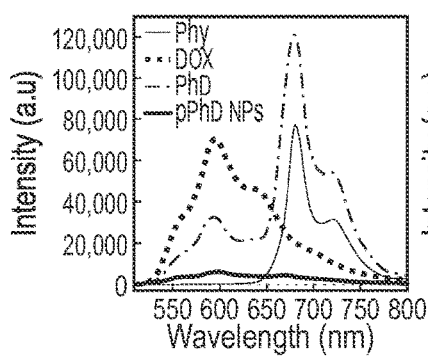
Figure 10E:
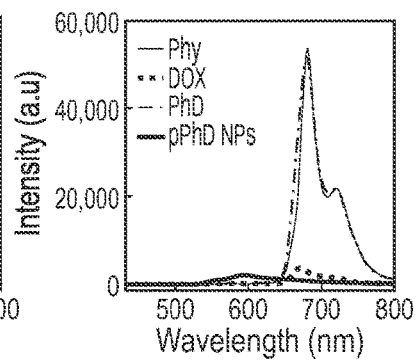

The hydrodynamic size of the pPhD NPs was around 79 nm, with a polydispersity index (PDI) of 0.2 (FIG. 10a). TEM micrograph (FIG. 10b) demonstrated that the pPhD NPs were in spherical morphology, within which revealed a cluster of small dark dots. These small dots are believed to be a micellar assembly of PhD monomers, which further self-assembled into larger nanoaggregates through multimicelle aggregation. In pPhD NPs, the content of DOX was ~24.9% (w/w) while that of photosensitizer (Phy, Phy is Pa with a hydrazide pendant) was ~28.4% (w/w) as calculated by UV-vis absorbance. The critical aggregation concentrations (CAC) of pPhD NPs were calculated to be 3 μM. The UV-vis spectra (FIG. 10c) of PhD monomers showed elevated absorbance of DOX around 488 nm and Phy peak around 412 nm and 670 nm, indicating the PhD monomer contained both Phy and DOX. The fluorescence spectra (FIG. 10d) showed that the emission of DOX was at ~590 nm, and that of Phy was at ~680 nm. While being conjugated together, the fluorescence of DOX at 590 nm decreased, and that of Phy at 680 nm increased, indicating a fluorescence resonance energy transfer may occur in PhD monomers. In nano-formulation (pPhD NPs), aggregation caused quenched (ACQ) phenomenon dominated and quenched both fluorescence of Phy and DOX (FIG. 10e).

Figure 10F:
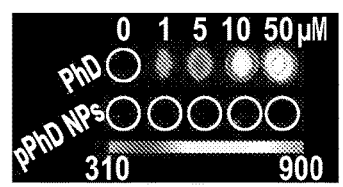
Figure 10G:
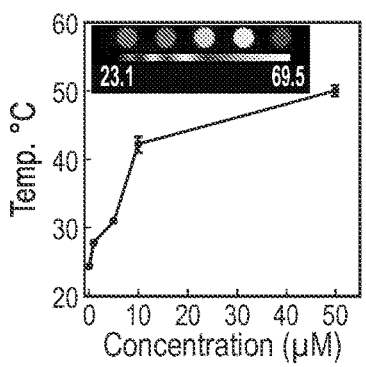
Figure 10H:
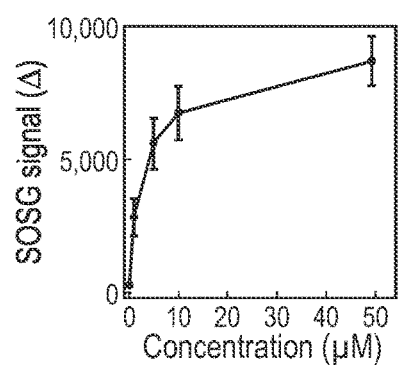
Figure 10I:
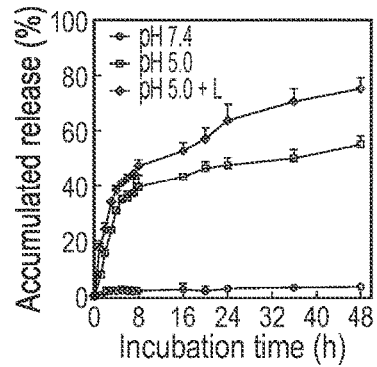

Near infra-red imaging, photothermal and photodynamic effect of pPhD NPs. Since porphyrin derivatives are intrinsically suitable for near infra-red imaging (NIRFI), the NIRFI capacity of the PhD monomers and its nano-formulation (pPhD NPs) was evaluated in an animal imaging system. The PhD monomer exhibited excellent fluorescence signal (FIG. 10f), indicating it was appropriate for NIRFI. The pPhD NPs showed very low fluorescence due to the occurrence of ACQ, which was consistent with the results from the fluorescence spectra (FIG. 10e). FIG. 10g showed that the temperature of pPhD NPs increased to around 50° C. upon laser irritation, demonstrating their excellent photothermal property. Furthermore, the pPhD NPs could produce considerable reactive oxygen species (ROS) in a concentration-dependent manner (FIG. 10h).

pH stimulus drug release of pPhD NPs. The hydrazone bond could be cleaved at pHi inside tumor cells. Therefore, the pPhD NPs were designed to release the drug under the stimulation of acidic pH and/or laser. The accumulated drug releasing pattern of pPhD NPs was shown in FIG. 10i. The nanoparticles were stable in physiological pH with minimal drug release. The release could be significantly accelerated in acidic pH (5.0, mimicking the lysosomes pH) that closed to pHi. While triggered with both laser and acidic pH, the nanoparticles could release the drug even faster and the accumulated drug release rate reached nearly 80% within 48 h. The drug-releasing pattern supported that the pPhD NPs could stay stable in physiological conditions, but effectively release the drug under specific stimuli (pH and/or laser).

Size/charge dual-transformability of pPhD NPs. We hypothesized that the ultra-small nanoparticles that constrained in pPhD NPs would be released after the peeling of the PEG-surface in the TME, as the Schiff base used for PEGylation/cross-linkage was ultra-sensitive to pHe. To prove this hypothesis, pPhD NPs were incubated at pH 6.8 for different time, and their "Trojan Horse" behaviors were directly observed by TEM (FIG. 11a). At the very beginning, pPhD NPs were stable, and able to accommodate hundreds of ultra-small nanoparticles, indicating that the "soldiers" were sheltered and retained in the "Trojan Horse". While the pPhD NPs could still be observed at 1 h, most ultra-small nanoparticles were released. At 12 h, all ultra-small nanoparticles (~4 nm) were released (FIG. 11a). The TEM micrographs demonstrated that the pPhD NPs were stable enough to retain the ultra-small nanoparticles under normal physiological condition, but could effectively release ultra-small nanoparticles in response to pHe in TME. The changes in surface charges further confirmed the PEGylation and de-PEGylation (FIG. 11b). Before PEGylation, the nanoparticles (upPhD NPs, un-PEGylated PhD NPs) exhibited strongly positive charge (43 mV). While after PEGylation, the surface charge decreased to 12 mV. When the pPhD NPs were treated at pH 6.8, the charge rebounded to 35 mV. The results of TEM and surface charge studies supported that pPhD NPs were dual-transformable, both size and surface charge could be transformed to desirable values that may be beneficial to superior tumor penetration (ultra-small size) and enhanced cell uptake (strong positive charge).

Transformability-enhanced cellular uptake, ROS production and apoptosis in vitro. Furthermore, we investigated the benefits of the dual-transformability of pPhD NPs in oral squamous cell carcinoma 3 (OSC-3) cells. The cellular uptake was evaluated for both pPhD NPs and post-transformed pPhD NPs (incubated at pH 6.8 to realize dual-transformability). As shown in FIG. 11c, the post-transformed pPhD NPs (at pH 6.8) showed significantly higher cell uptake than that at pH 7.4. We then evaluated the ROS production in OSC-3 cells, and found that the post-transformed nanoparticles (pPhD NPs at pH 6.8) produced significantly higher amount of ROS in comparison to free photosensitizer (Phy) and the nanoparticles at pH 7.4 (FIG. 11d). The cell apoptosis assays showed consistent results. Post-transformed pPhD NPs exhibited more significant apoptosis than their counterpart at pH 7.4 and other control groups (FIG. 11e).

Tumor penetrations and lysosome-colocalization of the pPhD NPs. The pPhD NPs could transform to nanoparticles with ultra-smaller size that may penetrate deeper in tumor tissue than the particles with larger size. To prove it experimentally, pPhD NPs and post-transformed pPhD NPs were incubated with OSC-3 cell spheroids respectively, and observed under confocal microscopy (FIG. 11f). In pPhD NPs treated spheroids, the fluorescence of DOX and Phy were both distributed at the periphery at the first 3 h, then diffused further at a prolonged incubation time (24 h). Upon transformation into ultra-small nanoparticles (pPhD NPs at pH 6.8), the fluorescence signal spread much further than that at neutral pH at the first 3 h, then diffused throughout the whole tumor spheroid after 24 h incubation. This result indicated that the ultra-small nanoparticles could penetrate much deeper into the spheroids than the bigger nanoparticles. After the nanoparticles have been ingested into the tumor cells, the pPhD NPs were expected to release the drug (DOX) upon the cleavage of hydrazone bonds by pHi inside the lysosomes. We incubated pPhD NPs with OSC-3 cells, and co-localized the fluorescence of DOX (green) with lysosomes (red). As shown in FIG. 11g, DOX showed large co-localization areas with lysosomes, indicating that our nanoparticles could release DOX in lysosomes, in which the pHi enabled cleavage of the hydrazone bond.

In vitro controllable phototherapy of pPhD NPs. We then irradiated a discrete area of OSC-3 cells pre-incubated with pPhD NPs, and observed the laser treated and non-treated cells (FIG. 11h). Most of OSC-3 cells treated with pPhD NPs & laser were dead as indicated by PI staining, while the cells incubated with pPhD NPs without laser treatment, exhibited much less cell death. As a control group, the PBS treated cells showed no obvious cell death, in both regions exposed or not exposed to laser. These results indicated that the phototherapy with pPhD NPs was controllable, only impacted on the region where the laser was directed.

Synergistic effect of phototherapy and chemotherapy. The synergistic effect of the chemotherapy and phototherapy of pPhD NPs was evaluated. OSC-3 cells were incubated with different concentrations of free photosensitizer (Phy), free chemotherapeutic drug (DOX) and pPhD NPs, respectively, then treated with or without laser (FIG. 11i). In the non-laser treated group, free Phy exhibited no obvious cytotoxicity while free DOX and pPhD NPs showed notable anti-tumor efficacy. In the laser-treated group, Phy exhibited enhanced efficacy comparing to the non-laser treated counterpart. The cell-killing effect of DOX remained at a similar level. It is worth noting that the pPhD NPs treated group showed the most effective anti-tumor activity against OSC-3 cells among all the groups with or without laser treatment. We then calculated the combination index (CI) of the phototherapy and chemotherapy based on FIG. 11i, and demonstrated that these therapeutic modalities showed excellent synergistic effect to kill the cancer cells (FIG. 11j).

Figure 12:
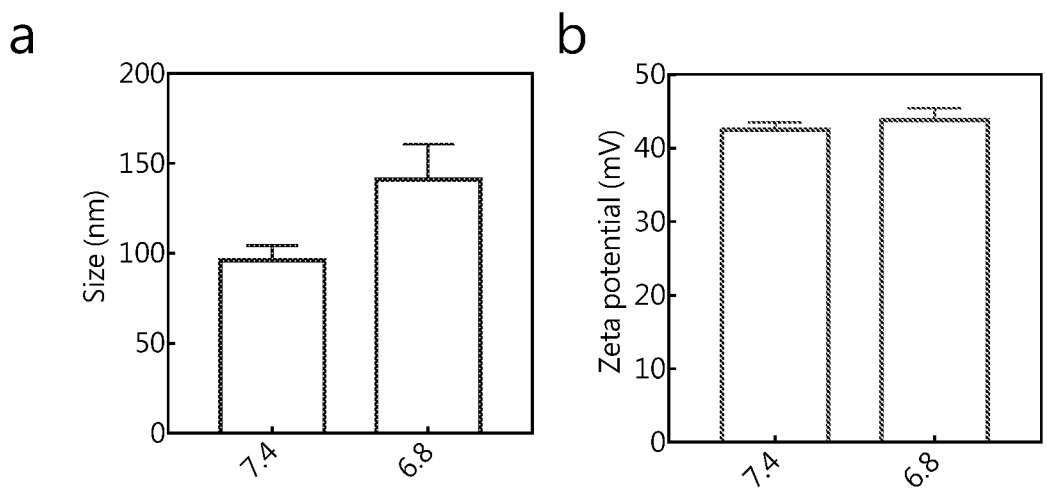
FIG. 12a-b shows FIG. 12a) size and FIG. 12b) surface charge changes of upPhD NPs (50 µM), before (7.4) and after (6.8) being treated with acidic pH.

Oral cancer commonly occurs at sites of the lips, tongue, cheeks, floor of the mouth, hard and soft palate, sinuses, and pharynx, and is readily accessible to light. It represents an excellent clinical situation for the potential applications of pPhD NPs developed in this study. We then investigated whether the dual-transformability of pPhD NPs could greatly improve delivery efficiency in orthotopic oral cancer models established by implantation of OSC-3 cells into the lips of nude mice. To demonstrate the importance of the dual-transformability of pPhD NPs, we employed the un-PEGylated PhD NPs (upPhD NPs), which possessed neglectable size/charge transformability (FIG. 12a and FIG. 12b), and therefore could be considered as non-transformable, control nanoparticles to pPhD NPs.

Figure 13:
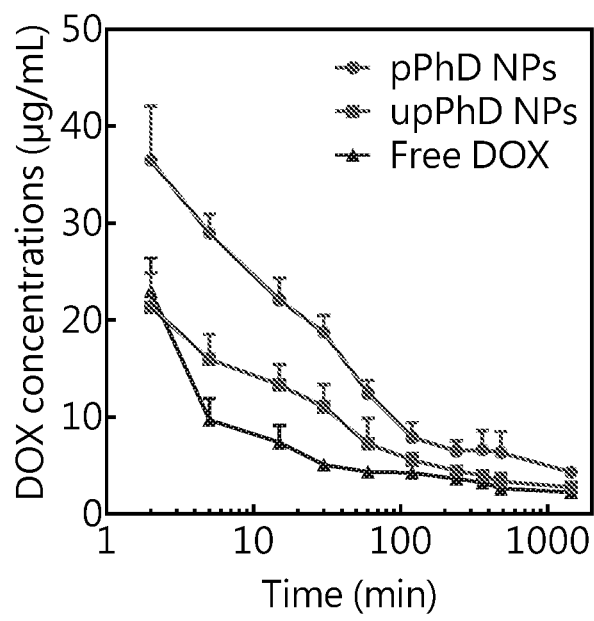
FIG. 13 shows Pharmacokinetics of pPhD NPs, upPhD NPs, and free DOX. By calculation, the area under curve (AUC) of pPhD NPs was 9258, upPhD NPs was 5501 and free DOX was 4161.

Pharmacokinetics evaluations of pPhD NPs. The pharmacokinetic study of pPhD NPs was evaluated in jugular vein cauterized rats, and an equal dose upPhD NPs and free DOX were served as the control (FIG. 13). Blood was collected at several time points following i.v. injection, and drug concentrations were based on the quantification of DOX's fluorescence. As expected, the PEGylated formulation (pPhD NPs) showed longest blood circulation time, which was 1.68 times than the un-PEGylated counterpart (upPhD NPs) and 2.22 times than the free drug (DOX). The pharmacokinetics behaviours suggested that pPhD NPs exhibited longer blood circulation time, which may provide a longer window for drug to interact with cancers.

Figure 14A:
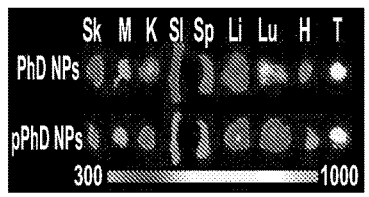
FIG. 14a-j shows in vivo evaluation of pPhD NPs in orthotopic oral cancer models.
Figure 14B:
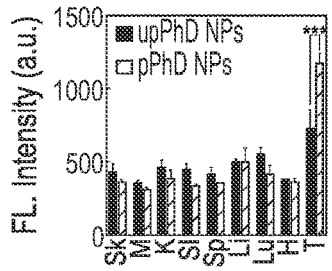

NIRFI evaluation of in vivo biodistribution of pPhD NPs on orthotopic oral tumor models. The in vivo NIRFI of upPhD NPs and pPhD NPs were conducted on orthotopic oral tumor model. Both nanoparticles preferentially accumulated at tumor site. The ex vivo NIRFI further confirmed that their higher accumulation in tumors than in normal organs (FIG. 14a). The fluorescence signal of pPhD NPs in the center of the tumor was much stronger than that of upPhD NPs. The quantitative fluorescence comparison (FIG. 14b) showed that pPhD NPs exhibited significantly higher tumor accumulation than its un-PEGylated counterpart (upPhD NPs).

Figure 14C:
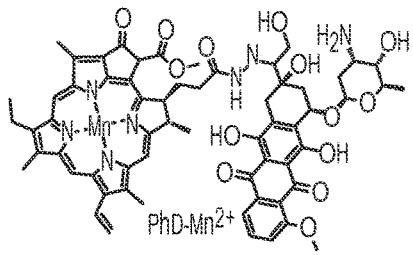
Figure 14D:
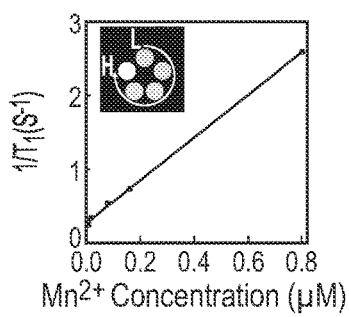
Figure 14E:
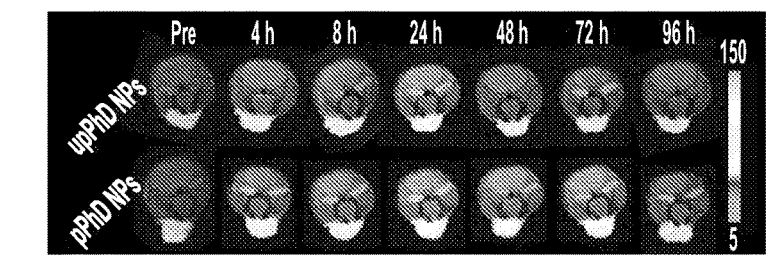
Figure 14F:
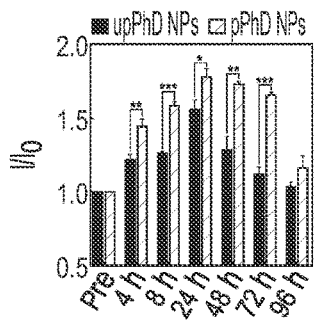
Figure 14G:
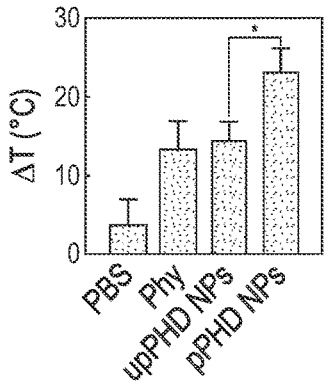

Time-dependent tumor accumulation of pPhD NPs visualized by MRI. In contrast to optical imaging, MRI has superior features, like deeper penetration. MRI also offers excellent spatial and anatomic resolution. As pPhD NPs have intrinsic capability to chelate manganese (II) ion ($Mn^{2+}$) (FIG. 14c), we could conveniently utilize MRI to visualize the tumor accumulation of the nanoparticles in real time. The T1 MRI contrast of PhD NPs was concentration-dependent (FIG. 14d) and the relaxivity ($r^1$) of $Mn^{2+}$ chelated PhD NPs was calculated to be 2.89 $mM^{-1}$ $S^{-1}$. The dynamic contrast-enhanced MR images in orthotopic oral cancer models were displayed in FIG. 14e. The T1-weighed MR signal at tumor sites showed a time-dependent manner with the MR signal intensity increased after injection of the nanoparticle, reached a peak at 24 h, then gradually decreased. Interestingly, the MR signals of pPhD NPs were significantly higher than the non-transformable nano-formulation (upPhD NPs) at 4 h, 8 h, 24 h, 48 h, and 72 h post-injection (FIG. 14e & FIG. 14f). The MR signals of pPhD NPs retained at tumor sites at a considerable level for up to 72 h. The results from NIRFI and MRI studies suggested that the pPhD NPs possessed superior accumulation and penetration properties in orthotopic oral cancer models.

Figure 14H:
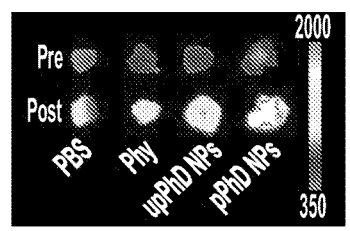
Figure 14I:
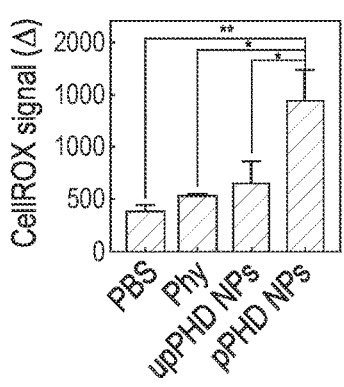

Investigation of the in vivo phototherapeutic effects. The phototherapeutic effects of pPhD NPs were investigated on the orthotopic oral cancer model. As shown in FIG. 14, the photosensitizer harbored groups all exhibited better photothermal effect than PBS control as measured by the temperature rises at the tumor site. Among these groups, pPhD NPs exhibited highest heat generation, and the temperature of the tumors treated with pPhD NPs increased about 24° C. FIG. 14h and FIG. 14i displayed the photodynamic effects, in which pPhD NPs treated group produced significantly more ROS production than other three groups.

Figure 14J:
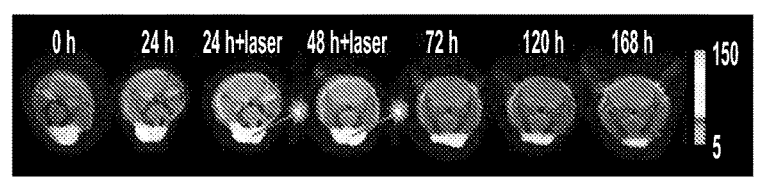

Phototherapeutic outcomes of PhD NPs visualized by MRI. MRI was further employed for in situ monitoring the in vivo therapeutic efficacy of pPhD NPs (FIG. 14j). The T1 MRI contrast at tumor site increased dramatically at 24 h post-injection pPhD NPs. Tumors were then treated twice with laser at 24 h and 48 h post-injection. MRI was used to continuously assess the treatment outcomes. MR image at 72 h showed significant tumor shrinkage and a large volume of necrotic tissue at the tumor site. The tumor kept on shrinking with time elapse, and the majority of tumor was ablated at 7 days of post-injection. The MRI visualization showed promising merits for evaluation of the therapeutic effects that cannot be observed by naked eyes, especially for the tumor that cannot be directly reachable.

Figure 15A:
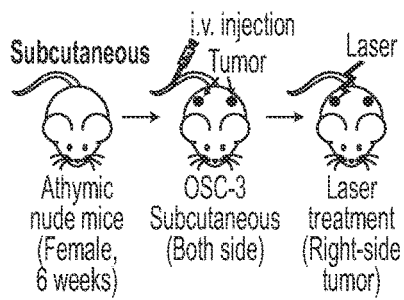
FIG. 15a-j shows therapeutic effects of the nanoparticles. The establishment of (FIG. 15a) subcutaneous and (FIG. 15b) orthotopic oral tumor models (n=6), and the subsequent treatments with PBS, 4.7 mg/kg DOX, 5.3 mg/kg Phy, 10 mg/kg upPhD NPs and 18.7 mg/kg pPhD NPs (contains 10 mg/kg PhD monomer), respectively. The doses of free DOX and Phy were equivalent to those in upPhD NPs and pPhD NPs groups, respectively. The laser (680 nm) doses were all set as 0.4 w/cm2 for 3 min.
Figure 15C:
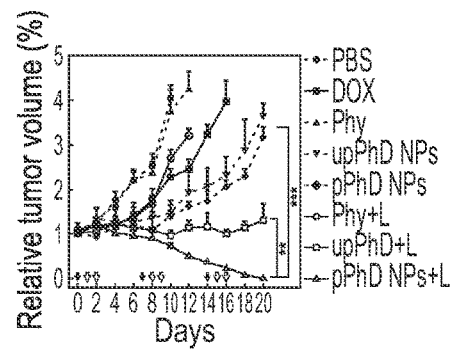
Figure 15D:
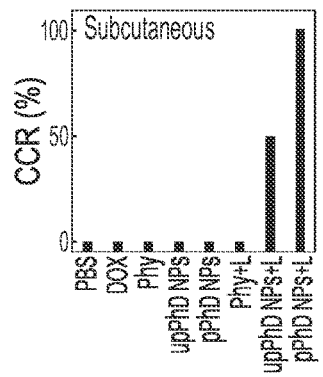
Figure 15B:
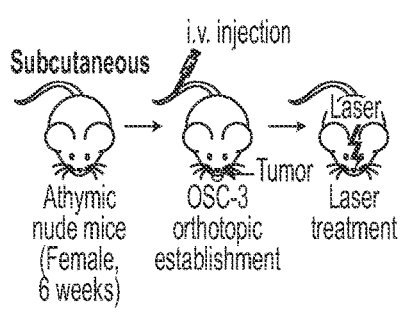
Figure 15E:
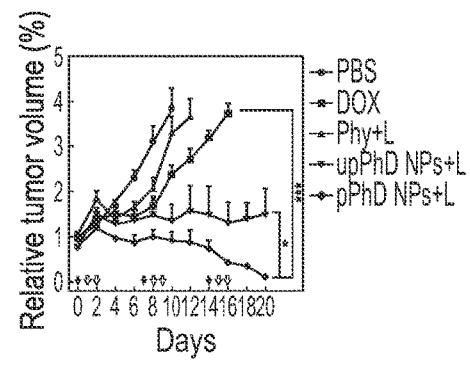
Figure 15F:
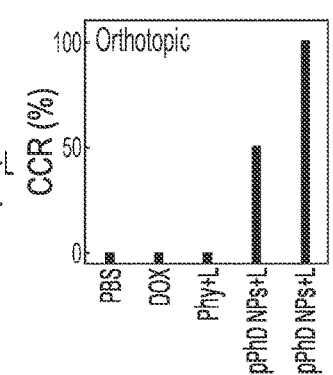
Figure 15G:
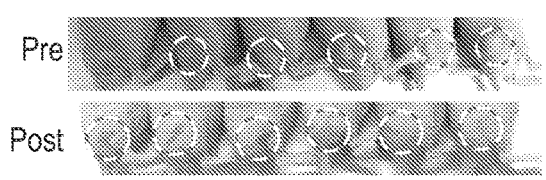
Figure 15I:
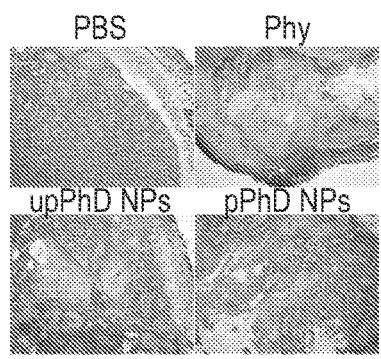
Figure 15H:
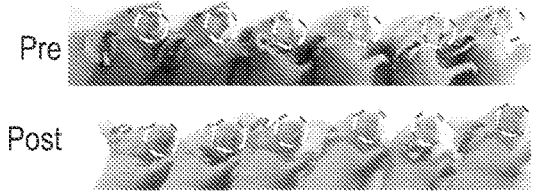

In vivo therapeutic effects of pPhD NPs and their counterparts. We further performed systematic treatment studies in both subcutaneous and orthotopic tumor models to verify the synergistic therapeutics and superior efficacy of pPhD NPs. The OSC-3 cells were implanted to two positions of the flanks or lips of nude mice to establish subcutaneous and orthotopic tumor models, respectively. After tumor formation at 15 days, the mice were randomly assigned into 5 groups (n=6): control (PBS), free drug (DOX), free photosensitizer (Phy), un-PEGylated PhD NPs (upPhD NPs) and PEGylated PhD NPs (pPhD NPs). All tumor-bearing mice were treated once per week for 3 consecutive weeks by i.v. administration. In subcutaneous models (mice bearing two tumors), the right tumors that treated with photosensitizer harbored materials were subjected to laser exposure (0.4 w/cm², 3 min), and the left-side tumors were not treated with laser to evaluate the efficacy of chemotherapy alone (FIG. 15a). In the orthotopic models, all tumors treated with photosensitizer harbored materials were treated with laser (FIG. 15b). The laser treatments were given twice at 24 h and 48 h after the i.v. injection. Tumor volumes and body weights were measured throughout the treatments. The changes in tumor volume of the subcutaneous model were shown in FIG. 15c. Since the oral cancer is highly malignant, the PBS and free photosensitizer (without laser) groups didn't exhibit obvious antitumor efficacy. The tumor grew fast and all mice in these two groups were sacrificed (considered dead) due to the oversized tumors within 2 weeks. The free photosensitizer with laser (Phy+L) and free chemo-drug (DOX) exhibited moderate anti-tumor activity, but could not slow down the tumor growth. The nano-formulation groups without laser (upPhD NPs and pPhD NPs) showed better anti-tumor efficacy than free chemo-drugs, suggesting that our nanoparticles could improve drug efficacy. However, the single chemotherapy still was not able to inhibit tumor progression effectively. The group of upPhD NPs with laser (upPhD NPs+L) showed more effective tumor inhibition and effectively prevented the tumor progression. Most interestingly, the transformable, "Trojan Horse" like nanoparticles (pPhD NPs+L) exhibited exceptional anti-tumor efficacy, with 100% complete cure rate (FIG. 15d), which was much higher than the laser treated non-transformable nanoparticles (50%), and other control groups (0%). The best anti-tumor efficacy of pPhD NPs+L group was further demonstrated in orthotopic tumors (FIG. 15e), which achieved 100% complete cure rate as well (FIG. 15f). The tumor images of subcutaneous and orthotopic models that treated by pPhD NPs+L (FIG. 15g and FIG. 15h) and upPhD NPs+L further indicated the superiority of the transformable nanoparticles to the non-transformable ones. Compared to that the non-transformable nanoparticles, the striking tumor elimination effect of pPhD NPs could be ascribed to the higher tumor accumulation, deeper tumor penetrations and increased cellar uptake due to their unique dual size and surface charge transformation properties. H&E staining was utilized to evaluate the phototherapeutic effect of free photosensitizer (Phy), non-transformable nanoparticles (upPhD NPs) and transformable nanoparticles (pPhD NPs) in tumor tissue compared with the PBS group. As shown in FIG. 15i, all the phototherapy groups caused different extent of tumor tissue damage, such as cellular destruction and apoptosis, in which the pPhD NPs induced the largest areas of damage in treated tumor tissue.

Figure 15J:
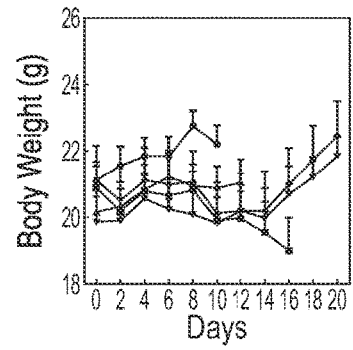

Systemic toxicity evaluations of pPhD NPs. The in vivo toxicity was evaluated by monitoring the body weight changes, hematoxylin & eosin (H&E) staining. FIG. 15j showed the body weights changes of the mice along the duration of the treatments. DOX-induced obvious body weights loss after the second dose of treatment; pPhD NPs did not exhibit systemic toxicity, since the mice gained body weights during the treatment. The lesion of major organs was evaluated by H&E staining. DOX showed obvious liver and heart toxicity, the striated muscle of heart disappeared. All other groups didn't exhibit distinguishable abnormality, indicated that our nanoformulation could extensively decrease the systemic toxicities of chemotherapeutic drugs.

Example 11. Preparation of Nanoparticles Encased in Red Blood Cell Vesicles

Materials. Pheophorbide A (Pa) was bought from Santa Cruz Biotechnology. Irinotecan (Ir) was purchased from BIOTANG Inc. (MA, USA). DCF-DA and all solvents were purchased from Sigma-Aldrich (MO, USA).

Preparation of RBC-membrane-derived vesicles. An expired unit of donor packed red blood cells was acquired from the UC Davis Medical Center hospital transfusion services, and the provision approved by the Department of Pathology Clinical Research Oversight Committee Internal Review. RBC membrane was prepared according to previous studies with modification. Briefly, the RBCs were lysed in the hypotonic medium (0.25×PBS) for 90 mins on ice. Samples were centrifuged at 80000×g for 90 min with a Beckman L7-65 Ultracentrifuge. The supernatant was removed and the pink pellet was re-suspended in water. The membrane protein concentrations were quantified using BCA protein assay kit (Pierce, Rock-ford, Ill.).

Synthesis and characterizations of RBC-PI nanoparticles. Synthesis of Pa and Ir conjugate (PI) was performed through ester formation according to our previous studies. To synthesize RBC complexed PI (RBC-PI) nanoparticles, the PI conjugates were first dissolved in acetone at a 1 mg/mL concentration. One mL of the solution was added rapidly to 3 mL of water followed by adding 20 µL trimethylamine. The mixture was immediately put under Ultrasonic Cleaner (VEVOR, 110 W, 60 kHz) and homogenized for 30s at amplitude of 20%. After adding 1, 2, or 4 mg RBC cell membrane (calculated based on protein concentrations) to form RBC-PI with ratios of RBC membrane to PI at 1:1, 2:1, and 4:1; the solution was further sonicated in the water bath of a Digital Ultrasonic Cleaner (Vevor, 120 W, 40 kHz) for 2 minutes to form nanoparticles.

The morphology of RBC-PI was observed under cryo-transmission electron microscopy (JEM-2100F, Tokyo, Japan), while the size distribution and zeta potentials were measured by dynamic light scattering (DLS) instrument (Zetasizer, Nano ZS, Malvern, UK). The stability test was performed in the presence of 10% FBS/PBS at the 1 mg/mL (PI concentration). The size distribution and polydispersity index (PDI) of each time point were tested by dynamic light scattering for a 30-day period.

Example 12. Properties of Nanoparticles Encased in Red Blood Cell Vesicles

Methods

Evaluation of in vitro ROS and heat production upon illumination. Different concentrations of RBC-PI or PI NPs were placed in 96-well plate, and exposed under 680 nm laser at 0.8 W/cm$^2$ (Shanghai, China) for 3 min. The heat generations were recorded by NIR thermal camera (FLIR, Santa Barbara, Calif.). The ROS productions were measured by using DCF-DA, as the indicator. Briefly, different concentrations of RBC-PI or PI NPs were incubated with 50 µM DCFH-DA the working solution followed by light treatment (680 nm, 0.8 W/cm$^2$ for 3 min). The fluorescence was quantified by SpectraMax M3 microplate reader (Molecular Devices, LLC, CA)

Drug release studies. Three hundred microliters of 50 µM RBC-PI (1:1) solutions adjusted to two different pH values (7.4 or 5.4) were placed in a 96-well plate. Each group at different pH was then treated with 0, 0.4, or 0.8 W 680 laser for 3 minutes. Laser was applied with 12 minutes interval to minimize the heat effect for drug release. At each time point, 2 µL of solutions from each sample were diluted into 98 µL DMSO to test released Ir fluorescence after light trigger. Of note, Ir fluorescence was quenched when conjugated with Pa.

Cell uptake and intracellular ROS production. The A549 lung cancer cells were seeded in a 12-well dish (2×10$^5$ cells/well) and then incubated with 25 µM RBC-PI or PI NPs for 4 hours. After three times of washes with PBS, cells were incubated with 50 µM DCF-DA for 30 minutes. Samples were treated with or without light (630 nm, Omnilux New-U LED panel) for 1 minute, and intracellular PI uptake (based on Pa fluorescence) and ROS production were analyzed by flow cytometry (FACSCanton™, BD Bioscience, SD, CA).

Cellular uptake. The A549 lung cancer cells were seeded in glass-bottom dishes (Cellvis, Mountain View, Calif.) and treated with 25 µM RBC-PI. Two hours later, samples were replaced with fresh medium and treated with or without 630 nm LED light for 30 seconds every 2 hours. A relatively low light dose was used to avoid too much cytotoxicity. The intracellular fluorescence of Pa and Ir was monitored by fluorescence microscopy (Olympus IX81/IX2-UCB system, CV, PA) at different time points.

Cytotoxicity assay. Cell viabilities were determined by MTS method according to manufactory manual (Promega, Madison, Wis.). A549 cells were seeded in 96-wells plates with a density of 5000 cells per well. The cells were treated with different concentrations of RBC-PI (1:1), PI NPs, free Pa and Ir at the comparable concentrations. Six hours later, medium was replaced with fresh complete media followed by illumination with 630 nm light for 3 minutes. After additional 24 hours incubation, MTS working solution was added and the absorbance at 490 nm was evaluated by SpectraMax M3 microplate reader. Experiments were performed in triplicate, and 3 independent experiments were conducted.

Cellular uptake study with macrophage-like cells. Human U937 macrophage-like cells were seeded in 96-well plates at a density of 5000 cells per well overnight. U937 cells were stimulated with 10 nM of PMA (Sigma-Aldrich) for 24 hours. Samples were replaced with fresh medium and treated with RBC-PI (1:1) and PI NPs at the concentration of PI molecule at 25 µM. The cells were then incubated with 0.5% Triton X-100 for 12 min and then added into 4 times DMSO (v/v). To quantify the particle uptake by U937 cells, fluorescence of Pa was detected by using an SpectraMax M3 micro-plate reader.

Pharmacokinetic evaluation. All animal studies were approved by the University of California Davis Institutional Animal Care and Use Committee (IACUC #07-13119 and 09-15584) and the procedures were in accordance with institutional guidelines. The jugular vein cannulated female Sprague-Dawley rats (200 g) were purchased from Harland (Indianapolis, Ind.) allowing easy drug administration and multiple blood collections. Five mg/kg RBC-PI (1:1) and PI NPs (2.5 mg/kg of Pa and 2.5 mg/kg of Ir) were i.v. administered into rat (n=3 for each group). Whole blood samples (~150 µL) were collected via jugular vein catheter at the predetermined time points post injection. Twenty microliters of plasma samples were mixed with 80 µL DMSO and Pa fluorescence was measured using Ex/Em: 412/680 nm channel. Untreated plasma was served as a blank control.

Anti-cancer efficacy study in tumor bearing mice. 4-6 weeks of nude mice were purchased from the Jackson Laboratory (Sacramento, Calif.). Lung cancer bearing models were established by subcutaneously injecting 2×10$^6$ A549 cells into flank. After tumor reaching the size of 500-650 mm$^3$, mice were than randomly assigned into 4 groups: PBS, free mixture of Pa and Ir, PI and RBC-PI (1:1) (equal to 10 mg/kg of Pa and 10 mg/kg of Ir) (n=6 per group). Drugs were intravenous (i.v.) injected and tumors were illuminated at 24 h, 48 h, 72 h and 96 hours post-injection. The whole tumor region was covered by the light spot (0.8 cm$^2$ in diameter) generated from a 680 nm laser with 1.2 W/cm$^2$ for 3 min. Tumor surface temperature was determined by a NIR thermal camera. Animals were monitored every day, and body weight and tumor size were measured twice a week. The tumor size was calculated using the following formulation: Length×Width$^2$/2 (mm$^3$).

In vivo bio-distribution study. The in vivo biodistribution study was evaluated in the A549 tumor bearing mice. After tumor reached 500-650 mm$^3$ in size, tumor-bearing mice were randomly assigned into two groups (n=3 per group): RBC-PI (1:1) and PI NPs (20 mg/kg PI, equal to 10 mg/kg of Pa and 10 mg/kg of Ir). Twenty-four and forty-eight hours post i.v. injection, mice were sacrificed, and tumors and major organs were collected. About 100 mg of each organ were homogenized in PBS, followed by centrifugation at 20,000×g for 10 min. The collected supernatants were added 5 times methanol to precipitate the protein. The solvent was further removed by vacuum. The PI (based on Pa fluorescence) concentration was measured by re-dissolution in methanol with SpectraMax M3 microplate reader. Results were expressed as PI weight in per gram of tissue.

Statistics. Data are presented as mean±standard deviation (SD). Group comparisons were carried out using one-way analysis of variance or Student's t test. P value less than 0.05 was considered statistically significant difference.

Results and Discussion

Preparation and Characterization of biomimicry RBC-PI complex. We previously developed a novel full-API nanoparticle (PI) self-assembled from the conjugates of a hydrophobic photosensitizer, pheophorbide A (Pa), and Irinotecan (Ir), a relatively hydrophilic anti-neoplastic drug. Based on its amphipathic nature, PI could self-assemble into nanoparticles without excipients, and could be used for tri-model treatment modalities, including photodynamic therapy, photothermal therapy and chemotherapy. However, PI NPs were not very stable and their strong positive charge (+42 mV) resulting in less-ideal blood circulation time (9.1±2.7 h), and thus rendered their full potentials for cancer therapy. Inspired by the interesting strategy of using RBC cell membrane biomimicry surface modification to dramatically extend nanoparticle's circulation time, we first introduced cell membrane to modify PI NPs based drug self-delivery system to improve their stability, PK profile and anti-therapeutic index.

Firstly, RBC cell membrane was extracted by hypotonic shock followed by mini-extrusion. At the initial intend, with simple mixing strategy, strongly positively charged PI NPs rapidly interacted with negatively charged RBC vesicles resulting in precipitation through strong electrostatic force. This was similar with the finding described by Luk et al when they tried to mix RBC vesicles with positively charged PLGA polymeric cores. It is interesting to note that most reported cell membrane coated nanoparticles required a core which usually had the negative zeta potential, as this would allow cell membrane to coat on the surface through extrusion or self-assemble. One exception was silica/silicon nanoparticles which had weak positive charge (+5-+15); however, based on the published TEM pictures cell membrane formed "small aggregates" on the silica surface.

To circumvent this limitation, we newly developed a method using triethylamine (TEA) to temporarily neutralize the positive charge of PI NPs to prevent the strong electrostatic interaction. Under this condition, RBC membrane was then added and TEA was slowly removed followed by a short 2-minute sonication. This method allowed RBC vesicles and PI NPs to form stable nanoparticles.

Figure 16A:
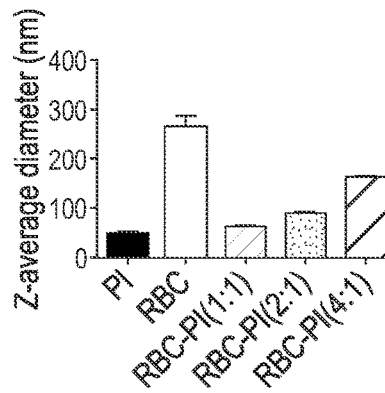
FIG. 16a-e shows FIG. 16a) Size distribution, and FIG. 16b) zeta potential of the RBC-membrane-PI-complexed nanoparticles at different ratios.
Figure 16B:
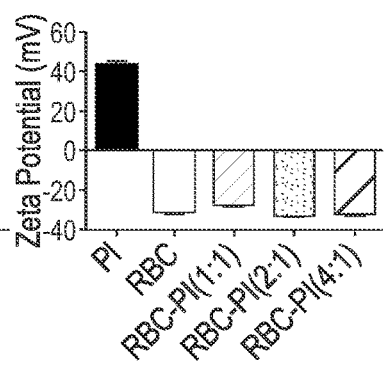
Figure 16E:
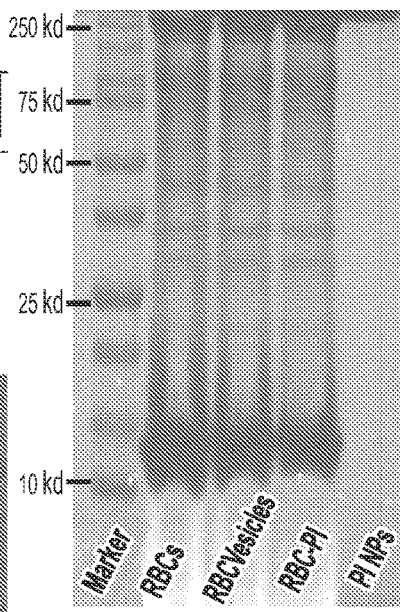
Figure 16C:
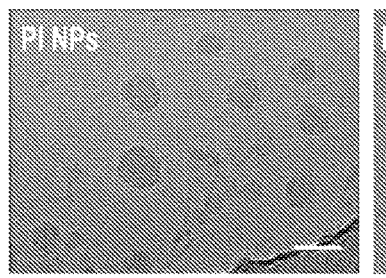
Figure 16C:
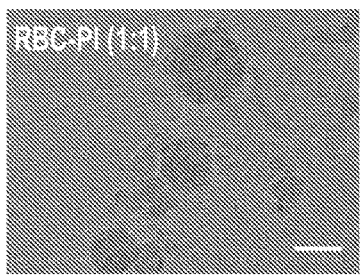
Figure 16D:
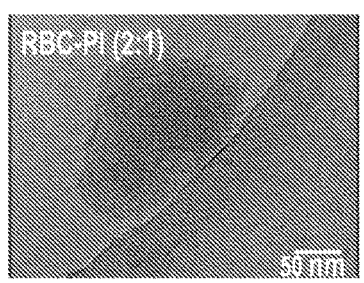
Figure 16D:
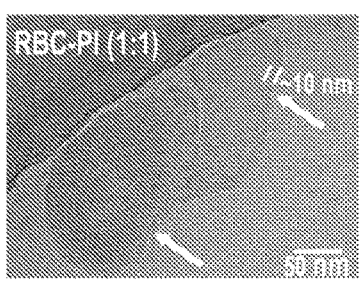
Figure 16D:
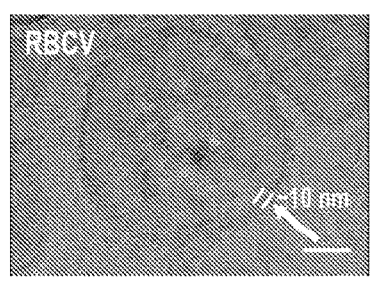

To further characterize this new nanostructure formed by PI and RBC membrane, we used different ratios of these two components and evaluated the changes in size, zeta potential, and morphology. As seen in the FIG. 16a & FIG. 16b, the RBC vesicles and PI NPs exhibited an average diameter of 190 nm and 50 nm with zeta potential of −31 mV and +43 my, respectively. When we assembled them together with different ratios using the method described above, nanoparticles could be formed with the ratios of 1:1 to 4:1 (RBC vesicles protein concentration to PI molecular weight ratio). The size of the resulting RBC-PI fell between the original PI NPs and vesicles formed by cell membrane; and this was RBC vesicles amount-dependent (FIG. 16a, FIG. 16b). Also, the zeta potential of the nanoparticles with different ratios also decreased from +43 mV to −29--32 mV, which was comparable with that of the RBC membrane vesicles (FIG. 16d). Those results indicated that the surface of PI nanoparticles was successfully modified by the RBC vesicles.

However, the membrane amount-dependent size changes were unexpected as the sizes of other types of cell membrane coated core-shell nanoparticles were solely based on the core size. Therefore, we suspected the formation of a distinct structure and the occurrence of additional interactions between RBC membrane and PI monomers. Cryo-electron microscopy was employed to visualize the morphology changes of RBC-PI nanoparticles at different ratios (FIG. 16c, FIG. 16d). A "core-like" structure was observed with a membrane amount-dependent increase in size, but the density of "core-like" structures decreased. When the ratio of RBC protein concentration to PI was set to 4:1, excess cell membrane stretch from the "core-like" nanoparticles to form a "hand-bag" structure (FIG. 16d).

In our system, we believe that the weak intermolecular forces between RBC membrane and PI resulted in stable RBC-PI nanoparticles. As we all known, solid particles in a liquid medium are subject to weak interaction forces. Among those forces, van der Waals forces, hydrogen bonds and π-π interactions are the most important low-energy forces in self-assembled systems for keep nanoparticles stable. These forces combined both attractive and repulsive interactions which depend on aggregation degree of intermolecular. These phenomena could be exactly observed in our cryo-EM images (FIG. 16c, FIG. 16d). We speculated that PI monomers dispersed in both aqueous core and bilayer of RBC vesicles. When the ratio of RBC protein concentration to PI close to 1:1, attraction was the dominant force to keep RBC-PI nanoparticles stable in a comparative small size (around 60 nm). These attraction interactions come from both PI to PI and PI to phospholipid of RBC vesicles. Along with increasing amounts of RBC vesicles, repulsive force made nanoparticles bigger and finally part of RBC membrane stretched outside (FIG. 16d).

These unique morphological and structural features distinguished RBC-PI nanoparticles from other reported cell membrane coating core-shell nanoparticles or liposome-like drug loading nanoparticles. The reported cell membrane coating core-shell nanoparticles usually had a firm polymeric core on which membrane could be attached through the electrostatic interaction and hydrophobic force. Additionally, the negative surface charged cores played an important role in the formation of membrane coating core-shell nanoparticles while the positively charged cores formed observable aggregates because of the strong electrostatic interaction. Our formulation also differs from liposome formulations, which usually load hydrophobic drugs inside their phospholipid bilayer or hydrophilic drug into their aqueous core. Their ring-shaped phospholipid bilayer structures and discrete structures of drug could easily be recognized in cryo-EM images due to the comparatively high contrast of the liposomes and drug precipitates. However, a typical double-layered structure was not observed on the nanoparticle surface (FIG. 16c), these may also be attributed to PI molecules distributed in both aqueous core and bilayer of RBC vesicles that decreased the contrast between the bilayer and core. In the end, these results suggested that RBC membrane not only modified the particle surface, but also complexed with PI to jointly form the "core-like" structure (FIG. 16b). Most importantly, RBC-PI nanocomplex still maintained the protein pattern similar to that of normal RBCs (FIG. 16e).

Figure 17:
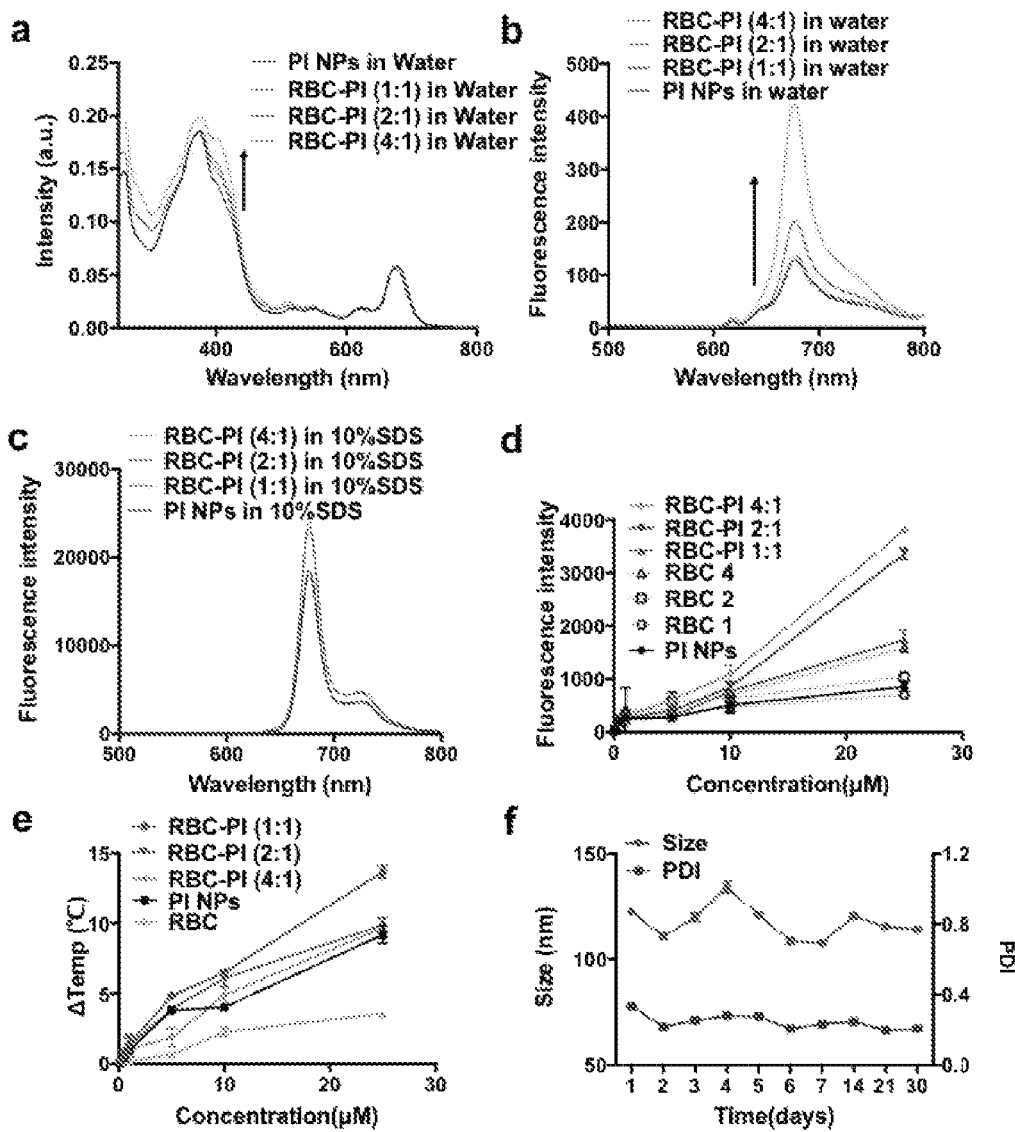
FIG. 17a-f shows FIG. 17a) UV-Vis absorbance of PI NPs and RBC-PI with various RBC vesicles-to-PI ratios in water; Fluorescence spectra of PI NPs and RBC-PI with various RBC vesicles-to-PI ratios in water FIG. 17b) and 10% SDS FIG. 17c) with excitations of 412 nm (PI concentration: 50 nM)

Physical and functional analysis of RBC-PI. The PI NPs and RBC-PI nanoparticles showed similar UV spectra with characteristic peaks at 370 nm, which represented the characteristic absorption of Ir. The characteristic absorption of Pa were shown at 412 and 670 nm. However, the 412 nm peak overlapped with 370 nm peak of Ir (FIG. 17a). Similar to other RBC-coating nanoparticles, we observed a red-shift of about 20 nm from 417 to 437 nm along with increased RBC membrane to PI ratio.

To further dissect the unique architecture of our nanoparticles, we performed further experiments to compare the changes in physical and functional properties of RBC-PI at different RBC vesicles-to-PI ratios. As an intrinsic photosensitizer, PI NPs could produce fluorescence, heat and ROS for image-guided cancer therapy. Due to the π-π interaction, the fluorescence of PI NPs was quenched in water but could be recovered after dissociation in 10% SDS solution (FIG. 17b-FIG. 17c). We hypothesize that the package of PI molecules in RBC-PI after interaction with cell membrane was less compact compared to that in the parent PI NPs resulting in less quenching effects. Interestingly, with the increasing RBC vesicles-to-PI ratios, the degree of fluorescence quenching diminished in water (FIG. 17b). The fluorescence of all nanoparticles dramatically increased after dissociation in the presence of 10% SDS (FIG. 17b). The quenching ratio (fluorescence in the present of SDS/fluorescence in water) decreased from 140 to 55 for PI NPs (0:1) to RBC-PI (4:1) with increasing amount of cell membrane. Similarly, there was a dose-dependent ROS production for both PI NPs and RBC-PI. RBC-PI (4:1) had the highest ROS production which was in line with its lowest quench effects. Interestingly, this ROS production could be also partially contributed by the components of RBC membrane, as RBC vesicles also produced ROS upon illumination (FIG. 17d).

Lastly, a dose-dependent temperature increase in both PI NPs and RBC-PI nanoparticles upon illumination were also observed (FIG. 17e). When the PI molecules self-assembled and quenched, it could induce a structural reconfiguration and the most photo-energy was transformed into heat depending on the ratio of quenching. Therefore, when quenching ratio in molecular motion decreased with the increased amounts of cell membrane (FIG. 17b, FIG. 17c), the heat production ability decreased (FIG. 17e). Intriguingly, similar to ROS production, RBC membrane vesicle appeared to play a role in heat production in RBC-PI. Thus, at the similar quenching ratio between PI NPs and RBC:PI (1:1), RBC:PI (1:1) had significant higher heat production (FIG. 17e). These phenomena could be likely attributed to the RBC intrinsic hemoglobin bound protoporphyrin and iron. The presence of protein in RBC membrane was detected in the SDS-PAGE of red blood cells and RBC membrane (FIG. 16e). Collectively, these results strongly supported our notion that RBC membrane endowed into PI nanoparticles resulting in physical and functional changes, but not a simple surface coating like other reported cell membrane coating core-shell nanoparticles.

Figure 18:
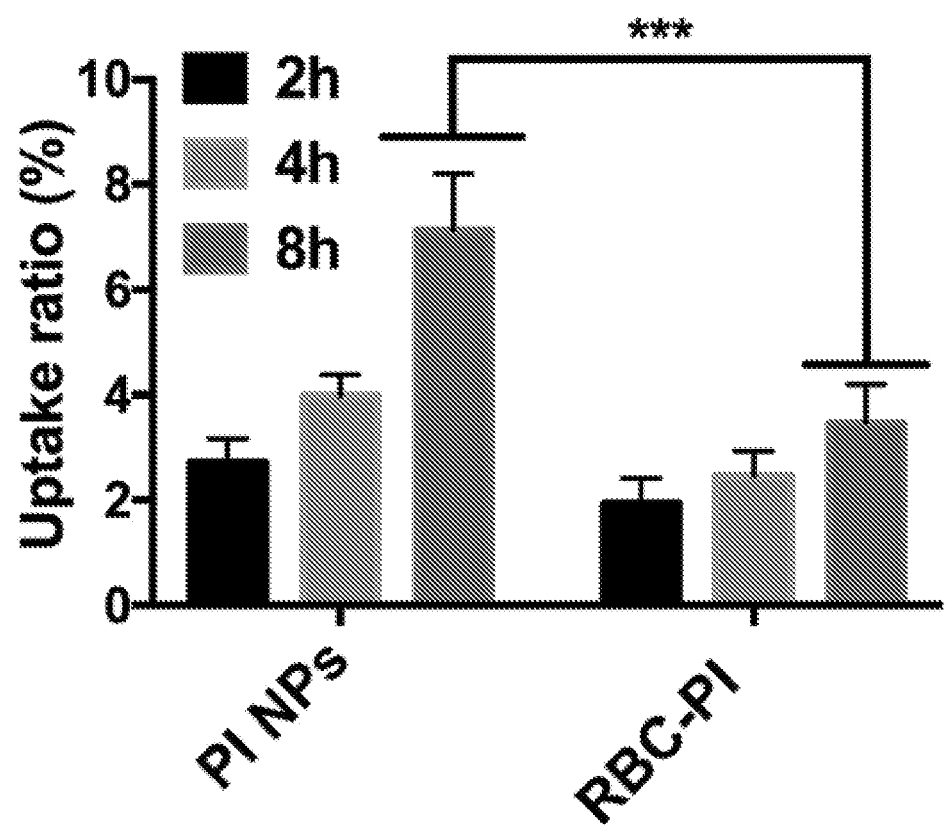
FIG. 18 shows intracellular uptake of RBC-PI and PI nanoparticles in RAW267.4 cells after 2, 4, 8 h incubation (***P<0.0001).

The nanostructures of PI suffered from ion change in different solutions resulting in aggregation. The small size of pure nanodrug have massive surface area results in sufficiently high free energy or surface charge that might cause attraction or agglomeration, which leads to recrystallization into larger particles. This also known as ostwald ripening. Furthermore, pure nanodrug that consists of water-insoluble drugs are always susceptible to precipitation upon dilution in blood, gastric and other body fluids after administration into the body. Therefore, excipients or stabilizer are still needed in pure drug self-delivery systems. We investigated the stability of RBC-PI in PBS (pH 7.4) solution the presence of fetal bovine serum (FBS). As shown in FIG. 17f, RBC-PI displayed excellent stability through a 30 days period in terms of size and PDI. In contrast, PI NPs were not stable for long-time (FIG. 18) and precipitated within 7 days in the presence of FBS. Based on this, the new cell membrane complexing technique described here provides a perfect solution to enhance the in vivo stability of these pure drug self-delivery systems.

Figure 19A:
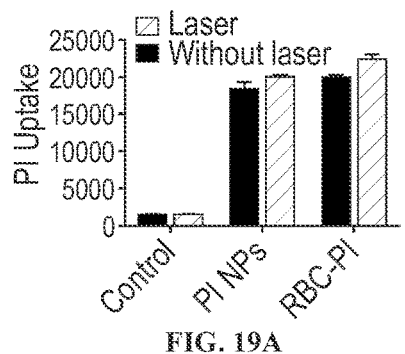
FIG. 19a-d shows uptake and photo-chemotherapy in A549 human lung cancer cells.
Figure 19B:
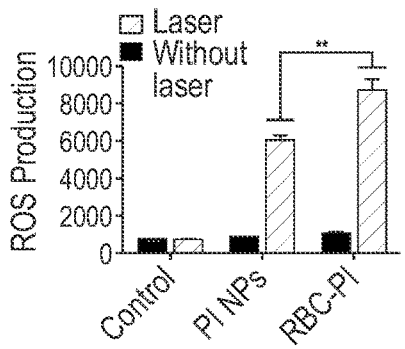

In vitro light triggered chemophototherapy of RBC-PI. Since RBC-PI (1:1) was very stable even in the presence of serum, and had the highest drug loading ratio and the smallest size for potentially better tissue penetration, we chose this formulation for the following in vitro and in vivo studies. We first evaluated the cellular uptake of RBC-PI and PI NPs, and found RBC-PI could be effectively uptake by A549 human lung cancer cells at the comparable amounts with PI (FIG. 19a). Upon laser illumination, RBC-PI treated cells had higher intracellular ROS production compared to PI NPs treated cells (FIG. 19b), which was consistent with the finding that RBC-PI had better ROS production efficiency (FIG. 17d), compared to PI NPs. Cells treated with free irinotecan did not produce intracellular ROS upon light treatment.

Figure 19C:
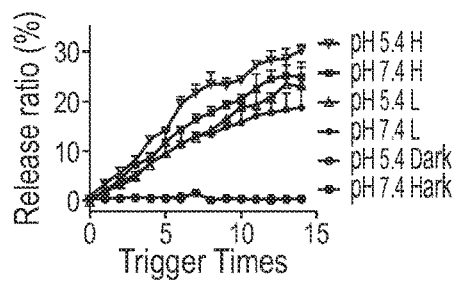
Figure 19D:
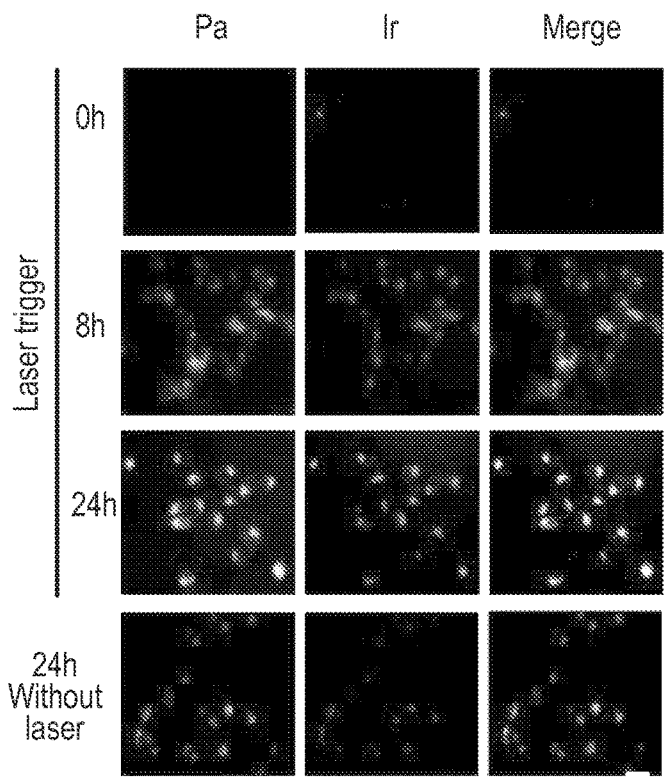
Figure 20A:
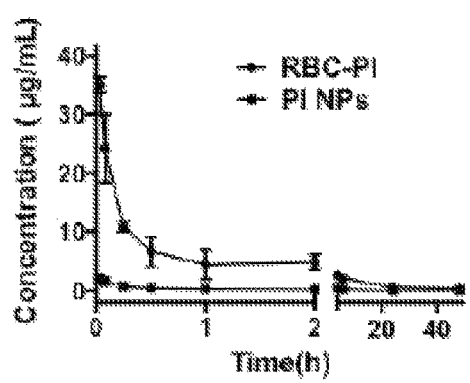
FIG. 20a-b shows FIG. 20a) Pharmacokinetic evaluations of RBC-PI and PI NPs (5 mg/kg) in rats (n=3).
Figure 20B:
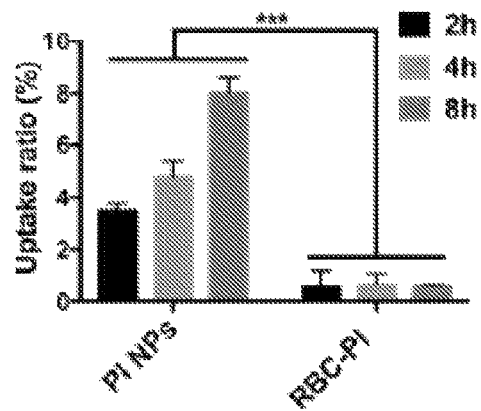

Pa and Ir was conjugated with an ester bond, which could be cleaved in the presence of acidic pH (e.g. pH 5.4 in the lysosome) resulting in drug release. Similar to our previous finding in PI NPs, Ir release from RBC-PI was triggered by laser treatment with a higher efficiency in the acidic pH compared to neutral pH (FIG. 19c). The drug release kinetics could be also monitored at the cell line level under a fluorescence microscope. A549 cells were treated with RBC-PI followed with laser treatments or without laser treatments. FIG. 20b illustrated a time-dependent RBC-PI uptake evidenced by increased porphyrin signals, which came from the free Pa molecules cleaved from PI conjugates inside cells after the dissociation of RBC-PI. The blue fluorescence Ir was quenched when conjugated with Pa, but was restored after cleavage from PI conjugates upon light treatment. In contrast, without light treatment, lower level of both Pa and Ir signals was appreciated indicating a slower drug release process without light treatment, as the uptake amount should be the same. Those results confirmed that similar to PI NPs, laser could also markedly expedite the drug release from RBC-PI.

Pharmacokinetics and macrophage uptake. As shown in FIG. 17f, we have demonstrated that RBC-PI displayed excellent stability throughout the 30-day period with minimal changes in both size and PDI. The rapid clearance of nanoparticles from the blood because of the recognition by immune system undoubtedly limits the time window for their passive tumor accumulation via EPR effect. In addition, a strong positive charge surface also enhanced macrophage uptake. PI nanoparticles suffered from low serum stability and rapid clearance partially due to strong positive charges, while RBC-PI nanocomplex should greatly overcome those drawbacks. As expected, we demonstrated that RBC-PI had superior pharmacokinetic profile to PI NPs in rats. As seen in the FIG. 20a, RBC-PI had significant longer half-life (17.3 vs 9.1 h) and almost 10 times higher area under curve (AUC) (58824 vs 5902.7 ug/L*h) than PI NPs.

In addition to the attribute from the enhanced serum stability, we believed RBC membrane modification further decreased macrophage uptake resulting in slower clearance. Therefore, we incubated RBC-PI and PI with phorbol 12-myristate 13-acetate (PMA) activated human U937 macrophage-like cell lines for 2, 4, and 8 hours. The macrophage phagocytosis of RBC-PI and PI were quantified based on fluorescence intensity of Pa. There was a time-dependent macrophage uptake of PI NPs (FIG. 20b). At 8 hours, RBC-PI had more than 8 times less macrophage uptake compared to PI. Similar results were observed using mouse macrophage-like cell line RAW 264.7, but in less difference (2 times less uptake). RBC-PI appeared to be recognized by mouse macrophages. This could be because mouse macrophages could still recognize the species difference on human RBC surface antigens. This was fully expected, while other studies usually employed rodent RBCs for their study and thus did not encounter these phenomena. Functional RBC cell membrane proteins such as CD47 and CD59 have been identified on RBC surfaces as self-markers that actively signal macrophages and prevent their uptake. Those inherited surface markers could protect cell membrane coated nanoparticles from immune surveillance. Therefore, the immune-evasive function of RBC-PI was attributed by two factors: i) compared to strong positive charge of PI NPs, the negative surface charge of RBC-PI were less preferred for phagocytosis by macrophage cells; ii) the "don't eat me" surface markers inherited from RBCs on the RBC-PI surface could prevent macrophage uptake.

Figure 21:
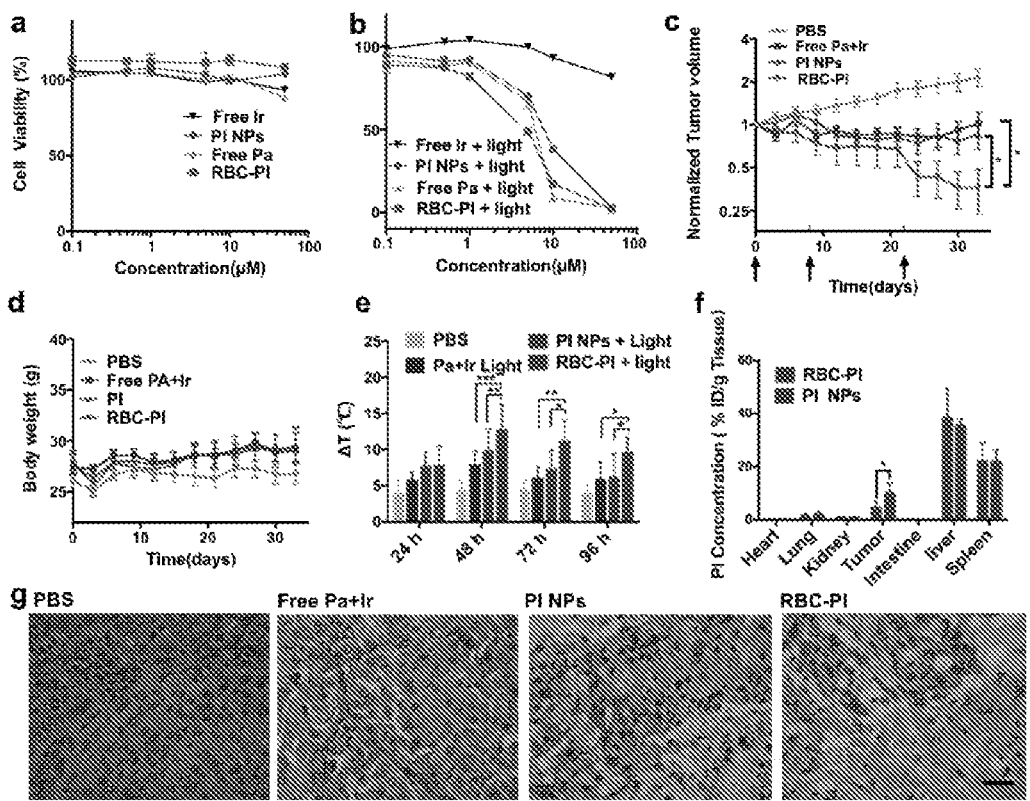
FIG. 21a-g shows cell viability studies of free Pa, Ir, PI NPs and RBC-PI against A549 human lung cancer cells with FIG. 21a) or without FIG. 21b) laser treatments. Anti-cancer efficacy studies were performed in the A549 tumor-bearing mice; Tumor volume ratios FIG. 21c) and body weight FIG. 21d) changes of mice treated with PBS, mixture of Pa+Ir, PI NPs, and RBC-PI (equal to 10 mg/kg of Pa and 10 mg/kg of PI) on day 1, 7 and 21 followed by light treatments (n=6). Tumors were illuminated with 680 nm laser at 1.2 W for 3 minutes at 24, 48, 72, and 96 hours after each injection.

In vitro chemophototherapeutic effects. The in vitro cytotoxic effects of the free drug, PI NPs and RBC-PI were evaluated in A549 cells. Free drug, PI NPs and RBC-PI were all exhibited negligible cytotoxicity without light treatment which indicated that RBC membrane did not cause toxicity and the Ir release was limited such condition (FIG. 21a-FIG. 21b). In contrast, upon light treatment, a dose-dependent antitumor activity was observed in free Pa, PI NPs and RBC-PI groups. The $IC_{50}$ values for PI NPs, Pa and RBC-PI are 12.7, 7.0 and 5.4 µM, respectively. The above results indicated that RBC-PI retained the chemophototherapeutic effect of PI NPs.

In vitro chemophototherapeutic effects. The in vitro cytotoxic effects of the free drug, PI NPs and RBC-PI were evaluated in A549 cells. Free drug, PI NPs and RBC-PI were all exhibited negligible cytotoxicity without light treatment which indicated that RBC membrane did not cause toxicity and the Ir release was limited such condition (FIG. 21a-FIG. 21b). In contrast, upon light treatment, a dose-dependent antitumor activity was observed in free Pa, PI NPs and RBC-PI groups. The $IC_{50}$ values for PI NPs, Pa and RBC-PI are 12.7, 7.0 and 5.4 µM, respectively. The above results indicated that RBC-PI retained the chemophototherapeutic effect of PI NPs.

In vivo antitumor efficacy. To assess the in vivo antitumor efficacy, the A549 tumor-bearing mice were administrated with free Pa+Ir, PI NPs and RBC-PI on day 1, 7 and 21; tumors were treated with laser (680 nm, 1.2 W/cm$^2$) for 3 min at 24, 48, 72, and 96 hours post-injection. As shown in FIG. 21c, free Pa+Ir and PI NPs treated groups showed better tumor reduction than PBS control. Among all treatment groups, RBC-PI group displayed the best anti-tumor efficacy. The body weight of the mice showed negligible variation during the treatment (FIG. 21d) suggesting a generally low toxicity in all groups.

Local heat production is one of the major factors to destroy local tumor for PI mediated phototherapy, and thus we recorded the tumor surface temperature at different time points post-injection (FIG. 21e). Tumor surface temperature in Pa+Ir, PI NPs, and RBC-PI groups were all increased compared to that in PBS group. Among those days, 48 hour time point appeared to reach the peak for all treatment groups and temperature started to decline afterwards. Most importantly, RBC-PI treated groups had significantly higher tumor temperature increase than both PI NPs and Pa+Ir groups even after 96 hours. This was presumably due to the longer circulation time after RBC vesicles complexing allowing significantly better drug accumulation at the tumor sites, which was also confirmed with the biodistribution study (FIG. 21f). Besides, this result was consistent with our prior findings that RBC-PI (1:1) had better heat production ability than PI NPs at the same concentration (FIG. 3d). Unfortunately, we only observed a slight but not significant lower trend for the liver uptake in RBC-PI treated groups. As previously mentioned, this could be because mouse macrophages could still recognise human surface antigens due to species differences.

In addition to use the body weight changes for evaluation of systemic toxicity, we collected major organs for histopathology examination. There was minimal off-target toxicity detected in the organs examined. Tumors collected from the free Pa+Ir, PI NPs, and RBC-PI mediated chemophototherapy were also assessed. Compared to the PBS control group, free Pa—Ir treated tumor had some degrees of cell separation, while PI NPs and RBC-PI groups showed obvious decrease in cell density. Nuclear condensations and fragmentations and loss of cell morphology all suggested ongoing apoptosis and necrosis progresses after treatment. Taken together, we demonstrated that RBC-PI had superior in vivo anti-cancer therapeutic efficacy with high biocompatibility and low systemic toxicity.

In vivo antitumor efficacy. To assess the in vivo antitumor efficacy, the A549 tumor-bearing mice were administrated with free Pa+Ir, PI NPs and RBC-PI on day 1, 7 and 21; tumors were treated with laser (680 nm, 1.2 W/cm$^2$) for 3 min at 24, 48, 72, and 96 hours post-injection. As shown in FIG. 21c, free Pa+Ir and PI NPs treated groups showed better tumor reduction than PBS control. Among all treatment groups, RBC-PI group displayed the best anti-tumor efficacy. The body weight of the mice showed negligible variation during the treatment (FIG. 21d) suggesting a generally low toxicity in all groups.

Local heat production is one of the major factors to destroy local tumor for PI mediated phototherapy, and thus we recorded the tumor surface temperature at different time points post-injection (FIG. 21e). Tumor surface temperature in Pa+Ir, PI NPs, and RBC-PI groups were all increased compared to that in PBS group. Among those days, 48 hour time point appeared to reach the peak for all treatment groups and temperature started to decline afterwards. Most importantly, RBC-PI treated groups had significantly higher tumor temperature increase than both PI NPs and Pa+Ir groups even after 96 hours. This was presumably due to the longer circulation time after RBC vesicles complexing allowing significantly better drug accumulation at the tumor sites, which was also confirmed with the biodistribution study (FIG. 21f). Besides, this result was consistent with our prior findings that RBC-PI (1:1) had better heat production ability than PI NPs at the same concentration (FIG. 3d). Unfortunately, we only observed a slight but not significant lower trend for the liver uptake in RBC-PI treated groups. As previously mentioned, this could be because mouse macrophages could still recognize human surface antigens due to species differences.

In addition to use the body weight changes for evaluation of systemic toxicity, we collected major organs for histopathology examination. There was minimal off-target toxicity detected in the organs examined. Tumors collected from the free Pa+Ir, PI NPs, and RBC-PI mediated chemophototherapy were also assessed. Compared to the PBS control group, free Pa—Ir treated tumor had some degrees of cell separation, while PI NPs and RBC-PI groups showed obvious decrease in cell density. Nuclear condensations and fragmentations and loss of cell morphology all suggested ongoing apoptosis and necrosis progresses after treatment. Taken together, we demonstrated that RBC-PI had superior in vivo anti-cancer therapeutic efficacy with high biocompatibility and low systemic toxicity.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound having the structure of:

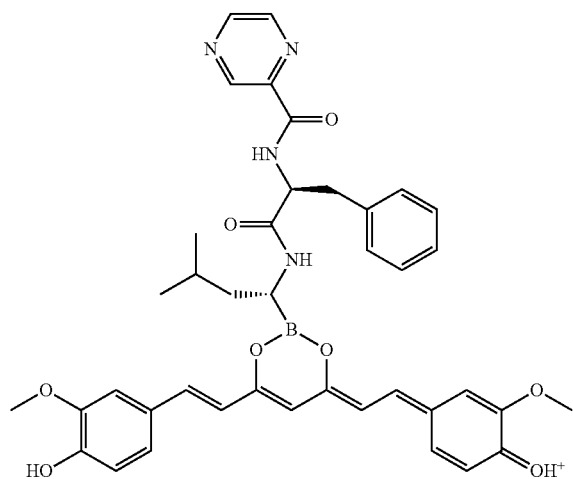

,

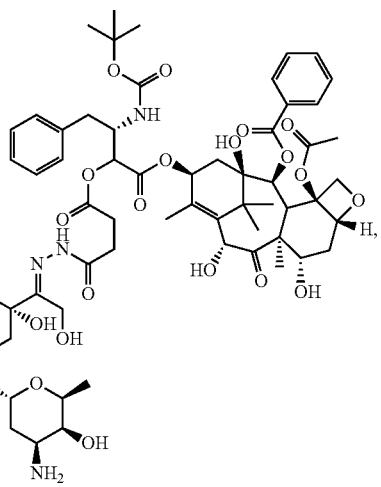

Doxorubicin-Docetaxel Amphiphilic Conjugate

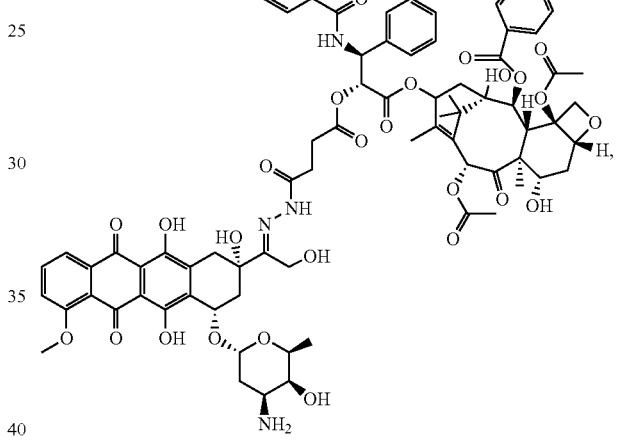

Doxorubicin-Paclitaxel Amphiphilic Conjugate

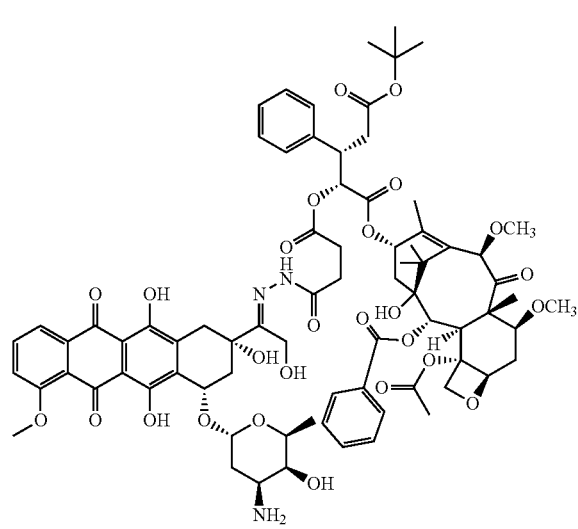

Doxorubicin-Cabazitaxel Amphiphilic Conjugate

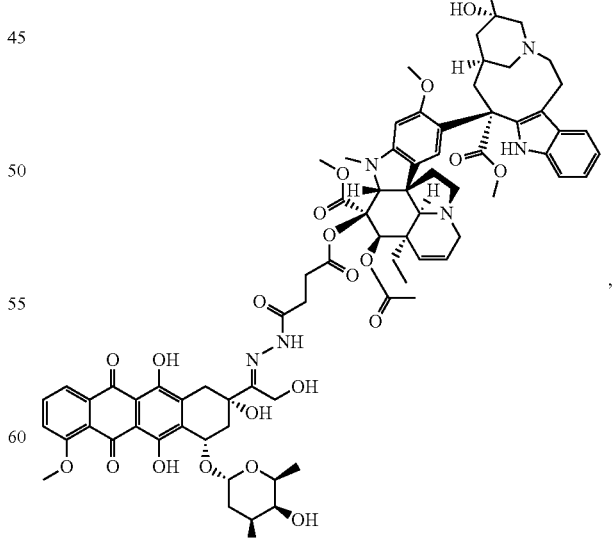

Doxorubicin-Vinblastine Amphiphilic Conjugate

-continued
or
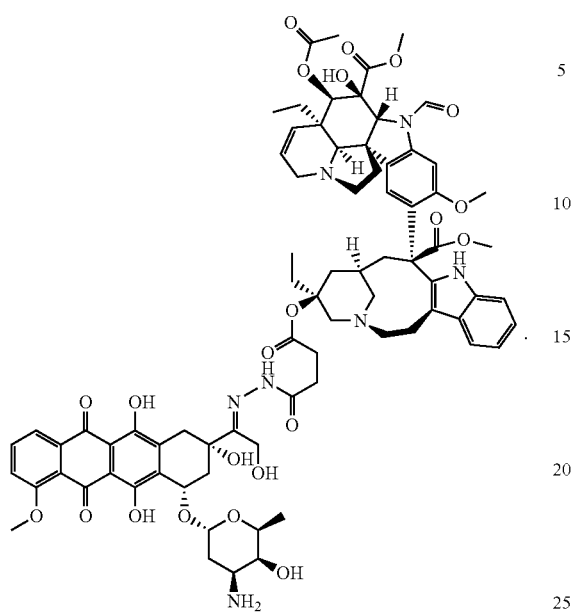
Doxorubicin-Vincristine Amphiphilic Conjugate
2. A compound having the structure of:
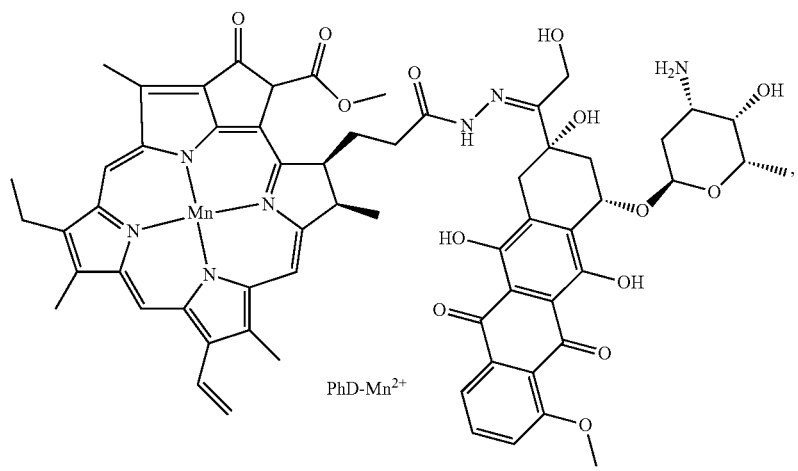
PhD-Mn$^{2+}$ 3. A compound having the structure of:
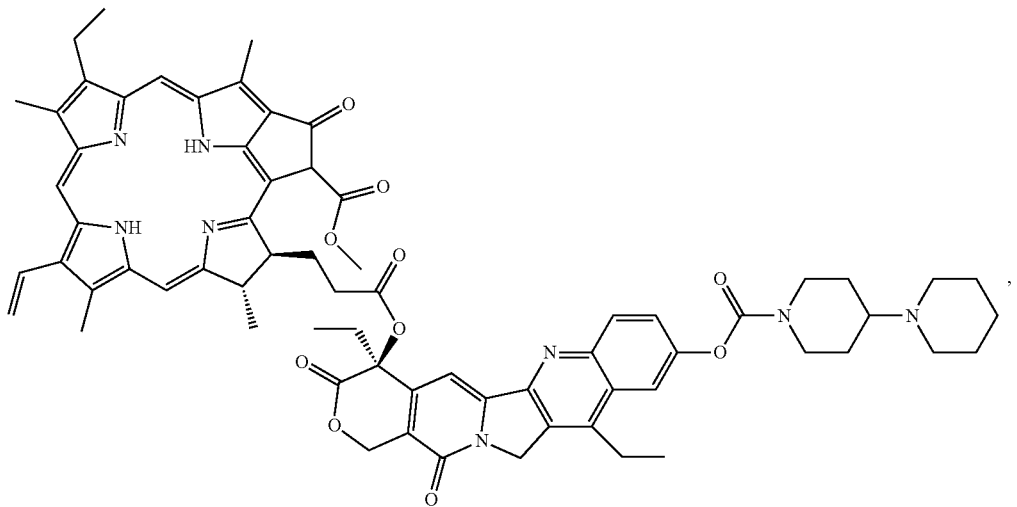
Pa-Ir Conjugate, Pl
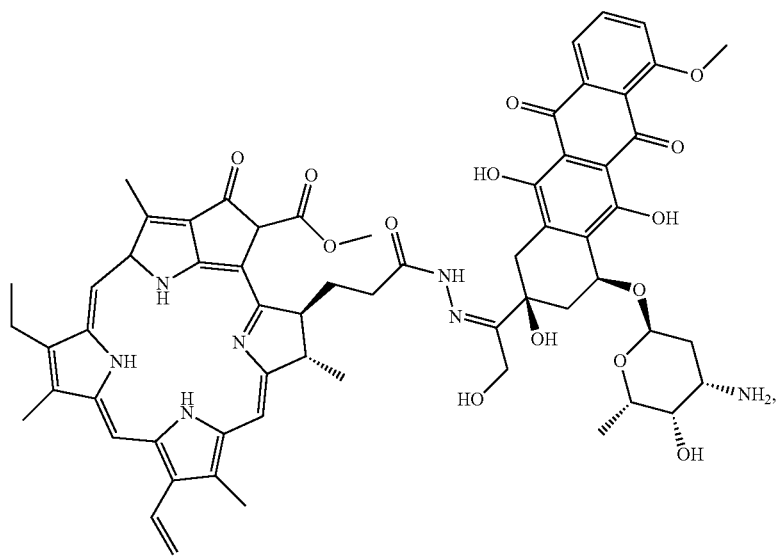
Porphyrin-Doxorubicin Amphiphilic Conjugate

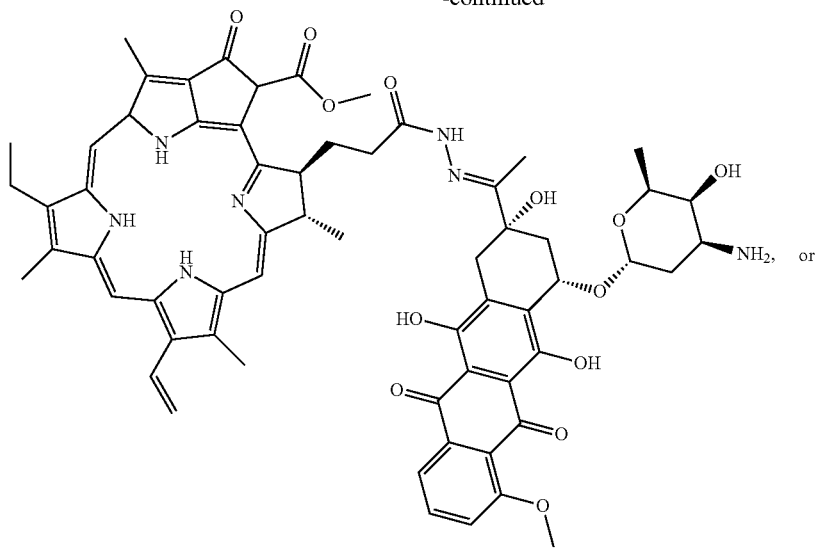

Porphyrin-Daunorubicin Amphiphilic Conjugate

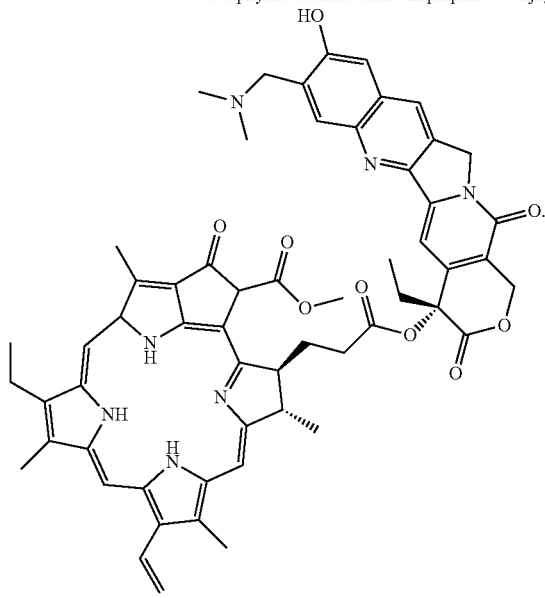

Porphyrin-Topotecan Amphiphilic Conjugate

4. A nanoparticle comprising a plurality of conjugates of claim 3, wherein the nanoparticle comprises an interior and an exterior.

5. A method of preparing a nanoparticle of claim 4, comprising forming a reaction mixture comprising a plurality of conjugates of claim 3 under conditions suitable for the plurality of conjugates to self-assemble and form nanoparticles.

6. A method of treating a disease or condition, comprising administering to a subject in need thereof, a therapeutically effective amount of a conjugate of claim 3, thereby treating the disease or condition.

7. A method of treating a disease or condition via sonodynamic therapy, comprising
administering to a subject in need thereof, a therapeutically effective amount of a conjugate of claim 3; and
exposing the subject to a sonic wave, thereby treating the disease via sonodynamic therapy.

8. A method of imaging a tissue or organ, comprising administering to a subject to be imaged, an effective amount of a conjugate of claim 3,
such that the conjugate or nanoparticle concentrates in the tissue or organ; and imaging the tissue or organ using a suitable device.

9. A method of detecting a tumor in a subject, comprising
administering to the subject an effective amount of a conjugate of claim 3;
exposing the subject to radiation at a first wavelength; and
detecting any emitted radiation from the conjugate or nanoparticle, thereby detecting the tumor.

10. A system comprising a conjugate of claim 3, and a laser.

11. A nanoparticle comprising a plurality of conjugates of claim 2, wherein the nanoparticle comprises an interior and an exterior.

12. A method of preparing a nanoparticle of claim 11, comprising forming a reaction mixture comprising a plurality of conjugates of claim 2 under conditions suitable for the plurality of conjugates to self-assemble and form nanoparticles.

13. A method of treating a disease or condition, comprising administering to a subject in need thereof, a therapeutically effective amount of a conjugate of claim 2, thereby treating the disease or condition.

14. A method of treating a disease or condition via sonodynamic therapy, comprising
   administering to a subject in need thereof, a therapeutically effective amount of a conjugate of claim 2; and
   exposing the subject to a sonic wave, thereby treating the disease via sonodynamic therapy.

15. A method of imaging a tissue or organ, comprising administering to a subject to be imaged, an effective amount of a conjugate of claim 2,
   such that the conjugate or nanoparticle concentrates in the tissue or organ; and imaging the tissue or organ using a suitable device.

16. A method of detecting a tumor in a subject, comprising
   administering to the subject an effective amount of a conjugate of claim 2;
   exposing the subject to radiation at a first wavelength; and
   detecting any emitted radiation from the conjugate or nanoparticle, thereby detecting the tumor.

17. A system comprising a conjugate of claim 2, and a laser.

18. A nanoparticle comprising a plurality of conjugates of claim 1, wherein the nanoparticle comprises an interior and an exterior.

19. A method of preparing a nanoparticle of claim 18, comprising forming a reaction mixture comprising a plurality of conjugates of claim 1 under conditions suitable for the plurality of conjugates to self-assemble and form nanoparticles.

20. A method of treating a disease or condition, comprising administering to a subject in need thereof, a therapeutically effective amount of a conjugate of claim 1, thereby treating the disease or condition.

21. A method of treating a disease or condition via sonodynamic therapy, comprising
   administering to a subject in need thereof, a therapeutically effective amount of a conjugate of claim 1; and
   exposing the subject to a sonic wave, thereby treating the disease via sonodynamic therapy.

22. A method of imaging a tissue or organ, comprising administering to a subject to be imaged, an effective amount of a conjugate of claim 1,
   such that the conjugate or nanoparticle concentrates in the tissue or organ; and imaging the tissue or organ using a suitable device.

23. A method of detecting a tumor in a subject, comprising
   administering to the subject an effective amount of a conjugate of claim 1;
   exposing the subject to radiation at a first wavelength; and
   detecting any emitted radiation from the conjugate or nanoparticle, thereby detecting the tumor.

24. A system comprising a conjugate of claim 1, and a laser.

* * * * *